US009428584B2

(12) United States Patent
Haegel et al.

(10) Patent No.: US 9,428,584 B2
(45) Date of Patent: *Aug. 30, 2016

(54) ANTIBODY AGAINST THE CSF-1R

(71) Applicant: Transgene, S.A., Illkirch Graffenstaden (FR)

(72) Inventors: Héléne Haegel, Illkirch Graffenstaden (FR); Christine Thioudellet, Strasbourg (FR); Michel Geist, Brumath (FR); Benoît Grellier, Strasbourg (FR); Jean-Baptiste Marchand, Obernai (FR)

(73) Assignee: Transgene S.A., Illkirch Graffenstaden (FR)

( * ) Notice: Subject to any disclaimer, the term of this patent is extended or adjusted under 35 U.S.C. 154(b) by 240 days.

This patent is subject to a terminal disclaimer.

(21) Appl. No.: 13/896,932

(22) Filed: May 17, 2013

(65) Prior Publication Data

US 2013/0289250 A1     Oct. 31, 2013

Related U.S. Application Data

(63) Continuation of application No. 13/026,944, filed on Feb. 14, 2011, now Pat. No. 8,470,977, which is a continuation-in-part of application No. 12/922,441, filed as application No. PCT/EP2009/001733 on Mar. 11, 2009, now Pat. No. 8,604,170.

(60) Provisional application No. 61/043,884, filed on Apr. 10, 2008.

(30) Foreign Application Priority Data

Mar. 14, 2008    (EP) ..................... 08360005

(51) Int. Cl.
*C07K 16/00*      (2006.01)
*C12P 21/08*      (2006.01)
*C07K 16/28*      (2006.01)
*A61K 39/00*      (2006.01)

(52) U.S. Cl.
CPC ..... *C07K 16/2866* (2013.01); *A61K 2039/505* (2013.01); *C07K 2317/24* (2013.01); *C07K 2317/56* (2013.01); *C07K 2317/565* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 2005/0059113 A1 | 3/2005 | Bedian et al. |
| 2005/0245471 A1 | 11/2005 | Balloul et al. |
| 2009/0317403 A1 | 12/2009 | Aharinejad et al. |
| 2011/0178278 A1 | 7/2011 | Haegel et al. |

FOREIGN PATENT DOCUMENTS

| | | |
|---|---|---|
| CA | 2090453 A1 | 1/1993 |
| EP | 1033401 A2 | 9/2000 |
| EP | 1488792 A2 | 12/2004 |
| JP | 2005-525314 A | 8/2005 |
| WO | WO 01/30381 A2 | 5/2001 |
| WO | WO 03/059395 A2 | 7/2003 |
| WO | WO 2005/005638 A2 | 1/2005 |
| WO | WO 2005/068503 A2 | 7/2005 |
| WO | WO 2005/070966 A2 | 8/2005 |
| WO | WO 2008/021290 A2 | 2/2008 |
| WO | WO 2009/026303 A1 | 2/2009 |
| WO | WO 2009/112245 A1 | 9/2009 |

OTHER PUBLICATIONS

Notification of Reasons for Rejection for Japanese Patent Application No. 2010-550081, mailed Nov. 12, 2013, including translation (7 pages).
Ashmun et al., "Monoclonal Antibodies to the Human CSF-1 Receptor (c-fms Proto-Oncogene Product) Detect Epitopes on Normal Mononuclear Phagocytes and on Human Myeloid Leukemic Blast Cells," Blood, 73(3): 827-837 (1989).
Bendig, M.; "Humanization of Rodent Antibodies by CDR Grafting"; Methods: A Companion to Methods in Enzymology; No. 8; 1995; pp. 83-93.
Colman, P.M.; "Effects of amino acid sequence changes on antibody-antigen interactions"; Research in Immunology; No. 145, 1994; pp. 33-36.
Dewar et al., "Macrophage colony-stimulating factor receptor c-fms is a novel target of imatinib," Blood, 105: 3127-3132 (2005).
Genbank Accession No. BAB22154, Version GI: 12832551, Oct. 6, 2010.
Hattersley, G. et al.; "Human Macrophage Colony-Stimulating Factor inhibits Bone Resorption by Osteoclasts Disaggregated From Rat Bone"; J. Cell. Physiol.; No. 137; 1988; pp. 199-203.
Hamilton, "Colony stimulating factors in inflammation and autoimmunity," Nature Reviews Immunology, 8: 533-544 (2008).
Hermanson, G.T., "Bioconjugate Techniques," 1st edition, Academic Press, Inc., 1996, p. 456.
Kitaura et al., "M-CSF mediates TNF-induced inflammatory osteolysis" J. Clinical Investigation, 115(12):3418-3427 (2005).
Le Meur et al., "Macrophage accumulation at a site of renal inflammation is dependent on the M-CSF/c-fms pathway," J. Leukoc. Biol., 72: 530-537 (2002).
Lin et al., "Discovery of a Cytokine and Its Receptor by Functional Screening of the Extracellular Proteome," Science, 320: 807-811 (2008).
Lugovskoy et al., "7th Annual European Antibody Congress 2011: Nov. 29-Dec. 1, 2011, Geneva, Switzerland," mAbs, 4(2), pp. 134-152 (Mar./Apr. 2012).

(Continued)

*Primary Examiner* — Hong Sang
(74) *Attorney, Agent, or Firm* — Finnegan, Henderson, Farabow, Garrett and Dunner, L.L.P.

(57) ABSTRACT

The present invention provides antibodies specific for the CSF-1R, compositions comprising said antibodies and methods of treatment using such compositions.

18 Claims, 40 Drawing Sheets

(56) References Cited

OTHER PUBLICATIONS

Paul, W.; "Fundamental Immunology"; 3rd Edition; 1993; pp. 292-295.

Roussel et al., "Mouse NIH 3T3 cells expressing human colony-stimulating factor 1 (CSF-1) receptors overgrow in serum-free medium containing human CSF-1 as their only growth factor," PNAS USA, 86: 7924-7927 (1989).

Rudikoff, S. et al.; "Single amino acid substitution altering antigen-binding specificity"; Proc. Natl. Acad. Sci. USA; vol. 79, No. 6; Mar. 1982; pp. 1979-1983.

Sherr, "Colony-Stimulating Factor-1 Receptor," Blood, 75(1): 1-12 (1990).

Sherr et al., "Inhibition of Colony-Stimulating Factor-1 Activity by Monoclonal Antibodies to the Human CSF-1 Receptor," Blood, 73(7): 1786-1793 (1989).

Toh et al., "Colony Stimulating Factor 1 Receptor Inhibition Has Anti-Inflammatory and Potent Early Onset Bone and Cartilage Protective Effects" (Abstract), Arthritis Rheum, 63 Suppl. 10: 1140 (2011).

International Search Report and Written Opinion mailed Sep. 9, 2009, for Application No. PCT/EP2009/001733, filed Mar. 11, 2009 (18 pages).

Examiner's first report on Australian Patent Application No. 2009224955, mailed Jul. 12, 2011 (4 pages).

First Office Action for Chinese Application No. 200980108967.9, mailed Oct. 15, 2012, including translation (15 pages).

Communication pursuant to Article 94(3) EPC, mailed Dec. 19, 2012, for EP Application No. 09 719 048.2 (5 pages).

Office Action dated Nov. 28, 2012 issued in Russian Patent Application No. 2010141584.

International Search Report for Application No. PCT/EP2012/052043, mailed Jul. 19, 2012 (5 pages).

```
                  SfiI
         GGCCCAGCCGGCCCAGTGACAGACACAGACATAGAACATTCACGATGTACTTGGGACTGA  60
                                                      M  Y  L  G  L  N
         ACTATGTATTCATAGTTTTTCTCCTAAATGGTGTCCAGAGTGAAGTGAAGCTTGAGGAGT 120
          Y  V  F  I  V  F  L  L  N  G  V  Q  S  E  V  K  L  E  E  S
         CTGGAGGAGGCTTGGTGCAGCCTGGAGGATCCATGAAACTCTCTTGTGCTGCCTCTGGAT 180
            G  G  G  L  V  Q  P  G  G  S  M  K  L  S  C  A  A  S  G  F
         TCACTTTTAGTGACGCCTGGATGGACTGGGTCCGCCAGTCTCCAGAGATGGGACTTGAGT 240
              T  F  S  D  A  W  M  D  W  V  R  Q  S  P  E  M  G  L  E  W
         GGGTTGCTGAAATTAGAAGCAAAGCTAATAATCATGCAACATTCTATGCTGAGTCTGTGA 300
              V  A  E  I  R  S  K  A  N  N  H  A  T  F  Y  A  E  S  V  K
         AAGGGAGGTTCACCATCTCAAGAGATGATTCCAAAAGTAGTGTCTACCTGCAAATGAACA 360
              G  R  F  T  I  S  R  D  D  S  K  S  S  V  Y  L  Q  M  N  S
         GCTTAAGACCTGAAGACACTGGCATTTATTACTGTACCAGGGTAAAGGTAGGCTTTGACA 420
              L  R  P  E  D  T  G  I  Y  Y  C  T  R  V  K  V  G  F  D  N
         ACTGGGGCCAAGGCACCACTCTCACAGTCTCCTCAGCCAAAACAACAGCCCCATCGGTCT 480
              W  G  Q  G  T  T  L  T  V  S  S  A  K  T  T  A  P  S  V  Y
         ATCCACTGGCCCCTGTGTGTGGAGATACAACTGGCTCCTCGGTGACTCTAGGATGCCTGG 540
           P  L  A  P  V  C  G  D  T  T  G  S  S  V  T  L  G  C  L  V
         TCAAGGGTTATTTCCCTGAGCCAGTGACCTTGACCTGGAACTCTGGATCCCTGTCCAGTG 600
           K  G  Y  F  P  E  P  V  T  L  T  W  N  S  G  S  L  S  S  G
         GTGTGCACACCTTCCCAGCTGTCCTGCAGTCTGACCTCTACACCCTCAGCAGCTCAGTGA 660
           V  H  T  F  P  A  V  L  Q  S  D  L  Y  T  L  S  S  S  V  T
                XhoI
         CTGTAACCTCGAGCACCTGGCCCAGCCAGTCCATCACCTGCAATGTGGCCCACCCGGCAA 720
           V  T  S  S  T  W  P  S  Q  S  I  T  C  N  V  A  H  P  A  S
         GCAGCACCAAGGTGGACAAGAAAATTGAGCCCAGAGGGCCCACAATCAAGCCCTGTCCTC 780
           S  T  K  V  D  K  K  I  E  P  R  G  P  T  I  K  P  C  P  P
         CATGCAAATGCCCAGCACCTAACCTCTTGGGTGGACCATCCGTCTTCATCTTCCCTCCAA 840
           C  K  C  P  A  P  N  L  L  G  G  P  S  V  F  I  F  P  P  K
         AGATCAAGGATGTACTCATGATCTCCCTGAGCCCCATAGTCACATGTGTGGTGGTGGATG 900
           I  K  D  V  L  M  I  S  L  S  P  I  V  T  C  V  V  V  D  V
         TGAGCGAGGATGACCCAGATGTCCAGATCAGCTGGTTTGTGAACAACGTGGAAGTACACA 960
           S  E  D  D  P  D  V  Q  I  S  W  F  V  N  N  V  E  V  H  T
         CAGCTCAGACACAAACCCATAGAGAGGATTACAACAGTACTCTCCGGGTGGTCAGTGCCC 1020
           A  Q  T  Q  T  H  R  E  D  Y  N  S  T  L  R  V  V  S  A  L
         TCCCCATCCAGCACCAGGACTGGATGAGTGGCAAGGAGTTCAAATGCAAGGTCAACAACA 1080
           P  I  Q  H  Q  D  W  M  S  G  K  E  F  K  C  K  V  N  N
         AAGACCTCCCAGCGCCCATCGAGAGAACCATCTCAAAACCCAAAGGGTCAGTAAGAGCTC 1140
           K  D  L  P  A  P  I  E  R  T  I  S  K  P  K  G  S  V  R  A  P
         CACAGGTATATGTCTTGCCTCCACCAGAAGAAGAGATGACTAAGAAACAGGTCACTCTGA 1200
           Q  V  Y  V  L  P  P  P  E  E  E  M  T  K  K  Q  V  T  L  T
         CCTGCATGGTCACAGACTTCATGCCTGAAGACATTTACGTGGAGTGGACCAACAACGGGA 1260
           C  M  V  T  D  F  M  P  E  D  I  Y  V  E  W  T  N  N  G  K
         AAACAGAGCTAAACTACAAGAACACTGAACCAGTCCTGGACTCTGATGGTTCTTACTTCA 1320
           T  E  L  N  Y  K  N  T  E  P  V  L  D  S  D  G  S  Y  F  M
         TGTACAGCAAGCTGAGAGTGGAAAAGAAGAACTGGGTGGAAAGAAATAGCTACTCCTGTT 1380
           Y  S  K  L  R  V  E  K  K  N  W  V  E  R  N  S  Y  S  C  S
         CAGTGGTCCACGAGGGTCTGCACAATCACCACACGACTAAGAGCTTCTCCCGGACTCCGG 1440
           V  V  H  E  G  L  H  N  H  H  T  T  K  S  F  S  R  T  P  G
                                                                 NotI
         GTAAATGAGCTCAGCACCCACAAAACTCTCAGGTCCAAAGAGACACCCACGCGGCCGC  1498
           K  *
```

Fig. 6

```
    SfiI
GGCCCAGCCGGCCGGAGTCAGCCTCACACTGATCACACACAGACATGAGTGTGCCCACTC  60
                                           M  S  V  P  T  Q

AGGTCCTGGGGTTGCTGCTGCTGTGGCTTACAGATGCCAGATGTGACATCCAGATGACTC 120
 V  L  G  L  L  L  L  W  L  T  D  A  R  C  D  I  Q  M  T  Q

AGTCTCCAGCCTCCCTATCTGTATCTGTGGGAGAAACTGTCACCATCACATGTCGAGCAA 180
 S  P  A  S  L  S  V  S  V  G  E  T  V  T  I  T  C  R  A  S

GTGAGAATATTTACAGTAATTTAGCATGGTATCAGCAGAAACAGGGAAAATCTCCTCAGC 240
 E  N  I  Y  S  N  L  A  W  Y  Q  Q  K  Q  G  K  S  P  Q  L

TCCTGGTCCATGCTGCAACAAACTTAGCAGATGGTGTGCCATCAAGGTTCAGTGGCAGTG 300
 L  V  H  A  A  T  N  L  A  D  G  V  P  S  R  F  S  G  S  G

GATCAGGCACACAGTATTCCCTCAAGATCAACAGCCTGCAGTCTGAAGATTTTGGGAGTT 360
 S  G  T  Q  Y  S  L  K  I  N  S  L  Q  S  E  D  F  G  S  Y

ATTACTGTCAACATTTTTGGGGTACTCCTCGGACGTTCGGTGGAGGCACCAAGTTGGAAA 420
 Y  C  Q  H  F  W  G  T  P  R  T  F  G  G  G  T  K  L  E  I

TCAAACGGGCTGATGCTGCACCAACTGTATCCATCTTCCCACCATCCAGTGAGCAGTTAA 480
 K  R  A  D  A  A  P  T  V  S  I  F  P  P  S  S  E  Q  L  T

CATCTGGAGGTGCCTCAGTCGTGTGCTTCTTGAACAACTTCTACCCCAAAGACATCAATG 540
 S  G  G  A  S  V  V  C  F  L  N  N  F  Y  P  K  D  I  N  V

TCAAGTGGAAGATTGATGGCAGTGAACGACAAAATGGCGTCCTGAACAGTTGGACTGATC 600
 K  W  K  I  D  G  S  E  R  Q  N  G  V  L  N  S  W  T  D  Q

AGGACAGCAAAGACAGCACCTACAGCATGAGCAGCACCCTCACGTTGACCAAGGACGAGT 660
 D  S  K  D  S  T  Y  S  M  S  S  T  L  T  L  T  K  D  E  Y

ATGAACGACATAACAGCTATACCTGTGAGGCCACTCACAAGACATCAACTTCACCCATTG 720
 E  R  H  N  S  Y  T  C  E  A  T  H  K  T  S  T  S  P  I  V

TCAAGAGCTTCAACAGGAATGAGTGTTAGAGACAAAGGTCCTGAGACGCCACCACCAGCT 788
 K  S  F  N  R  N  E  C  *

NotI
GCGGCCGC 788
```

Fig. 7 pTG17753

| | | Substituted amino acids[a] in VL CXIIG | | | | | | | | | | | | | | | | | | | |
|---|---|---|---|---|---|---|---|---|---|---|---|---|---|---|---|---|---|---|---|---|---|
| K1 | pTG17896 | A9S | V13A | E17D | T18R | Q40P | S43A | Q45K | V48L | H49Y | N53R | A55E | D56S | Q70D | S72T | K74T | N76S | S80P | G84A | S85T | G100Q |
| K2 | pTG17897 | A9S | V13A | E17D | T18R | | S43A | Q45K | V48L | H49Y | N53R | A55E | D56S | Q70D | S72T | K74T | N76S | | G84A | S85T | G100Q |
| K3 | pTG17899 | A9S | V13A | E17D | T18R | | S43A | Q45K | V48L | | | A55E | D56S | Q70D | S72T | K74T | N76S | | G84A | S85T | G100Q |
| K4 | pTG17900 | A9S | | E17D | T18R | | S43A | Q45K | | H49Y | N53R | A55E | D56S | Q70D | S72T | K74T | N76S | | | S85T | G100Q |
| K5 | pTG17901 | A9S | | E17D | T18R | Q40P | S43A | Q45K | | | | A55E | D56S | Q70D | S72T | K74T | N76S | S80P | | S85T | G100Q |
| K6 | pTG17902 | A9S | | E17D | T18R | | S43A | Q45K | | | | A55E | D56S | Q70D | S72T | K74T | N76S | | | S85T | G100Q |
| K7 | pTG17903 | A9S | | E17D | T18R | | S43A | Q45K | | | | | D56S | Q70D | | | N76S | | | | G100Q |
| K8 | pTG17904 | | | E17D | | | | | | | | | | | | | | | | | G100Q |
| K9 | pTG17905 | A9S | V13A | E17D | T18R | | S43A | Q45K | V48L | | | | D56S | Q70D | S72T | K74T | N76S | | G84A | S85T | G100Q |
| K10 | pTG17906 | A9S | | E17D | T18R | Q40P | S43A | Q45K | | | | | D56S | Q70D | S72T | K74T | N76S | S80P | | S85T | G100Q |
| K11 | pTG17907 | A9S | | E17D | T18R | | S43A | Q45K | | | | | D56S | Q70D | S72T | K74T | N76S | | | S85T | G100Q |
| K12 | pTG17947 | A9S | V13A | E17D | T18R | Q40D | | | | | | | | | | K74T | N76S | S80P | | | |
| K13 | pTG17948 | A9S | V13A | E17D | T18R | Q40D | S43A | Q45K | V48L | | | | D56S | Q70D | S72T | K74T | N76S | S80P | G84A | S85T | G100Q |
| K14 | pTG17949 | A9S | V13A | E17D | T18R | Q40P | | | | | | | | | | K74T | N76S | S80P | | | |
| K15 | pTG17950 | A9S | V13A | E17D | T18R | Q40P | S43A | Q45K | V48L | | | | D56S | Q70D | S72T | K74T | N76S | S80P | G84A | S85T | G100Q |

[a]amino acids in bold have a relative side-chain solvent-accessibility above 50 %, underlined above 25%

Fig. 15

| | | Substituted amino acids* in VH CXIIG6 | | | | | | | | | | | | | | | | | | |
|---|---|---|---|---|---|---|---|---|---|---|---|---|---|---|---|---|---|---|---|---|
| H1 | pIG17870 | K3Q | E5V | M18L | K19R | S40A | E42G | M43K | A49G | E50R | F61E | E64A | S79N | V81L | R89K | P90T | G94A | I95V | T113L | L114V |
| H2 | pIG17871 | K3Q | E5V | M18L | K19R | S40A | E42G | M43K | A49G | E50R | F61E | E64A | S79N | V81L | R89K | P90T | G94A | I95V | T113L | |
| H3 | pIG17872 | K3Q | E5V | M18L | K19R | S40A | E42G | M43K | A49G | E50R | F61E | E64A | S79N | V81L | R89K | P90T | | | | L114V |
| H4 | pIG17873 | K3Q | E5V | M18L | K19R | S40A | E42G | M43K | A49G | E50R | | E64A | S79N | V81L | R89K | | G94A | I95V | T113L | L114V |
| H5 | pIG17874 | K3Q | E5V | M18L | K19R | S40A | E42G | M43K | A49G | E50R | | E64A | S79N | V81L | R89K | | G94A | I95V | T113L | L114V |
| H6 | pIG17875 | K3Q | E5V | M18L | K19R | S40A | E42G | M43K | A49G | E50R | | E64A | S79N | V81L | R89K | | G94A | I95V | T113L | |
| H7 | pIG17883 | K3Q | E5V | | K19R | S40A | E42G | M43K | | | | E64A | S79N | V81L | R89K | | | I95V | | L114V |
| H8 | pIG17884 | K3Q | E5V | | K19R | S40A | E42G | M43K | | | | E64A | S79N | | R89K | | | | T113L | L114V |
| H9 | pIG17885 | K3Q | E5V | | K19R | S40A | E42G | M43K | | | | E64A | S79N | | R89K | | | I95V | T113L | |
| H10 | pIG17886 | K3Q | E5V | | K19R | | E42G | M43K | | | | E64A | | | R89K | | | | | L114V |
| H11 | pIG17887 | K3Q | E5V | | K19R | | E42G | M43K | | | | E64A | | | R89K | | | | T113L | L114V |
| H12 | pIG17888 | K3Q | E5V | | K19R | | E42G | M43K | | | | E64A | | | R89K | | | | T113L | |
| H13 | pIG17889 | | | | K19R | | | | | | | | | | R89K | | | | | L114V |
| H14 | pIG17890 | | | | K19R | | | | | | | | | | R89K | | | | | L114V |
| H15 | pIG17891 | | | | K19R | | | | | | | | | | R89K | | | | | |
| H16 | pIG17892 | K3Q | E5V | M18L | K19R | S40A | E42G | M43K | A49G | | | E64A | S79N | V81L | R89K | | G94A | I95V | T113L | L114V |
| H17 | pIG17893 | K3Q | E5V | M18L | K19R | S40A | E42G | M43K | A49G | | | E64A | S79N | V81L | R89K | | G94A | I95V | T113L | L114V |
| H18 | pIG17894 | K3Q | E5V | M18L | | S40A | E42G | M43K | A49G | | | E64A | S79N | V81L | R89K | | G94A | I95V | | |
| H19 | pIG17943 | K3Q | E5V | M18L | | | E42G | M43K | A49G | | | E64A | | | | P90A | | | | |
| H20 | pIG17944 | K3Q | E5V | M18L | K19R | | E42G | M43K | | | | E64A | | | R89K | | | | T113L | L114V |
| H21 | pIG17945 | K3Q | E5V | M18L | K19R | | E42G | M43K | | | | | | | R89K | P90A | | | T113L | L114V |
| H22 | pIG17946 | K3Q | E5V | M18L | K19R | S40A | E42G | M43K | | | | | | | R89K | P90A | | | T113L | L114V |
| H23 | pIG17968 | K3Q | E5V | M18L | K19R | | E42G | M43K | | | | | | | R89K | | | I95V | T113L | L114V |
| H24 | pIG17969 | K3Q | E5V | M18L | K19R | | E42G | M43K | | | | | | | R89K | P90A | | | T113L | L114V |
| H25 | pIG17970 | K3Q | E5V | M18L | K19R | S40A | E42G | M43K | | | | | | | R89K | P90A | | I95V | T113L | L114V |
| H26 | pIG17985 | K3Q | E5V | M18L | K19R | | E42G | M43K | | | | | | | R89K | P90T | | | T113L | L114V |
| H27 | pIG17986 | K3Q | E5V | M18L | K19R | S40A | E42G | M43K | | | | | | | R89K | P90T | | I95V | T113L | L114V |

*amino acids in bold have a relative side-chain solvent-accessibility above 50 %, underlined above 25%

Fig. 16

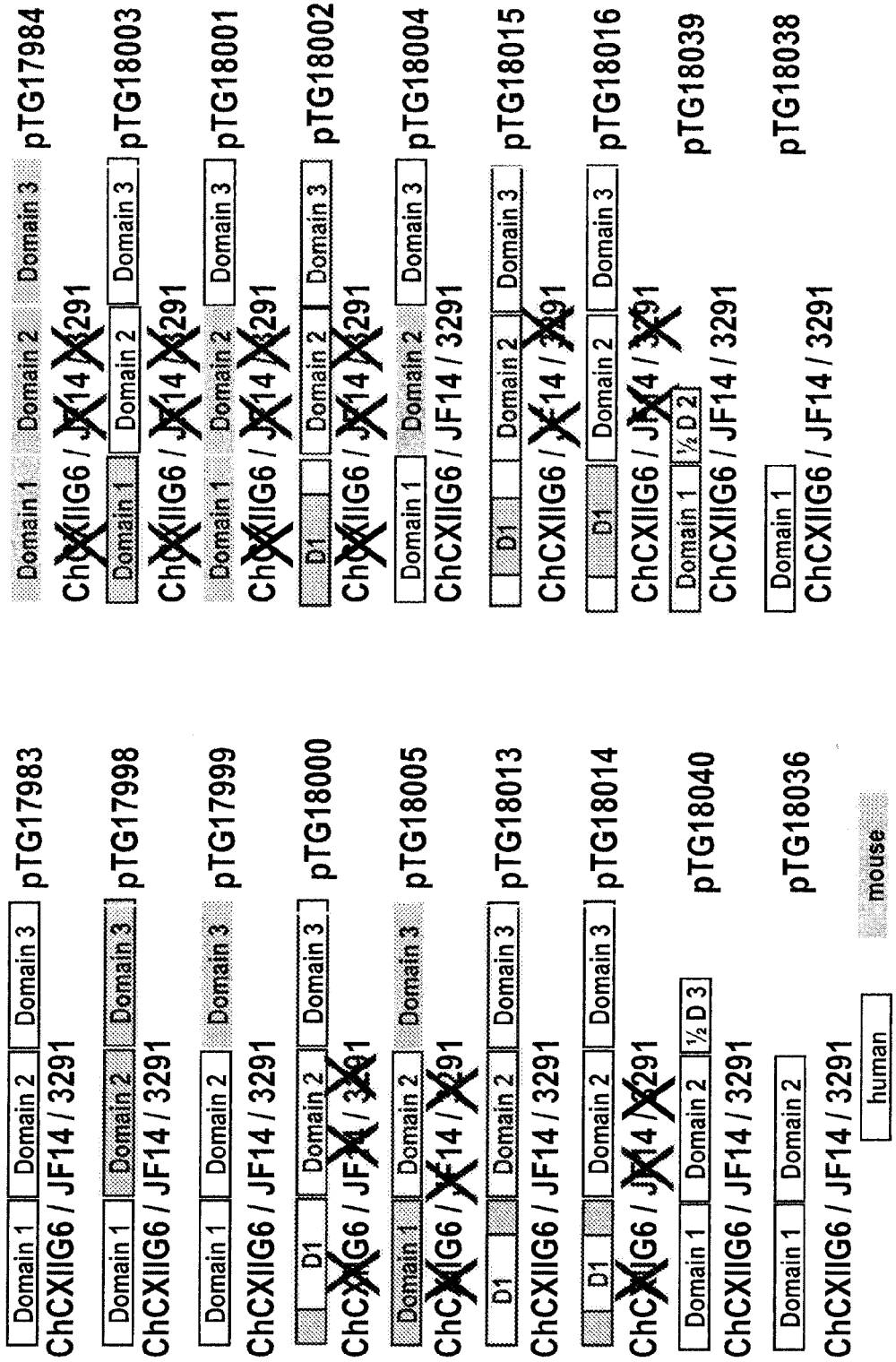
Fig. 19: epitope mapping of ChCXIIG6, JF14 and 3291

Fig. 20

Underlined in grey = CD115 mouse

Underlined in white = CD115 human

|  | Ig-like domain 1 (D1) aa 20 to 104 | Ig-like domain 2 (D2) aa 105 to 199 | Ig-like domain 3 (D3) aa 200 to 298 |
|---|---|---|---|
| pTG17983 | IPVIE...YVKDP | ARPWN...VQKVI | PGPPA...RVVES |
| pTG17984 | APVIE...YVKDP | AHSWN...VNRVH | PEPPQ...QVVES |
| pTG17998 | IPVIE...YVKDP | AHSWN...VNRVH | PEPPQ...QVVES |
| pTG17999 | IPVIE...YVKDP | ARPWN...VQKVI | PEPPQ...QVVES |
| pTG18003 | APVIE...YVKDP | ARPWN...VQKVI | PGPPA...RVVES |
| pTG18001 | APVIE...YVKDP | AHSWN...VNRVH | PGPPA...RVVES |
| pTG18005 | APVIE...YVKDP | ARPWN...VQKVI | PEPPQ...QVVES |
| pTG18004 | IPVIE...YVKDP | AHSWN...VNRVH | PGPPA...RVVES |

|  | Ig-like domain 1 (D1) aa 20 to 104 | | | Ig-like domain 2 (D2) aa 105 to 199 | Ig-like domain 3 (D3) aa 200 to 298 |
|---|---|---|---|---|---|
|  | aa20 to 41 | aa42 to 90 | aa91 to 104 | | |
| pTG18000 | APVIE...TVTLR | CVGNG...EPGDP | LGGSA...YVKDP | ARPWN...VQKVI | PGPPA...RVVES |
| pTG18002 | APVIE...TVTLR | CVSNG...ELEDP | LGGSA...YVKDP | ARPWN...VQKVI | PGPPA...RVVES |
| pTG18013 | IPVIE...TVTLR | CVGNG...EPGDP | MAGST...YVKDP | ARPWN...VQKVI | PGPPA...RVVES |
| pTG18014 | APVIE...TVTLR | CVGNG...EPGDP | MAGST...YVKDP | ARPWN...VQKVI | PGPPA...RVVES |
| pTG18015 | IPVIE...TVTLR | CVSNG...ELEDP | LGGSA...YVKDP | ARPWN...VQKVI | PGPPA...RVVES |
| pTG18016 | IPVIE...TVTLR | CVSNG...ELEDP | MAGST...YVKDP | ARPWN...VQKVI | PGPPA...RVVES |

|  | Ig-like domain 1 (D1) aa 20 to 104 | Ig-like domain 2 (D2) aa 105 to 199 | ½ Ig-like domain 3 (D3) aa 200 to 246 |
|---|---|---|---|
| pTG18040 | IPVIE...YVKDP | ARPWN...VQKVI | PGPPA...TKLAI |
| pTG18036 | IPVIE...YVKDP | ARPWN...VQKVI |  |
|  | Ig-like domain 1 (D1) aa 20 to 104 | ½ Ig-like domain 2 (D2) aa 105 to 157 |  |
| pTG18039 | IPVIE...YVKDP | ARPWN... NYSFS |  |
| pTG18038 | IPVIE...YVKDP |  |  |

**Fig. 21: Competition curve
between ¹²⁵I-H27K15 antibody and unlabeled H27K15 on EL4-CD115**
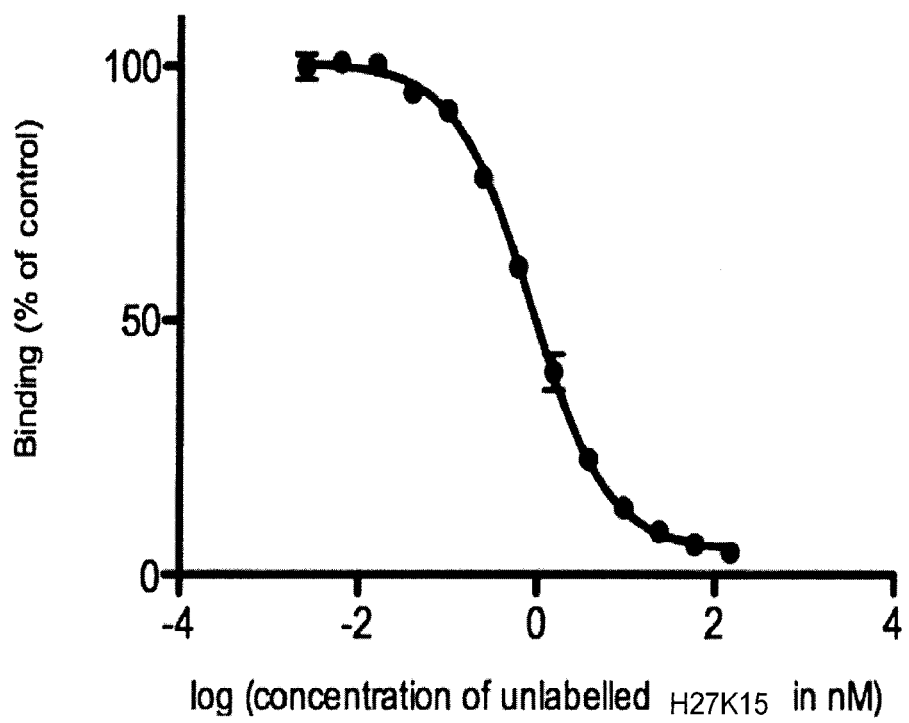

Competition curve between ¹²⁵I-H27K15 antibody and various antibodies on EL4-CD115

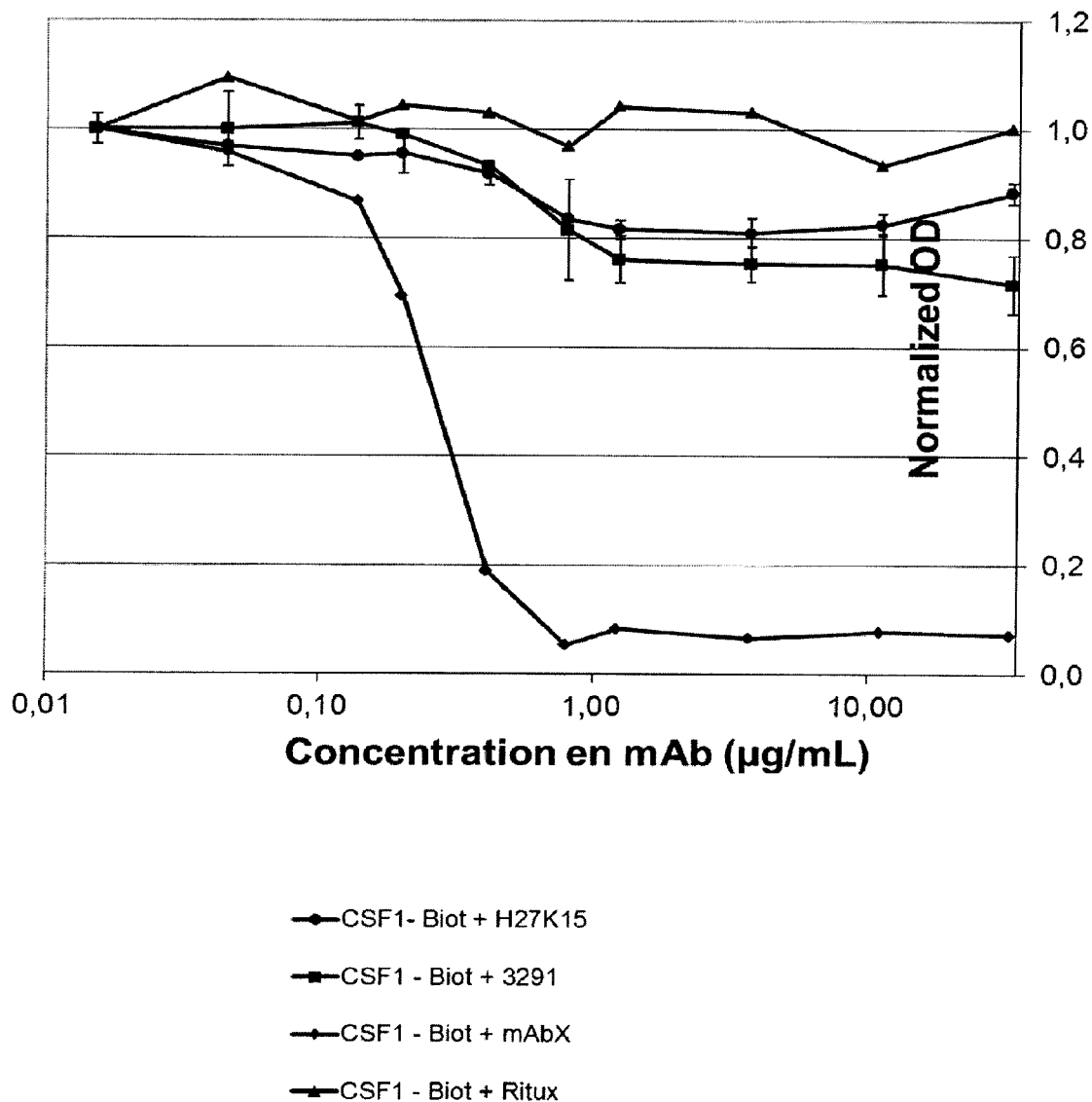

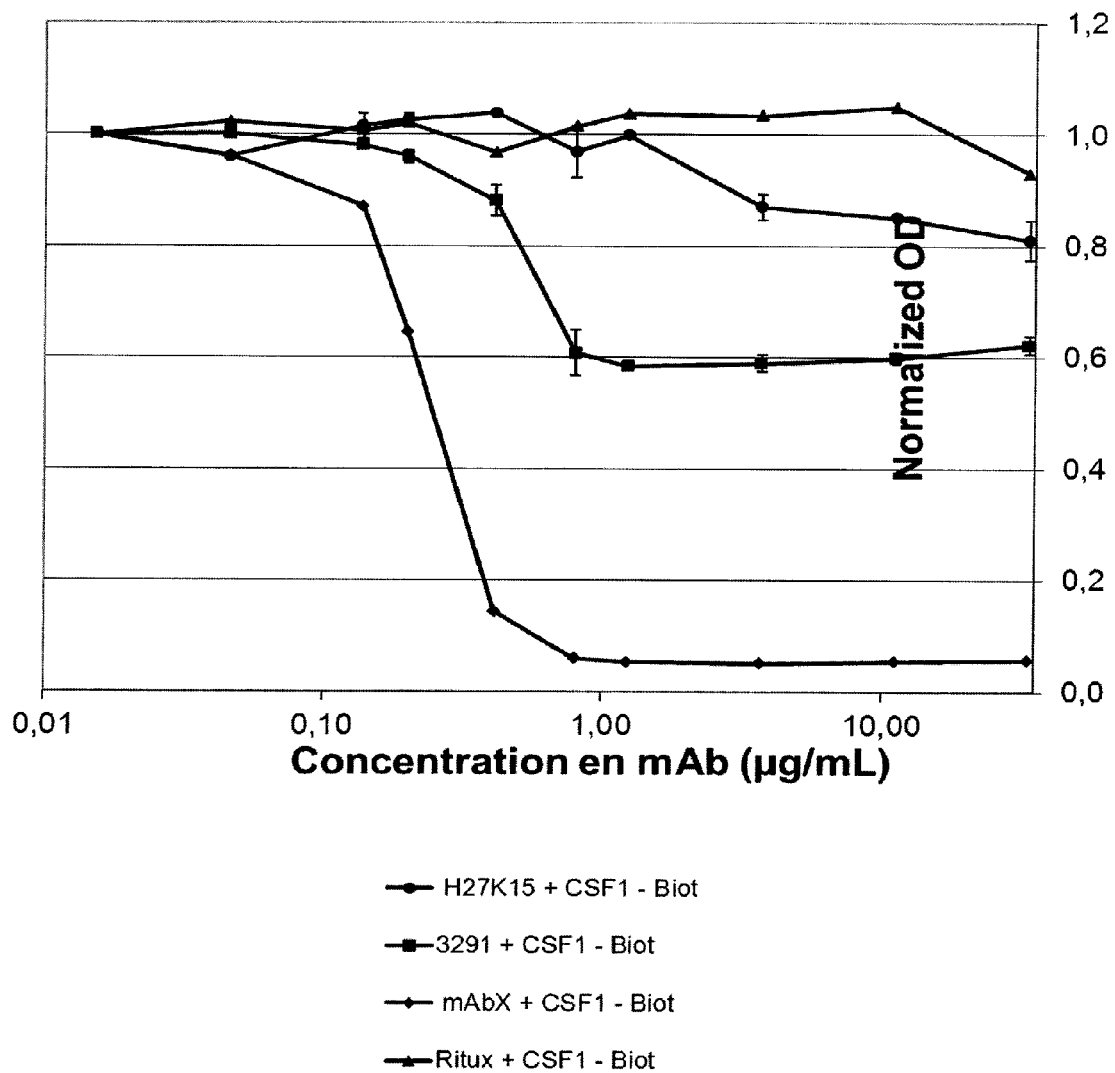
Fig. 24 :Preincubation competition:
mAb (1hour), then CSF1-biot (1hour)

Fig.25 : Coincubation competition: mAb and CSF1-biot together (1hour)
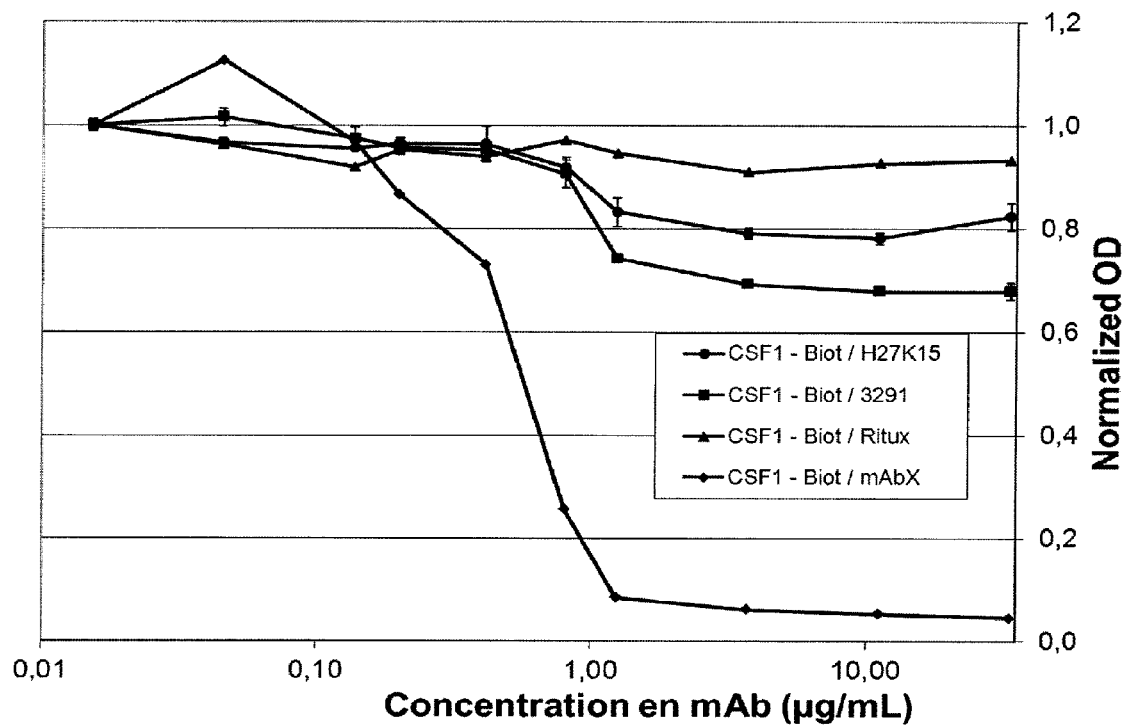

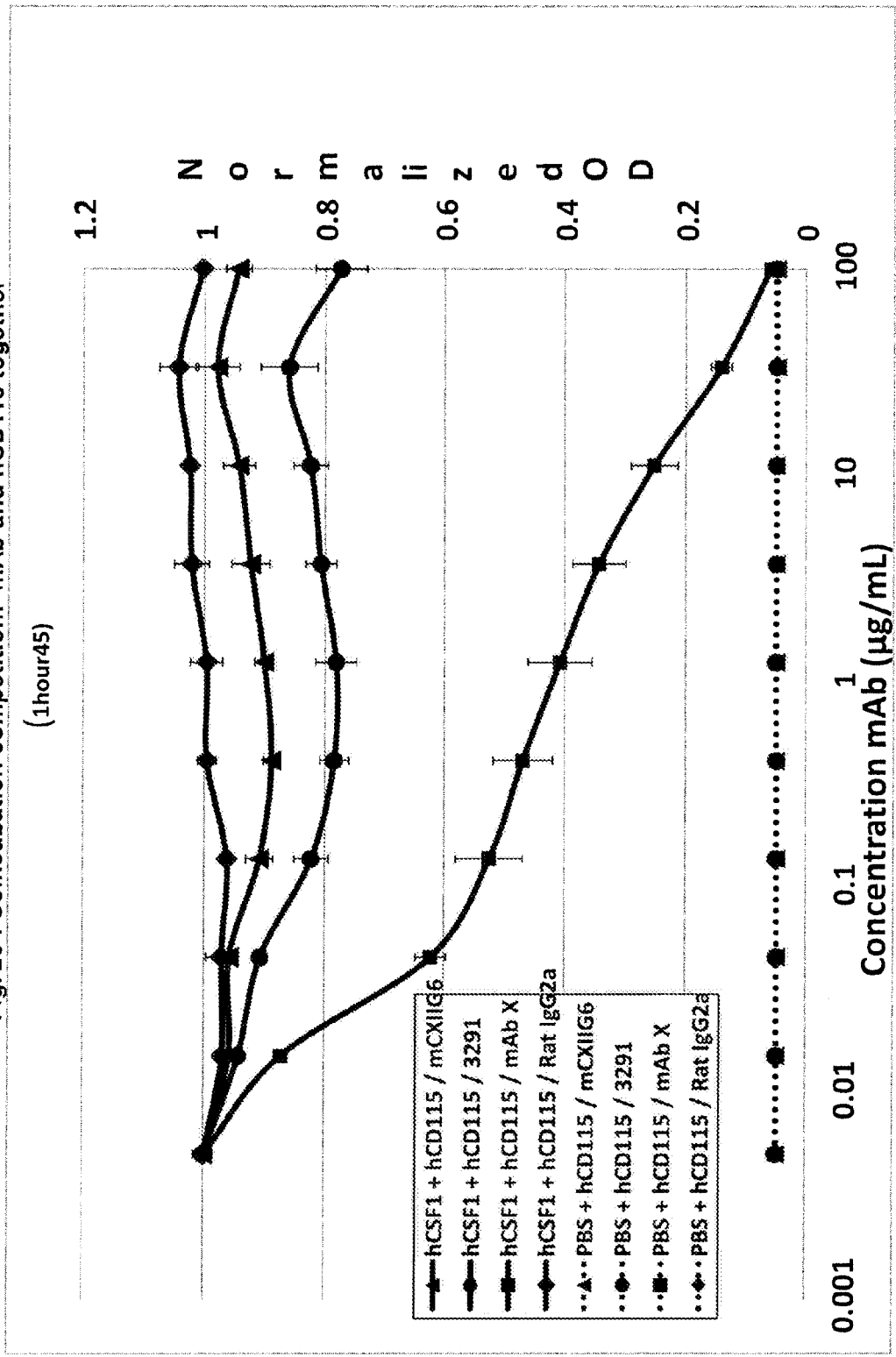
Fig. 26: Coincubation competition: mAb and hCD115 together (1hour45)

Fig. 27 : Lack of cross-reactivity of hCXIIG6 variants with tyrosine kinase receptors from type III subfamily other than CD115
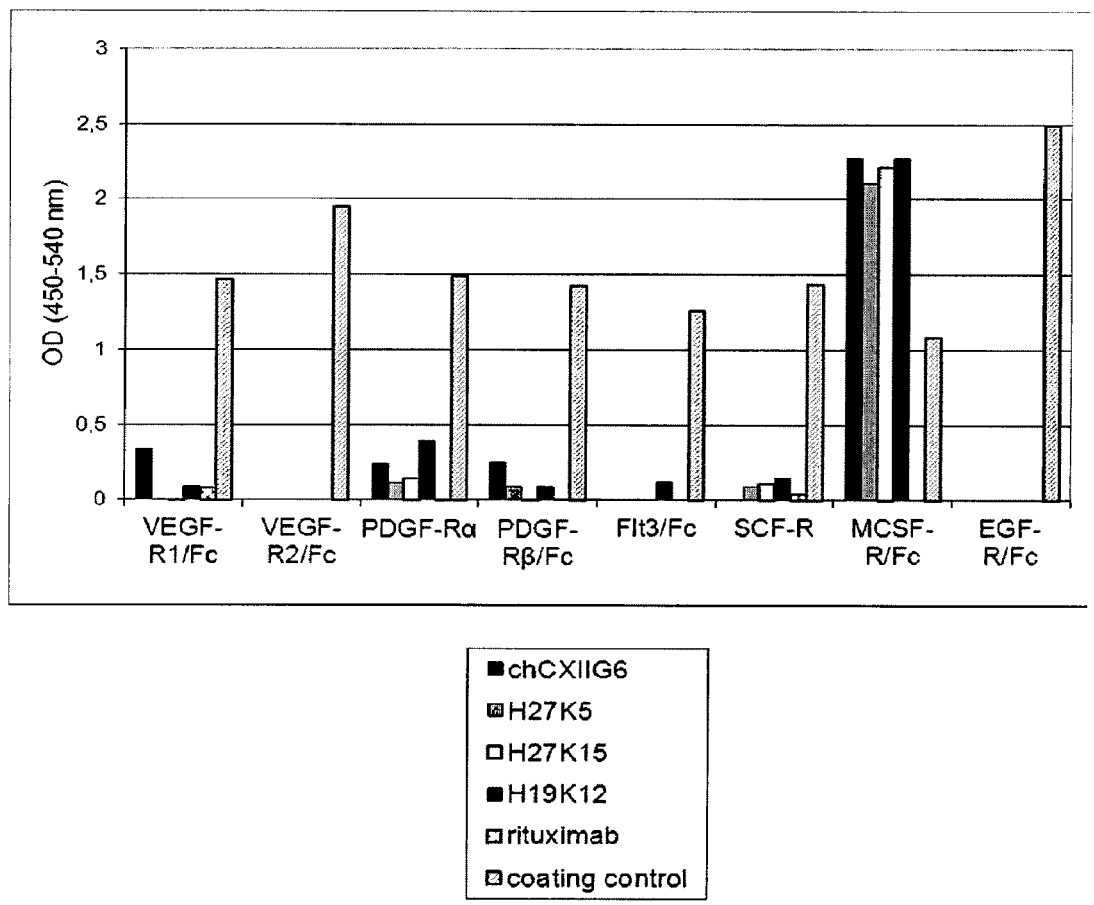
Bars correspond to values measured from single wells and are representative of 2 independent experiments.

Fig. 28 : Blockade of soluble CD115 by hCXIIG6 variants and chCXIIG6 in the M-NFS-60-cell based assay
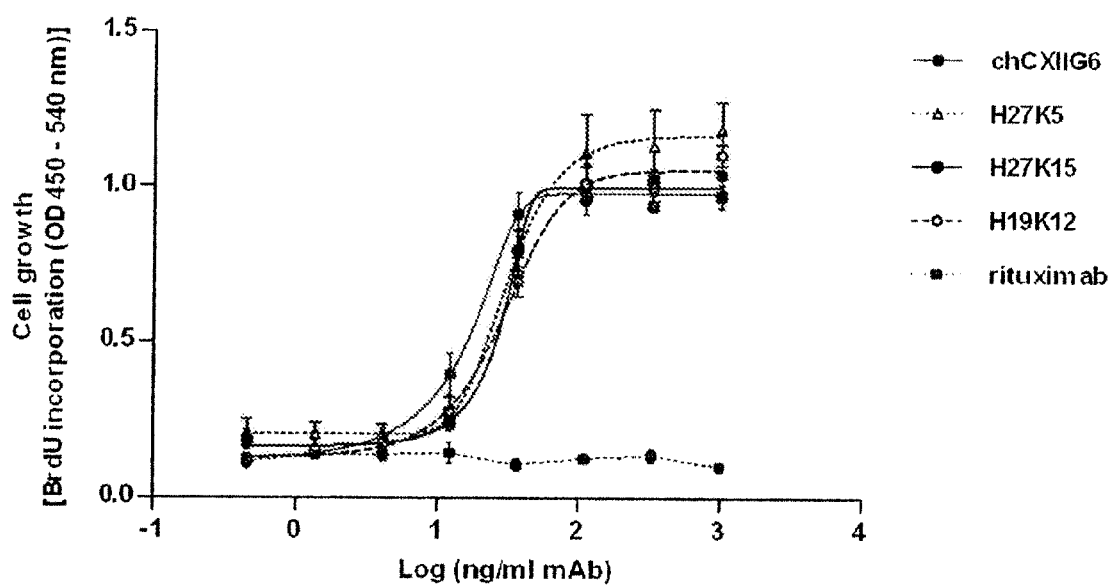

Fig. 29 : Inhibition of CSF-1-dependent proliferation of AML5 cells by hCXIIG6 variants
29A : AML5 cells express surface CD115
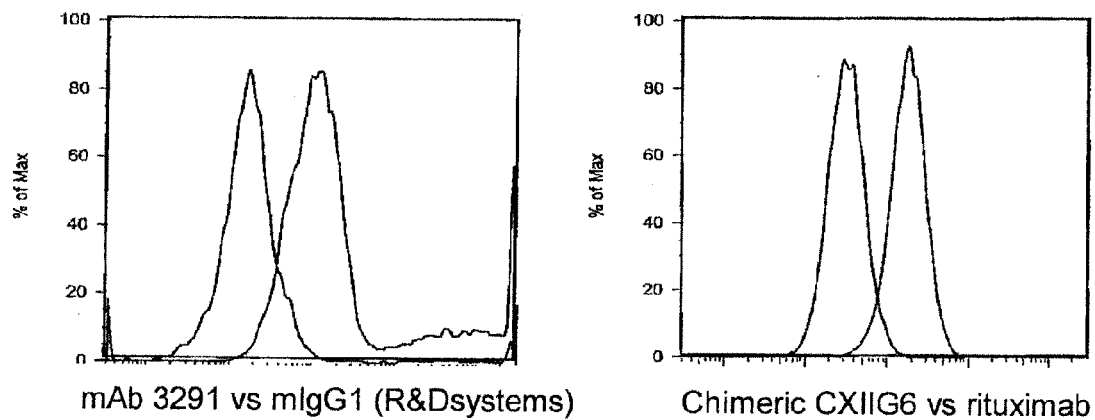
mAb 3291 vs mIgG1 (R&Dsystems)    Chimeric CXIIG6 vs rituximab
29B : AML5 cell growth is stimulated by CSF-1 in a dose-dependent fashion
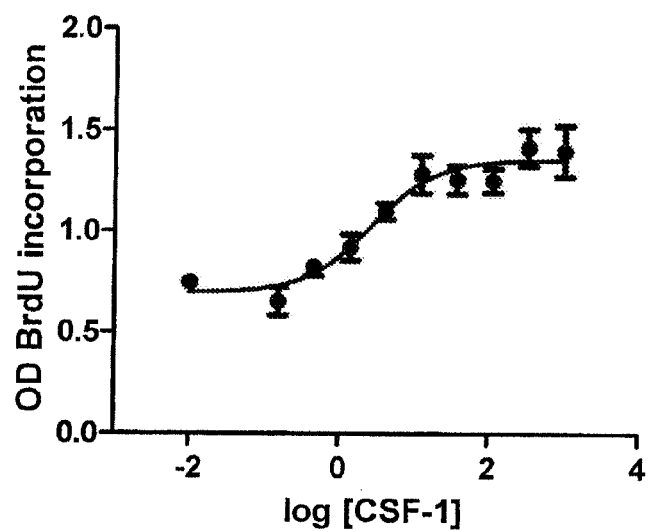

Fig. 29 : Inhibition of CSF-1-dependent proliferation of AML5 cells by hCXIIG6 variants
29C : hCXIIG6 variants and chCXIIG6 inhibit CSF-1-dependent proliferation of AML5 cells.
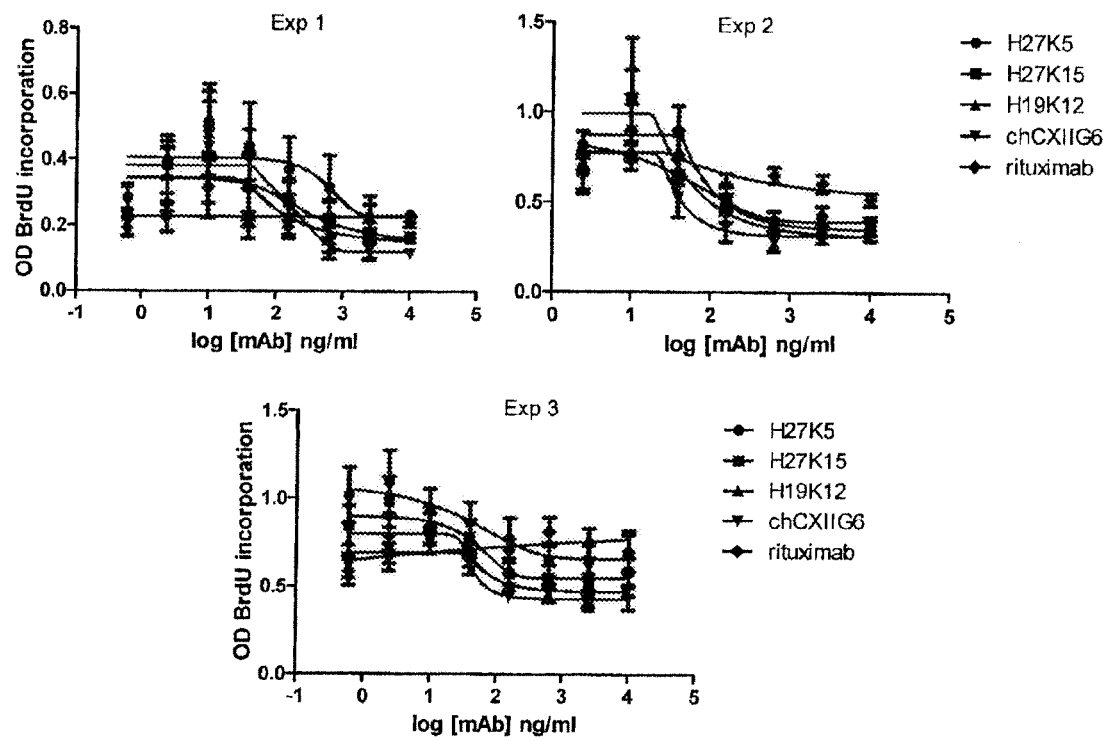
29 D : EC50 and R square values calculated by GraphPad Prism from the results shown in C
| | EC50 / R square | | | |
|---|---|---|---|---|
| | H27K5 | H27K15 | H19K12 | chCXIIG6 |
| Exp 1 | 608 / 0,19 | 188 / 0,36 | 105 / 0,23 | 217 / 0,27 |
| Exp 2 | 50 / 0,74 | 86 / 0,56 | 46 / 0,62 | 37 / 0,57 |
| Exp 3 | 40 / 0,22 | 54 / 0,34 | 48 / 0,41 | 49 / 0,44 |

Fig. 30 : ADCC activity of hCXIIG6 variants on EL4-CD115 target cells
30A
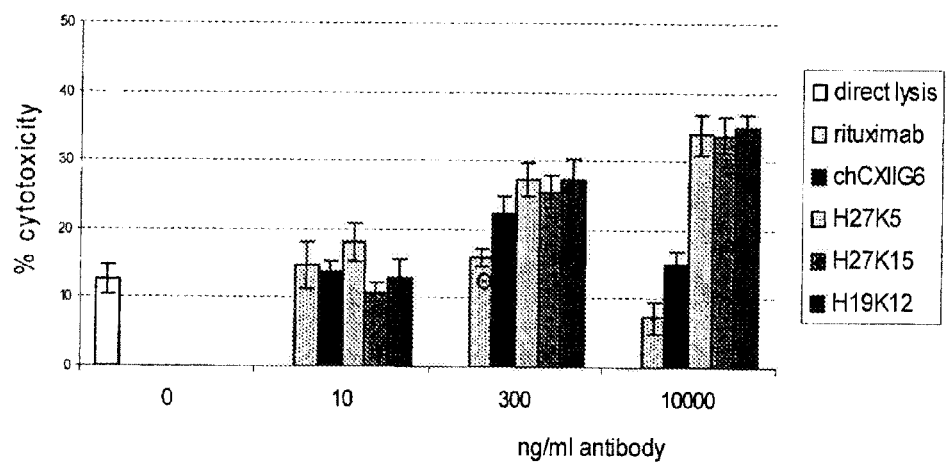
30B
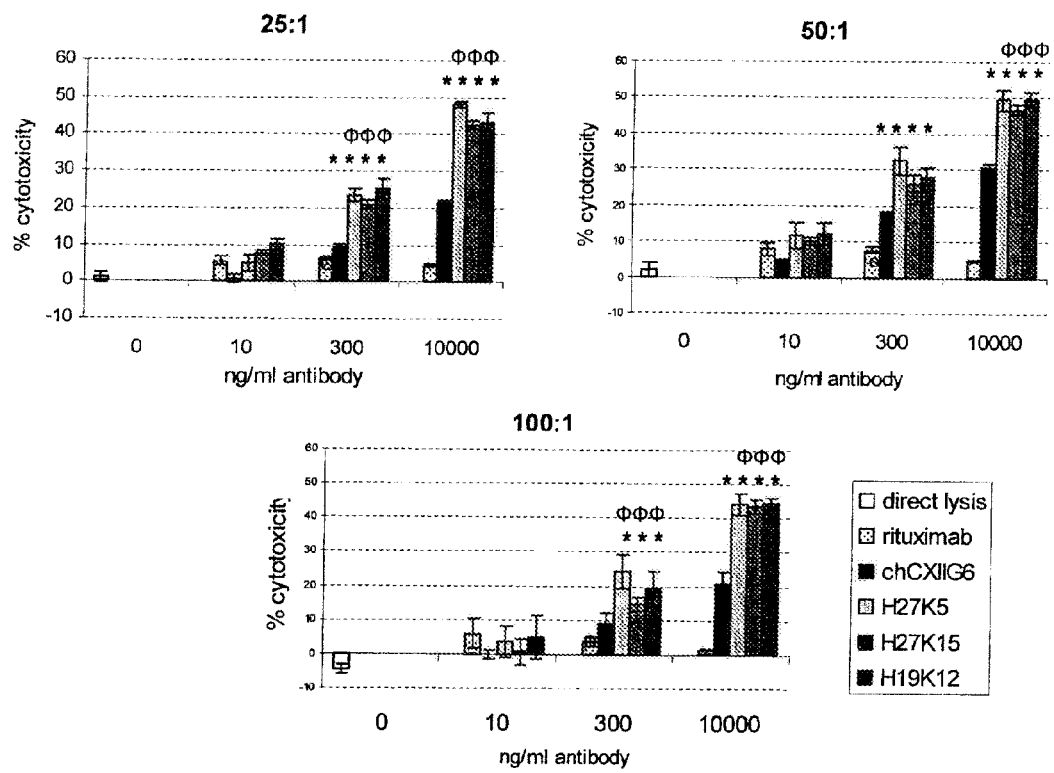

Fig. 31 : Therapeutic effect of chimeric CXIIG6 in the BeWo choriocarcinoma tumor model
31A
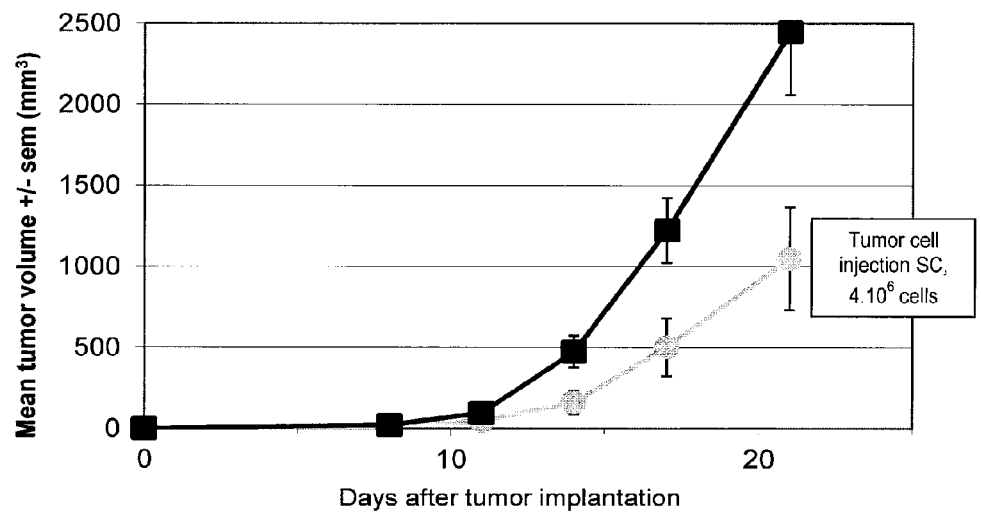
31B
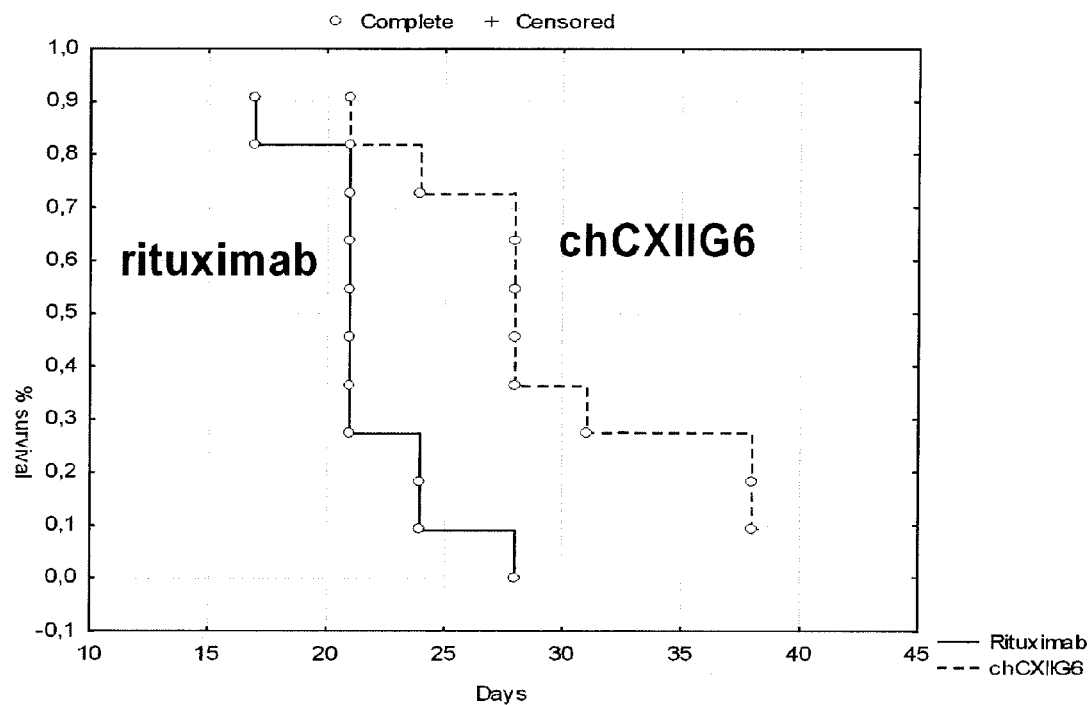

sequence "H27" –the corresponding variable region is underlined (SEQ ID NO :37)

Met Tyr Leu Gly Leu Asn Tyr Val Phe Ile Val Phe Leu Leu Asn Gly Val Gln Ser <u>Glu</u>

<u>Val Gln Leu Val Glu Ser Gly Gly Gly Leu Val Gln Pro Gly Gly Ser Leu Arg Leu Ser</u>

<u>Cys Ala Ala Ser Gly Phe Thr Phe Ser Asp Ala Trp Met Asp Trp Val Arg Gln Ala Pro</u>

<u>Gly Lys Gly Leu Glu Trp Val Ala Glu Ile Arg Ser Lys Ala Asn Asn His Ala Thr Phe</u>

<u>Tyr Ala Glu Ser Val Lys Gly Arg Phe Thr Ile Ser Arg Asp Asp Ser Lys Ser Ser Val</u>

<u>Tyr Leu Gln Met Asn Ser Leu Lys Thr Glu Asp Thr Gly Val Tyr Tyr Cys Thr Arg Val</u>

<u>Lys Val Gly Phe Asp Asn Trp Gly Gln Gly Thr Leu Val Thr Val Ser Ser</u> Ala Ser Thr

Lys Gly Pro Ser Val Phe Pro Leu Ala Pro Ser Ser Lys Ser Thr Ser Gly Gly Thr Ala

Ala Leu Gly Cys Leu Val Lys Asp Tyr Phe Pro Glu Pro Val Thr Val Ser Trp Asn Ser

Gly Ala Leu Thr Ser Gly Val His Thr Phe Pro Ala Val Leu Gln Ser Ser Gly Leu Tyr

Ser Leu Ser Ser Val Val Thr Val Pro Ser Ser Ser Leu Gly Thr Gln Thr Tyr Ile Cys

Asn Val Asn His Lys Pro Ser Asn Thr Lys Val Asp Lys Lys Val Glu Pro Lys Ser Cys

Asp Lys Thr His Thr Cys Pro Pro Cys Pro Ala Pro Glu Leu Leu Gly Gly Pro Ser Val

Phe Leu Phe Pro Pro Lys Pro Lys Asp Thr Leu Met Ile Ser Arg Thr Pro Glu Val Thr

Cys Val Val Val Asp Val Ser His Glu Asp Pro Glu Val Lys Phe Asn Trp Tyr Val Asp

Gly Val Glu Val His Asn Ala Lys Thr Lys Pro Arg Glu Glu Gln Tyr Asn Ser Thr Tyr

Arg Val Val Ser Val Leu Thr Val Leu His Gln Asp Trp Leu Asn Gly Lys Glu Tyr Lys

FIG. 32A

Cys Lys Val Ser Asn Lys Ala Leu Pro Ala Pro Ile Glu Lys Thr Ile Ser Lys
Ala Lys

Gly Gln Pro Arg Glu Pro Gln Val Tyr Thr Leu Pro Pro Ser Arg Asp Glu Leu
Thr Lys

Asn Gln Val Ser Leu Thr Cys Leu Val Lys Gly Phe Tyr Pro Ser Asp Ile Ala
Val Glu

Trp Glu Ser Asn Gly Gln Pro Glu Asn Asn Tyr Lys Thr Thr Pro Pro Val Leu
Asp Ser

Asp Gly Ser Phe Phe Leu Tyr Ser Lys Leu Thr Val Asp Lys Ser Arg Trp Gln
Gln Gly

Asn Val Phe Ser Cys Ser Val Met His Glu Ala Leu His Asn His Tyr Thr Gln
Lys Ser

Leu Ser Leu Ser Pro Gly Lys sequence "H19" –the corresponding variable region is underlined (SEQ ID NO :38)

Met Tyr Leu Gly Leu Asn Tyr Val Phe Ile Val Phe Leu Leu Asn Gly Val Gln
Ser <u>Glu</u>

<u>Val Gln Leu Val Glu Ser Gly Gly Gly Leu Val Gln Pro Gly Gly Ser Leu Lys</u>
<u>Leu Ser</u>

<u>Cys Ala Ala Ser Gly Phe Thr Phe Ser Asp Ala Trp Met Asp Trp Val Arg Gln</u>
<u>Ser Pro</u>

<u>Glu Met Gly Leu Glu Trp Val Ala Glu Ile Arg Ser Lys Ala Asn Asn His Ala</u>
<u>Thr Phe</u>

<u>Tyr Ala Glu Ser Val Lys Gly Arg Phe Thr Ile Ser Arg Asp Asp Ser Lys Ser</u>
<u>Ser Val</u>

<u>Tyr Leu Gln Met Asn Ser Leu Arg Ala Glu Asp Thr Gly Ile Tyr Tyr Cys Thr</u>
<u>Arg Val</u>

<u>Lys Val Gly Phe Asp Asn Trp Gly Gln Gly Thr Thr Leu Thr Val Ser Ser Ala</u>
Ser Thr

Lys Gly Pro Ser Val Phe Pro Leu Ala Pro Ser Ser Lys Ser Thr Ser Gly Gly
Thr Ala

Ala Leu Gly Cys Leu Val Lys Asp Tyr Phe Pro Glu Pro Val Thr Val Ser Trp
Asn Ser

Gly Ala Leu Thr Ser Gly Val His Thr Phe Pro Ala Val Leu Gln Ser Ser Gly
Leu Tyr

FIG. 32B

Ser Leu Ser Ser Val Val Thr Val Pro Ser Ser Ser Leu Gly Thr Gln Thr Tyr Ile Cys

Asn Val Asn His Lys Pro Ser Asn Thr Lys Val Asp Lys Lys Val Glu Pro Lys Ser Cys

Asp Lys Thr His Thr Cys Pro Pro Cys Pro Ala Pro Glu Leu Leu Gly Gly Pro Ser Val

Phe Leu Phe Pro Pro Lys Pro Lys Asp Thr Leu Met Ile Ser Arg Thr Pro Glu Val Thr

Cys Val Val Val Asp Val Ser His Glu Asp Pro Glu Val Lys Phe Asn Trp Tyr Val Asp

Gly Val Glu Val His Asn Ala Lys Thr Lys Pro Arg Glu Glu Gln Tyr Asn Ser Thr Tyr

Arg Val Val Ser Val Leu Thr Val Leu His Gln Asp Trp Leu Asn Gly Lys Glu Tyr Lys

Cys Lys Val Ser Asn Lys Ala Leu Pro Ala Pro Ile Glu Lys Thr Ile Ser Lys Ala Lys

Gly Gln Pro Arg Glu Pro Gln Val Tyr Thr Leu Pro Pro Ser Arg Asp Glu Leu Thr Lys

Asn Gln Val Ser Leu Thr Cys Leu Val Lys Gly Phe Tyr Pro Ser Asp Ile Ala Val Glu

Trp Glu Ser Asn Gly Gln Pro Glu Asn Asn Tyr Lys Thr Thr Pro Pro Val Leu Asp Ser

Asp Gly Ser Phe Phe Leu Tyr Ser Lys Leu Thr Val Asp Lys Ser Arg Trp Gln Gln Gly

Asn Val Phe Ser Cys Ser Val Met His Glu Ala Leu His Asn His Tyr Thr Gln Lys Ser

Leu Ser Leu Ser Pro Gly Lys

Sequence "K5" – the corresponding variable region is underlined (SEQ ID NO :39)

Met Ser Val Pro Thr Gln Val Leu Gly Leu Leu Leu Leu Trp Leu Thr Asp Ala Arg Cys

<u>Asp Ile Gln Met Thr Gln Ser Pro Ser Ser Leu Ser Val Ser Val Gly Asp Arg Val Thr</u>

<u>Ile Thr Cys Arg Ala Ser Glu Asn Ile Tyr Ser Asn Leu Ala Trp Tyr Gln Gln Lys Pro</u>

FIG. 32C

Gly Lys Ala Pro Lys Leu Leu Val His Ala Ala Thr Asn Leu Glu Ser Gly Val
Pro Ser

Arg Phe Ser Gly Ser Gly Ser Gly Thr Asp Tyr Thr Leu Thr Ile Ser Ser Leu
Gln Pro

Glu Asp Phe Gly Thr Tyr Tyr Cys Gln His Phe Trp Gly Thr Pro Arg Thr Phe
Gly Gln

Gly Thr Lys Leu Glu Ile Lys Arg Thr Val Ala Ala Pro Ser Val Phe Ile Phe
Pro Pro

Ser Asp Glu Gln Leu Lys Ser Gly Thr Ala Ser Val Val Cys Leu Leu Asn Asn
Phe Tyr

Pro Arg Glu Ala Lys Val Gln Trp Lys Val Asp Asn Ala Leu Gln Ser Gly Asn
Ser Gln

Glu Ser Val Thr Glu Gln Asp Ser Lys Asp Ser Thr Tyr Ser Leu Ser Ser Thr
Leu Thr

Leu Ser Lys Ala Asp Tyr Glu Lys His Lys Val Tyr Ala Cys Glu Val Thr His
Gln Gly

Leu Ser Ser Pro Val Thr Lys Ser Phe Asn Arg Gly Glu Cys

Sequence "K12" —the corresponding variable region is underlined (SEQ ID NO :40)

Met Ser Val Pro Thr Gln Val Leu Gly Leu Leu Leu Leu Trp Leu Thr Asp Ala
Arg Cys

Asp Ile Gln Met Thr Gln Ser Pro Ser Ser Leu Ser Ala Ser Val Gly Asp Arg
Val Thr

Ile Thr Cys Arg Ala Ser Glu Asn Ile Tyr Ser Asn Leu Ala Trp Tyr Gln Gln
Lys Asp

Gly Lys Ser Pro Gln Leu Leu Val His Ala Ala Thr Asn Leu Ala Asp Gly Val
Pro Ser

Arg Phe Ser Gly Ser Gly Ser Gly Thr Gln Tyr Ser Leu Thr Ile Ser Ser Leu
Gln Pro

Glu Asp Phe Gly Ser Tyr Tyr Cys Gln His Phe Trp Gly Thr Pro Arg Thr Phe
Gly Gly

Gly Thr Lys Leu Glu Ile Lys Arg Thr Val Ala Ala Pro Ser Val Phe Ile Phe
Pro Pro

Ser Asp Glu Gln Leu Lys Ser Gly Thr Ala Ser Val Val Cys Leu Leu Asn Asn
Phe Tyr

FIG. 32D

Pro Arg Glu Ala Lys Val Gln Trp Lys Val Asp Asn Ala Leu Gln Ser Gly Asn Ser Gln

Glu Ser Val Thr Glu Gln Asp Ser Lys Asp Ser Thr Tyr Ser Leu Ser Ser Thr Leu Thr

Leu Ser Lys Ala Asp Tyr Glu Lys His Lys Val Tyr Ala Cys Glu Val Thr His Gln Gly

Leu Ser Ser Pro Val Thr Lys Ser Phe Asn Arg Gly Glu Cys

Sequence "K15" –the corresponding variable region is underlined (SEQ ID NO :41)

Met Ser Val Pro Thr Gln Val Leu Gly Leu Leu Leu Leu Trp Leu Thr Asp Ala Arg Cys

Asp Ile Gln Met Thr Gln Ser Pro Ser Ser Leu Ser Ala Ser Val Gly Asp Arg Val Thr

Ile Thr Cys Arg Ala Ser Glu Asn Ile Tyr Ser Asn Leu Ala Trp Tyr Gln Gln Lys Pro

Gly Lys Ala Pro Lys Leu Leu Leu His Ala Ala Thr Asn Leu Ala Ser Gly Val Pro Ser

Arg Phe Ser Gly Ser Gly Ser Gly Thr Asp Tyr Thr Leu Thr Ile Ser Ser Leu Gln Pro

Glu Asp Phe Ala Thr Tyr Tyr Cys Gln His Phe Trp Gly Thr Pro Arg Thr Phe Gly Gln

Gly Thr Lys Leu Glu Ile Lys Arg Thr Val Ala Ala Pro Ser Val Phe Ile Phe Pro Pro

Ser Asp Glu Gln Leu Lys Ser Gly Thr Ala Ser Val Val Cys Leu Leu Asn Asn Phe Tyr

Pro Arg Glu Ala Lys Val Gln Trp Lys Val Asp Asn Ala Leu Gln Ser Gly Asn Ser Gln

Glu Ser Val Thr Glu Gln Asp Ser Lys Asp Ser Thr Tyr Ser Leu Ser Ser Thr Leu Thr

Leu Ser Lys Ala Asp Tyr Glu Lys His Lys Val Tyr Ala Cys Glu Val Thr His Gln Gly

Leu Ser Ser Pro Val Thr Lys Ser Phe Asn Arg Gly Glu Cys sequence "VH27" –variable region (SEQ ID NO :42)

Glu Val Gln Leu Val Glu Ser Gly Gly Gly Leu Val Gln Pro Gly Gly Ser Leu Arg Leu Ser

FIG. 32E

Cys Ala Ala Ser Gly Phe Thr Phe Ser Asp Ala Trp Met Asp Trp Val Arg Gln Ala Pro

Gly Lys Gly Leu Glu Trp Val Ala Glu Ile Arg Ser Lys Ala Asn Asn His Ala Thr Phe

Tyr Ala Glu Ser Val Lys Gly Arg Phe Thr Ile Ser Arg Asp Asp Ser Lys Ser Ser Val

Tyr Leu Gln Met Asn Ser Leu Lys Thr Glu Asp Thr Gly Val Tyr Tyr Cys Thr Arg Val

Lys Val Gly Phe Asp Asn Trp Gly Gln Gly Thr Leu Val Thr Val Ser Ser sequence "VH19" –variable region (SEQ ID NO :43)

Glu Val Gln Leu Val Glu Ser Gly Gly Gly Leu Val Gln Pro Gly Gly Ser Leu Lys Leu Ser

Cys Ala Ala Ser Gly Phe Thr Phe Ser Asp Ala Trp Met Asp Trp Val Arg Gln Ser Pro

Glu Met Gly Leu Glu Trp Val Ala Glu Ile Arg Ser Lys Ala Asn Asn His Ala Thr Phe

Tyr Ala Glu Ser Val Lys Gly Arg Phe Thr Ile Ser Arg Asp Asp Ser Lys Ser Ser Val

Tyr Leu Gln Met Asn Ser Leu Arg Ala Glu Asp Thr Gly Ile Tyr Tyr Cys Thr Arg Val

Lys Val Gly Phe Asp Asn Trp Gly Gln Gly Thr Thr Leu Thr Val Ser Ser

Sequence "VK5" –variable region (SEQ ID NO :44)

Asp Ile Gln Met Thr Gln Ser Pro Ser Ser Leu Ser Val Ser Val Gly Asp Arg Val Thr

Ile Thr Cys Arg Ala Ser Glu Asn Ile Tyr Ser Asn Leu Ala Trp Tyr Gln Gln Lys Pro

Gly Lys Ala Pro Lys Leu Leu Val His Ala Ala Thr Asn Leu Glu Ser Gly Val Pro Ser

Arg Phe Ser Gly Ser Gly Ser Gly Thr Asp Tyr Thr Leu Thr Ile Ser Ser Leu Gln Pro

Glu Asp Phe Gly Thr Tyr Tyr Cys Gln His Phe Trp Gly Thr Pro Arg Thr Phe Gly Gln

Gly Thr Lys Leu Glu Ile Lys

FIG. 32F

Sequence "VK12" – variable region (SEQ ID NO :45)

Asp Ile Gln Met Thr Gln Ser Pro Ser Ser Leu Ser Ala Ser Val Gly Asp Arg Val Thr

Ile Thr Cys Arg Ala Ser Glu Asn Ile Tyr Ser Asn Leu Ala Trp Tyr Gln Gln Lys Asp

Gly Lys Ser Pro Gln Leu Leu Val His Ala Ala Thr Asn Leu Ala Asp Gly Val Pro Ser

Arg Phe Ser Gly Ser Gly Ser Gly Thr Gln Tyr Ser Leu Thr Ile Ser Ser Leu Gln Pro

Glu Asp Phe Gly Ser Tyr Tyr Cys Gln His Phe Trp Gly Thr Pro Arg Thr Phe Gly Gly

Gly Thr Lys Leu Glu Ile Lys

Sequence "VK15" – variable region (SEQ ID NO :46)

Asp Ile Gln Met Thr Gln Ser Pro Ser Ser Leu Ser Ala Ser Val Gly Asp Arg Val Thr

Ile Thr Cys Arg Ala Ser Glu Asn Ile Tyr Ser Asn Leu Ala Trp Tyr Gln Gln Lys Pro

Gly Lys Ala Pro Lys Leu Leu Leu His Ala Ala Thr Asn Leu Ala Ser Gly Val Pro Ser

Arg Phe Ser Gly Ser Gly Ser Gly Thr Asp Tyr Thr Leu Thr Ile Ser Ser Leu Gln Pro

Glu Asp Phe Ala Thr Tyr Tyr Cys Gln His Phe Trp Gly Thr Pro Arg Thr Phe Gly Gln

Gly Thr Lys Leu Glu Ile Lys

Sequence of human CSF1, 1-444 (SEQ ID NO:47)

MetThrAlaProGlyAlaAlaGlyArgCysProProThrThrTrpLeuGlySerLeuLeu

LeuLeuValCysLeuLeuAlaSerArgSerIleThrGluGluValSerGluTyrCysSer

HisMetIleGlySerGlyHisLeuGlnSerLeuGlnArgLeuIleAspSerGlnMetGlu

FIG. 32G

ThrSerCysGlnIleThrPheGluPheValAspGlnGluGlnLeuLysAspProValCys
TyrLeuLysLysAlaPheLeuLeuValGlnAspIleMetGluAspThrMetArgPheArg
AspAsnThrProAsnAlaIleAlaIleValGlnLeuGlnGluLeuSerLeuArgLeuLys
SerCysPheThrLysAspTyrGluGluHisAspLysAlaCysValArgThrPheTyrGlu
ThrProLeuGlnLeuLeuGluLysValLysAsnValPheAsnGluThrLysAsnLeuLeu
AspLysAspTrpAsnIlePheSerLysAsnCysAsnAsnSerPheAlaGluCysSerSer
GlnAspValValThrLysProAspCysAsnCysLeuTyrProLysAlaIleProSerSer
AspProAlaSerValSerProHisGlnProLeuAlaProSerMetAlaProValAlaGly
LeuThrTrpGluAspSerGluGlyThrGluGlySerSerLeuLeuProGlyGluGlnPro
LeuHisThrValAspProGlySerAlaLysGlnAlaProProArgSerThrCysGlnSer
PheGluProProGluThrProValValLysAspSerThrIleGlyGlySerProGlnPro
ArgProSerValGlyAlaPheAsnProGlyMetGluAspIleLeuAspSerAlaMetGly
ThrAsnTrpValProGluGluAlaSerGlyGluAlaSerGluIleProValProGlnGly
ThrGluLeuSerProSerArgProGlyGlyGlySerMetGlnThrGluProAlaArgPro
SerAsnPheLeuSerAlaSerSerProLeuProAlaSerAlaLysGlyGlnGlnProAla
AspValThrGlyThrAlaLeuProArgValGlyProValArgProThrGlyGlnAspTrp
AsnHisThrProGlnLysThrAspHisProSerAlaLeuLeuArgAspProProGluPro
GlySerProArgIleSerSerLeuArgProGlnGlyLeuSerAsnProSerThrLeuSer
AlaGlnProGlnLeuSerArgSerHisSerSerGlySerValLeuProLeuGlyGluLeu
GluGlyArgArg

FIG. 32H

```
                        SEQUENCE LISTING

<160> NUMBER OF SEQ ID NOS: 47

<210> SEQ ID NO 1
<211> LENGTH: 1404
<212> TYPE: DNA
<213> ORGANISM: Mus musculus

<400> SEQUENCE: 1
atgtacttgg gactgaacta tgtattcata gtttttctcc taaatggtgt ccagagtgaa     60
gtgaagcttg aggagtctgg aggaggcttg gtgcagcctg gaggatccat gaaactctct    120
tgtgctgcct ctggattcac ttttagtgac gcctggatgg actgggtccg ccagtctcca    180
gagatgggac ttgagtgggt tgctgaaatt agaagcaaag ctaataatca tgcaacattc    240
tatgctgagt ctgtgaaagg gaggttcacc atctcaagag atgattccaa aagtagtgtc    300
tacctgcaaa tgaacagctt aagacctgaa gacactggca tttattactg taccagggta    360
aaggtaggct ttgacaactg gggccaaggc accactctca cagtctcctc agccaaaaca    420
acagccccat cggtctatcc actggcccct gtgtgtggag atacaactgg ctcctcggtg    480
actctaggat gcctggtcaa gggttatttc cctgagccag tgaccttgac ctggaactct    540
```

```
ggatccctgt ccagtggtgt gcacaccttc ccagctgtcc tgcagtctga cctctacacc      600
ctcagcagct cagtgactgt aacctcgagc acctggccca gccagtccat cacctgcaat      660
gtggcccacc cggcaagcag caccaaggtg acaagaaaa ttgagcccag agggcccaca       720
atcaagccct gtcctccatg caaatgccca gcacctaacc tcttgggtgg accatccgtc      780
ttcatcttcc ctccaaagat caaggatgta ctcatgatct ccctgagccc catagtcaca      840
tgtgtggtgg tggatgtgag cgaggatgac ccagatgtcc agatcagctg gtttgtgaac      900
aacgtggaag tacacacagc tcagacacaa acccatagag aggattacaa cagtactctc      960
cgggtggtca gtgccctccc catccagcac caggactgga tgagtggcaa ggagttcaaa     1020
tgcaaggtca acaacaaaga cctcccagcg cccatcgaga gaaccatctc aaaacccaaa     1080
gggtcagtaa gagctccaca ggtatatgtc ttgcctccac cagaagaaga gatgactaag     1140
aaacaggtca ctctgacctg catggtcaca gacttcatgc ctgaagacat ttacgtggag     1200
tggaccaaca acgggaaaac agagctaaac tacaagaaca ctgaaccagt cctggactct     1260
gatggttctt acttcatgta cagcaagctg agagtggaaa agaagaactg ggtggaaaga     1320
aatagctact cctgttcagt ggtccacgag ggtctgcaca atcaccacac gactaagagc     1380
ttctcccgga ctccgggtaa atga                                            1404
```

<210> SEQ ID NO 2
<211> LENGTH: 467
<212> TYPE: PRT
<213> ORGANISM: Mus musculus

<400> SEQUENCE: 2

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Met Gly Leu
    50                  55                  60

Glu Trp Val Ala Glu Ile Arg Ser Lys Ala Asn Asn His Ala Thr Phe
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Ser Leu Arg Pro Glu Asp Thr
            100                 105                 110

Gly Ile Tyr Tyr Cys Thr Arg Val Lys Val Gly Phe Asp Asn Trp Gly
        115                 120                 125

Gln Gly Thr Thr Leu Thr Val Ser Ser Ala Lys Thr Thr Ala Pro Ser
    130                 135                 140

Val Tyr Pro Leu Ala Pro Val Cys Gly Asp Thr Thr Gly Ser Ser Val
145                 150                 155                 160

Thr Leu Gly Cys Leu Val Lys Gly Tyr Phe Pro Glu Pro Val Thr Leu
                165                 170                 175

Thr Trp Asn Ser Gly Ser Leu Ser Gly Val His Thr Phe Pro Ala
            180                 185                 190

Val Leu Gln Ser Asp Leu Tyr Thr Leu Ser Ser Ser Val Thr Val Thr
        195                 200                 205

Ser Ser Thr Trp Pro Ser Gln Ser Ile Thr Cys Asn Val Ala His Pro

```
                   210                 215                 220
Ala Ser Ser Thr Lys Val Asp Lys Lys Ile Glu Pro Arg Gly Pro Thr
225                 230                 235                 240

Ile Lys Pro Cys Pro Pro Cys Lys Cys Pro Ala Pro Asn Leu Leu Gly
            245                 250                 255

Gly Pro Ser Val Phe Ile Phe Pro Pro Lys Ile Lys Asp Val Leu Met
                260                 265                 270

Ile Ser Leu Ser Pro Ile Val Thr Cys Val Val Val Asp Val Ser Glu
            275                 280                 285

Asp Asp Pro Asp Val Gln Ile Ser Trp Phe Val Asn Asn Val Glu Val
        290                 295                 300

His Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
                325                 330                 335

Lys Glu Phe Lys Cys Lys Val Asn Asn Lys Asp Leu Pro Ala Pro Ile
            340                 345                 350

Glu Arg Thr Ile Ser Lys Pro Lys Gly Ser Val Arg Ala Pro Gln Val
        355                 360                 365

Tyr Val Leu Pro Pro Pro Glu Glu Glu Met Thr Lys Lys Gln Val Thr
    370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
            420                 425                 430

Glu Lys Lys Asn Trp Val Glu Arg Asn Ser Tyr Ser Cys Ser Val Val
        435                 440                 445

His Glu Gly Leu His Asn His His Thr Thr Lys Ser Phe Ser Arg Thr
    450                 455                 460

Pro Gly Lys
465

<210> SEQ ID NO 3
<211> LENGTH: 705
<212> TYPE: DNA
<213> ORGANISM: Mus musculus

<400> SEQUENCE: 3
atgagtgtgc ccactcaggt cctggggttg ctgctgctgt ggcttacaga tgccagatgt      60
gacatccaga tgactcagtc tccagcctcc ctatctgtat ctgtgggaga aactgtcacc     120
atcacatgtc gagcaagtga gaatatttac agtaatttag catggtatca gcagaaacag     180
ggaaaatctc ctcagctcct ggtccatgct gcaacaaact tagcagatgg tgtgccatca     240
aggttcagtg gcagtggatc aggcacacag tattccctca agatcaacag cctgcagtct     300
gaagattttg ggagttatta ctgtcaacat ttttgggta ctcctcggac gttcggtgga     360
ggcaccaagt tggaaatcaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag cacctcacg     600 ttgaccaagg acgagtatga acgacataac agctatacct gtgaggccac tcacaagaca     660
```
tcaacttcac ccattgtcaa gagcttcaac aggaatgagt gttag 705

<210> SEQ ID NO 4
<211> LENGTH: 234
<212> TYPE: PRT
<213> ORGANISM: Mus musculus

<400> SEQUENCE: 4

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ala Ser Leu Ser
                20                  25                  30

Val Ser Val Gly Glu Thr Val Thr Ile Thr Cys Arg Ala Ser Glu Asn
            35                  40                  45

Ile Tyr Ser Asn Leu Ala Trp Tyr Gln Gln Lys Gln Gly Lys Ser Pro
    50                  55                  60

Gln Leu Leu Val His Ala Ala Thr Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
                100                 105                 110

Gly Thr Pro Arg Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
    195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230

<210> SEQ ID NO 5
<211> LENGTH: 19
<212> TYPE: PRT
<213> ORGANISM: Mus musculus

<400> SEQUENCE: 5

Met Tyr Leu Gly Leu Asn Tyr Val Phe Ile Val Phe Leu Leu Asn Gly
1               5                   10                  15

Val Gln Ser

<210> SEQ ID NO 6
<211> LENGTH: 118
<212> TYPE: PRT
<213> ORGANISM: Mus musculus

<400> SEQUENCE: 6

Glu Val Lys Leu Glu Glu Ser Gly Gly Gly Leu Val Gln Pro Gly Gly
1               5                   10                  15

```
Ser Met Lys Leu Ser Cys Ala Ala Ser Gly Phe Thr Phe Ser Asp Ala
            20                  25                  30

Trp Met Asp Trp Val Arg Gln Ser Pro Glu Met Gly Leu Glu Trp Val
        35                  40                  45

Ala Glu Ile Arg Ser Lys Ala Asn Asn His Ala Thr Phe Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Pro Glu Asp Thr Gly Ile Tyr
                85                  90                  95

Tyr Cys Thr Arg Val Lys Val Gly Phe Asp Asn Trp Gly Gln Gly Thr
            100                 105                 110

Thr Leu Thr Val Ser Ser
        115

<210> SEQ ID NO 7
<211> LENGTH: 330
<212> TYPE: PRT
<213> ORGANISM: Mus musculus

<400> SEQUENCE: 7

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
```

```
                    260                 265                 270
Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
        290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 8
<211> LENGTH: 20
<212> TYPE: PRT
<213> ORGANISM: Mus musculus

<400> SEQUENCE: 8

Met Ser Val Pro Thr Gln Val Leu Gly Leu Leu Leu Leu Trp Leu Thr
1               5                   10                  15

Asp Ala Arg Cys
            20

<210> SEQ ID NO 9
<211> LENGTH: 107
<212> TYPE: PRT
<213> ORGANISM: Mus musculus

<400> SEQUENCE: 9

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

His Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Arg
                85                  90                  95

Thr Phe Gly Gly Gly Thr Lys Leu Glu Ile Lys
            100                 105

<210> SEQ ID NO 10
<211> LENGTH: 107
<212> TYPE: PRT
<213> ORGANISM: Mus musculus

<400> SEQUENCE: 10

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80
```

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 11
<211> LENGTH: 8
<212> TYPE: PRT
<213> ORGANISM: Mus musculus

<400> SEQUENCE: 11

Gly Phe Thr Phe Ser Asp Ala Trp
1               5

<210> SEQ ID NO 12
<211> LENGTH: 10
<212> TYPE: PRT
<213> ORGANISM: Mus musculus

<400> SEQUENCE: 12

Ile Arg Ser Lys Ala Asn Asn His Ala Thr
1               5                   10

<210> SEQ ID NO 13
<211> LENGTH: 9
<212> TYPE: PRT
<213> ORGANISM: Mus musculus

<400> SEQUENCE: 13

Thr Arg Val Lys Val Gly Phe Asp Asn
1               5

<210> SEQ ID NO 14
<211> LENGTH: 6
<212> TYPE: PRT
<213> ORGANISM: Mus musculus

<400> SEQUENCE: 14

Glu Asn Ile Tyr Ser Asn
1               5

<210> SEQ ID NO 15
<211> LENGTH: 3
<212> TYPE: PRT
<213> ORGANISM: Mus musculus

<400> SEQUENCE: 15

Ala Ala Thr
1

<210> SEQ ID NO 16
<211> LENGTH: 9
<212> TYPE: PRT
<213> ORGANISM: Mus musculus

<400> SEQUENCE: 16

Gln His Phe Trp Gly Thr Pro Arg Thr
1               5

<210> SEQ ID NO 17
<211> LENGTH: 5
<212> TYPE: PRT
<213> ORGANISM: Mus musculus

```
<400> SEQUENCE: 17

Asp Ala Trp Met Asp
1               5

<210> SEQ ID NO 18
<211> LENGTH: 19
<212> TYPE: PRT
<213> ORGANISM: Mus musculus

<400> SEQUENCE: 18

Glu Ile Arg Ser Lys Ala Asn Asn His Ala Thr Phe Tyr Ala Glu Ser
1               5                   10                  15

Val Lys Gly

<210> SEQ ID NO 19
<211> LENGTH: 7
<212> TYPE: PRT
<213> ORGANISM: Mus musculus

<400> SEQUENCE: 19

Val Lys Val Gly Phe Asp Asn
1               5

<210> SEQ ID NO 20
<211> LENGTH: 11
<212> TYPE: PRT
<213> ORGANISM: Mus musculus

<400> SEQUENCE: 20

Arg Ala Ser Glu Asn Ile Tyr Ser Asn Leu Ala
1               5                   10

<210> SEQ ID NO 21
<211> LENGTH: 7
<212> TYPE: PRT
<213> ORGANISM: Mus musculus

<400> SEQUENCE: 21

Ala Ala Thr Asn Leu Ala Asp
1               5

<210> SEQ ID NO 22
<211> LENGTH: 9
<212> TYPE: PRT
<213> ORGANISM: Mus musculus

<400> SEQUENCE: 22

Gln His Phe Trp Gly Thr Pro Arg Thr
1               5

<210> SEQ ID NO 23
<211> LENGTH: 7
<212> TYPE: PRT
<213> ORGANISM: Mus musculus

<400> SEQUENCE: 23

Gly Phe Thr Phe Ser Asp Ala
1               5

<210> SEQ ID NO 24
<211> LENGTH: 8
<212> TYPE: PRT
<213> ORGANISM: Mus musculus
```

-continued

```
<400> SEQUENCE: 24

Arg Ser Lys Ala Asn Asn His Ala
1               5

<210> SEQ ID NO 25
<211> LENGTH: 7
<212> TYPE: PRT
<213> ORGANISM: Mus musculus

<400> SEQUENCE: 25

Val Lys Val Gly Phe Asp Asn
1               5

<210> SEQ ID NO 26
<211> LENGTH: 11
<212> TYPE: PRT
<213> ORGANISM: Mus musculus

<400> SEQUENCE: 26

Arg Ala Ser Glu Asn Ile Tyr Ser Asn Leu Ala
1               5                   10

<210> SEQ ID NO 27
<211> LENGTH: 7
<212> TYPE: PRT
<213> ORGANISM: Mus musculus

<400> SEQUENCE: 27

Ala Ala Thr Asn Leu Ala Asp
1               5

<210> SEQ ID NO 28
<211> LENGTH: 9
<212> TYPE: PRT
<213> ORGANISM: Mus musculus

<400> SEQUENCE: 28

Gln His Phe Trp Gly Thr Pro Arg Thr
1               5

<210> SEQ ID NO 29
<211> LENGTH: 972
<212> TYPE: PRT
<213> ORGANISM: Homo sapiens

<400> SEQUENCE: 29

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
```

```
            115                 120                 125
Leu Thr Asp Pro Val Leu Glu Ala Gly Val Ser Leu Arg Val Arg
    130                 135                 140
Gly Arg Pro Leu Met Arg His Thr Asn Tyr Ser Phe Ser Pro Trp His
145                 150                 155                 160
Gly Phe Thr Ile His Arg Ala Lys Phe Ile Gln Ser Gln Asp Tyr Gln
                165                 170                 175
Cys Ser Ala Leu Met Gly Gly Arg Lys Val Met Ser Ile Ser Ile Arg
                180                 185                 190
Leu Lys Val Gln Lys Val Ile Pro Gly Pro Ala Leu Thr Leu Val
            195                 200                 205
Pro Ala Glu Leu Val Arg Ile Arg Gly Glu Ala Ala Gln Ile Val Cys
    210                 215                 220
Ser Ala Ser Ser Val Asp Val Asn Phe Asp Val Phe Leu Gln His Asn
225                 230                 235                 240
Asn Thr Lys Leu Ala Ile Pro Gln Gln Ser Asp Phe His Asn Asn Arg
                245                 250                 255
Tyr Gln Lys Val Leu Thr Leu Asn Leu Asp Gln Val Asp Phe Gln His
                260                 265                 270
Ala Gly Asn Tyr Ser Cys Val Ala Ser Asn Val Gln Gly Lys His Ser
                275                 280                 285
Thr Ser Met Phe Phe Arg Val Val Glu Ser Ala Tyr Leu Asn Leu Ser
    290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                325                 330                 335
Thr Tyr Leu Gly Pro Phe Ser Asp His Gln Pro Glu Pro Lys Leu Ala
                340                 345                 350
Asn Ala Thr Thr Lys Asp Thr Tyr Arg His Thr Phe Thr Leu Ser Leu
                355                 360                 365
Pro Arg Leu Lys Pro Ser Glu Ala Gly Arg Tyr Ser Phe Leu Ala Arg
    370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
                420                 425                 430
Gln Cys Ser Gly His Thr Asp Arg Cys Asp Glu Ala Gln Val Leu Gln
                435                 440                 445
Val Trp Asp Asp Pro Tyr Pro Glu Val Leu Ser Gln Glu Pro Phe His
    450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
Ala Phe Ile Pro Ile Ser Ala Gly Ala His Thr His Pro Pro Asp Glu
                500                 505                 510
Phe Leu Phe Thr Pro Val Val Val Ala Cys Met Ser Ile Met Ala Leu
                515                 520                 525
Leu Leu Leu Leu Leu Leu Leu Leu Tyr Lys Tyr Lys Gln Lys Pro
                530                 535                 540
```

```
Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
            565                 570                 575

Phe Pro Arg Asn Asn Leu Gln Phe Gly Lys Thr Leu Gly Ala Gly Ala
        580                 585                 590

Phe Gly Lys Val Val Glu Ala Thr Ala Phe Gly Leu Gly Lys Glu Asp
    595                 600                 605

Ala Val Leu Lys Val Ala Val Lys Met Leu Lys Ser Thr Ala His Ala
610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
            675                 680                 685

Pro Gly Gln Asp Pro Glu Gly Gly Val Asp Tyr Lys Asn Ile His Leu
690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
                740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
                820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Ser Glu Leu Glu Glu
            930                 935                 940

Glu Ser Ser Ser Glu His Leu Thr Cys Cys Glu Gln Gly Asp Ile Ala
945                 950                 955                 960
```

Gln Pro Leu Leu Gln Pro Asn Asn Tyr Gln Phe Cys
             965                 970

<210> SEQ ID NO 30
<211> LENGTH: 36
<212> TYPE: DNA
<213> ORGANISM: Artificial Sequence
<220> FEATURE:
<223> OTHER INFORMATION: primer sequence

<400> SEQUENCE: 30
gccgccacca tgtacttggg actgaactat gtattc            36

<210> SEQ ID NO 31
<211> LENGTH: 29
<212> TYPE: DNA
<213> ORGANISM: Artificial Sequence
<220> FEATURE:
<223> OTHER INFORMATION: primer sequence

<400> SEQUENCE: 31
ggagatcttc atttacccgg agtccggga                    29

<210> SEQ ID NO 32
<211> LENGTH: 33
<212> TYPE: DNA
<213> ORGANISM: Artificial Sequence
<220> FEATURE:
<223> OTHER INFORMATION: primer sequence

<400> SEQUENCE: 32
gccgccacca tgagtgtgcc cactcaggtc ctg               33

<210> SEQ ID NO 33
<211> LENGTH: 32
<212> TYPE: DNA
<213> ORGANISM: Artificial Sequence
<220> FEATURE:
<223> OTHER INFORMATION: primer sequence

<400> SEQUENCE: 33
gcccgggcta acactcattc ctgttgaagc tc                32

<210> SEQ ID NO 34
<211> LENGTH: 705
<212> TYPE: DNA
<213> ORGANISM: Artificial Sequence
<220> FEATURE:
<223> OTHER INFORMATION: nucleic acid sequence of an antibody light
      chain

<400> SEQUENCE: 34
atgagcgtgc ccacccaggt gctgggcctg ctgctgctgt ggctgaccga cgccagatgc    60
gacatccaga tgacccagag ccccgccagc ctgagcgtga gcgtgggcga gaccgtgacc   120
atcacctgca gggccagcga gaacatctac agcaacctgg cctggtatca gcagaagcag   180
ggcaagagcc cccagctgct ggtgcacgct gccaccaacc tggccgacgg cgtgccctcc   240
aggttcagcg gcagcggctc cggcacccag tacagcctga agatcaacag cctgcagagc   300
gaggacttcg gcagctacta ctgccagcac ttctggggca ccccaaggac cttcggcggc   360
ggcaccaagc tggagatcaa gaggaccgtg gccgccccca gcgtgttcat cttccccccc   420
agcgacgagc agctgaagag cggcaccgcc tccgtggtgt gcctgctgaa caacttctac   480 ccccggagg ccaaggtgca gtggaaggtg gacaacgccc tgcagagcgg caacagccag   540

| | |
|---|---|
| gaaagcgtca ccgagcagga cagcaaggac tccacctaca gcctgagcag caccctgacc | 600 |
| ctgagcaagg ccgactacga aagcacaag gtgtacgcct gcgaggtgac ccaccagggc | 660 |
| ctgtccagcc ccgtgaccaa gagcttcaac aggggcgagt gttga | 705 |

<210> SEQ ID NO 35
<211> LENGTH: 1404
<212> TYPE: DNA
<213> ORGANISM: Artificial Sequence
<220> FEATURE:
<223> OTHER INFORMATION: nucleic acid sequence of an antibody heavy chain

<400> SEQUENCE: 35

| | |
|---|---|
| atgtacctgg gcctgaacta cgtgttcatc gtgtttctgc tgaacggcgt gcagagcgag | 60 |
| gtgaagctgg aggaaagcgg cggagggctg gtgcagccag cgggagcat gaaactgtcc | 120 |
| tgcgccgcca gcggcttcac cttcagcgac gcctggatgg actgggtgcg ccagagcccc | 180 |
| gagatgggcc tggagtgggt ggccgagatc aggtccaagg ccaacaacca cgccaccttc | 240 |
| tacgccgaga gcgtgaaggg caggttcacc atcagcaggg acgacagcaa gagcagcgtg | 300 |
| tacctgcaga tgaacagcct gaggcccgag gacaccggca tctactactg caccagagtg | 360 |
| aaagtgggct tcgacaactg gggccagggc accacactga ccgtgtccag cgccagcacc | 420 |
| aagggcccca gcgtgttccc cctggccccc agctccaaga gcaccagcgg aggaacagct | 480 |
| gctctgggct gcctggtgaa ggactacttc cccgagcccg tgaccgtgtc ttggaacagc | 540 |
| ggagccctga cctccggcgt gcacaccttc ccgccgtgc tgcagagcag cggcctgtac | 600 |
| agcctgagca gcgtggtgac agtgcccagc agcagcctgg gcacccagac ctacatctgc | 660 |
| aacgtgaacc acaagcccag caacaccaag gtggacaaga aggtggagcc caagagctgc | 720 |
| gacaagaccc acacctgtcc tcctgcccca gccccagagc tgctgggcgg accctccgtg | 780 |
| ttcctgttcc cccccaagcc caaggacacc ctgatgatca gcaggacccc cgaggtgacc | 840 |
| tgcgtggtgg tggacgtgtc ccacgaggac ccagaggtga agttcaactg gtacgtggac | 900 |
| ggcgtggagg tgcacaacgc caagaccaag cccagagagg aacagtacaa cagcacctac | 960 |
| agggtggtgt ccgtgctgac cgtgctgcac caggactggc tgaacggcaa ggaatacaag | 1020 |
| tgcaaggtct ccaacaaggc cctgccagcc cccatcgaaa agaccatcag caaggccaag | 1080 |
| ggccagccac gggagcccca ggtgtacacc ctgcccccct cccgggacga gctgaccaag | 1140 |
| aaccaggtgt ccctgacctg tctggtgaag ggcttctacc ccagcgacat cgccgtggag | 1200 |
| tgggagagca acggccagcc cgagaacaac tacaagacca cccccccagt gctggacagc | 1260 |
| gacggcagct ccttcctgta cagcaagctg accgtggaca gagcaggtg gcagcagggc | 1320 |
| aacgtgttca gctgcagcgt gatgcacgag gccctgcaca accactacac ccagaagagc | 1380 |
| ctgagcctgt cccccggcaa gtga | 1404 |

<210> SEQ ID NO 36
<211> LENGTH: 1395
<212> TYPE: DNA
<213> ORGANISM: Artificial Sequence
<220> FEATURE:
<223> OTHER INFORMATION: nucleic acid sequence of an antibody heavy chain

<400> SEQUENCE: 36

| | |
|---|---|
| atgtacctgg gcctgaacta cgtgttcatc gtgtttctgc tgaacggcgt gcagagcgag | 60 |

```
gtgaagctgg aggaaagcgg cggagggctg gtgcagcctg gaggaagcat gaagctgtcc      120
tgcgctgcca gcggcttcac cttcagcgac gcctggatgg actgggtgcg ccagagcccc      180
gagatgggcc tggagtgggt ggccgagatc aggtccaagg ccaacaacca cgccaccttc      240
tacgccgaga gcgtgaaggg caggttcacc atcagcaggg acgacagcaa gagcagcgtg      300
tacctgcaga tgaacagcct gaggcccgag gacaccggca tctactactg caccagagtg      360
aaggtgggct cgacaactg gggccagggc accacactga ccgtgtccag cgccagcacc      420
aagggcccaa gcgtgttccc cctggccccc tgcagcagaa gcaccagcga gagcacagcc      480
gccctgggct gcctggtgaa ggactacttc cccgagcccg tgaccgtgtc ttggaacagc      540
ggagccctga ccagcggcgt gcacaccttc cccgccgtgc tgcagagcag cggcctgtac      600
agcctgagca gcgtggtgac cgtgcccagc agcagcctgg caccaagac ctacacctgc      660 aacgtggacc acaagcccag caacaccaag gtggacaaga gggtggagag caagtacggc      720
ccaccctgcc cctcttgccc agccccgag ttcctgggcg acccagcgt gttcctgttc      780 ccccccaagc caaggacac cctgatgatc agcaggaccc ccgaggtgac ctgcgtggtg      840
gtggacgtgt cccaggaaga tccagaggtc cagttcaact ggtacgtgga cggcgtggag      900
gtgcacaacg ccaagaccaa gcccagagag gaacagttta acagcaccta cagggtggtg      960
tccgtgctga ccgtgctgca ccaggactgg ctgaacggca aggaatacaa gtgcaaggtc     1020
tccaacaagg cctgcccag ctccatcgaa agaccatca gcaaggccaa gggccagcca     1080
cgggagcccc aggtgtacac cctgccaccc agccaagagg aaatgaccaa gaaccaggtg     1140
tccctgacct gtctggtgaa gggcttctac cccagcgaca tcgccgtgga gtgggagagc     1200
aacggccagc ccgagaacaa ctacaagacc accccccag tgctggacag cgacggcagc     1260
ttcttcctgt acagcaggct gaccgtggac aagtccaggt ggcaggaagg caacgtcttt     1320
agctgcagcg tgatgcacga ggccctgcac aaccactaca cccagaagag cctgagcctg     1380
tccctgggca agtga                                                      1395
```

<210> SEQ ID NO 37
<211> LENGTH: 467
<212> TYPE: PRT
<213> ORGANISM: Artificial Sequence
<220> FEATURE:
<223> OTHER INFORMATION: amino acid sequence of antibody heavy chain

<400> SEQUENCE: 37

```
Met Tyr Leu Gly Leu Asn Tyr Val Phe Ile Val Phe Leu Leu Asn Gly
1               5                   10                  15

Val Gln Ser Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asp Ala Trp Met Asp Trp Val Arg Gln Ala Pro Gly Lys Gly Leu
        50                  55                  60

Glu Trp Val Ala Glu Ile Arg Ser Lys Ala Asn Asn His Ala Thr Phe
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Ser Leu Lys Thr Glu Asp Thr
            100                 105                 110

Gly Val Tyr Tyr Cys Thr Arg Val Lys Val Gly Phe Asp Asn Trp Gly
        115                 120                 125
```

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 38
<211> LENGTH: 467
<212> TYPE: PRT
<213> ORGANISM: Artificial Sequence
<220> FEATURE:
<223> OTHER INFORMATION: amino acid sequence of antibody heavy chain

<400> SEQUENCE: 38

Met Tyr Leu Gly Leu Asn Tyr Val Phe Ile Val Phe Leu Leu Asn Gly
1               5                   10                  15

```
Val Gln Ser Glu Val Gln Leu Val Glu Ser Gly Gly Leu Val Gln
             20                  25                  30

Pro Gly Gly Ser Leu Lys Leu Ser Cys Ala Ala Ser Gly Phe Thr Phe
             35                  40                  45

Ser Asp Ala Trp Met Asp Trp Val Arg Gln Ser Pro Glu Met Gly Leu
 50                  55                  60

Glu Trp Val Ala Glu Ile Arg Ser Lys Ala Asn Asn His Ala Thr Phe
 65                  70                  75                  80

Tyr Ala Glu Ser Val Lys Gly Arg Phe Thr Ile Ser Arg Asp Asp Ser
             85                  90                  95

Lys Ser Ser Val Tyr Leu Gln Met Asn Ser Leu Arg Ala Glu Asp Thr
            100                 105                 110

Gly Ile Tyr Tyr Cys Thr Arg Val Lys Val Gly Phe Asp Asn Trp Gly
            115                 120                 125

Gln Gly Thr Thr Leu Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430
```

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 39
<211> LENGTH: 234
<212> TYPE: PRT
<213> ORGANISM: Artificial Sequence
<220> FEATURE:
<223> OTHER INFORMATION: amino acid sequence of antibody light chain

<400> SEQUENCE: 39

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Val Ser Val Gly Asp Arg Val Thr Ile Thr Cys Arg Ala Ser Glu Asn
        35                  40                  45

Ile Tyr Ser Asn Leu Ala Trp Tyr Gln Gln Lys Pro Gly Lys Ala Pro
    50                  55                  60

Lys Leu Leu Val His Ala Ala Thr Asn Leu Glu Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Gly Thr Tyr Tyr Cys Gln His Phe Trp
            100                 105                 110

Gly Thr Pro Arg Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 40
<211> LENGTH: 234
<212> TYPE: PRT
<213> ORGANISM: Artificial Sequence
<220> FEATURE:
<223> OTHER INFORMATION: amino acid sequence of antibody light chain

<400> SEQUENCE: 40

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

```
Ala Ser Val Gly Asp Arg Val Thr Ile Thr Cys Arg Ala Ser Glu Asn
        35                  40                  45

Ile Tyr Ser Asn Leu Ala Trp Tyr Gln Gln Lys Asp Gly Lys Ser Pro
 50                  55                  60

Gln Leu Leu Val His Ala Ala Thr Asn Leu Ala Asp Gly Val Pro Ser
 65                  70                  75                  80

Arg Phe Ser Gly Ser Gly Ser Gly Thr Gln Tyr Ser Leu Thr Ile Ser
                 85                  90                  95

Ser Leu Gln Pro Glu Asp Phe Gly Ser Tyr Tyr Cys Gln His Phe Trp
            100                 105                 110

Gly Thr Pro Arg Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 41
<211> LENGTH: 234
<212> TYPE: PRT
<213> ORGANISM: Artificial Sequence
<220> FEATURE:
<223> OTHER INFORMATION: amino acid sequence of antibody light chain

<400> SEQUENCE: 41

Met Ser Val Pro Thr Gln Val Leu Gly Leu Leu Leu Leu Trp Leu Thr
 1               5                  10                  15

Asp Ala Arg Cys Asp Ile Gln Met Thr Gln Ser Pro Ser Ser Leu Ser
             20                  25                  30

Ala Ser Val Gly Asp Arg Val Thr Ile Thr Cys Arg Ala Ser Glu Asn
         35                  40                  45

Ile Tyr Ser Asn Leu Ala Trp Tyr Gln Gln Lys Pro Gly Lys Ala Pro
 50                  55                  60

Lys Leu Leu Leu His Ala Ala Thr Asn Leu Ala Ser Gly Val Pro Ser
 65                  70                  75                  80

Arg Phe Ser Gly Ser Gly Ser Gly Thr Asp Tyr Thr Leu Thr Ile Ser
                 85                  90                  95

Ser Leu Gln Pro Glu Asp Phe Ala Thr Tyr Tyr Cys Gln His Phe Trp
            100                 105                 110

Gly Thr Pro Arg Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160
```

```
Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 42
<211> LENGTH: 118
<212> TYPE: PRT
<213> ORGANISM: Artificial Sequence
<220> FEATURE:
<223> OTHER INFORMATION: amino acid sequence of antibody variable region

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Asn Asn His Ala Thr Phe Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Lys Thr Glu Asp Thr Gly Val Tyr
                85                  90                  95

Tyr Cys Thr Arg Val Lys Val Gly Phe Asp Asn Trp Gly Gln Gly Thr
            100                 105                 110

Leu Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: amino acid sequence of antibody variable region

<400> SEQUENCE: 43

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ala
            20                  25                  30

Trp Met Asp Trp Val Arg Gln Ser Pro Glu Met Gly Leu Glu Trp Val
        35                  40                  45

Ala Glu Ile Arg Ser Lys Ala Asn Asn His Ala Thr Phe Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Arg Val Lys Val Gly Phe Asp Asn Trp Gly Gln Gly Thr
```

Thr Leu Thr Val Ser Ser
            115

<210> SEQ ID NO 44
<211> LENGTH: 107
<212> TYPE: PRT
<213> ORGANISM: Artificial Sequence
<220> FEATURE:
<223> OTHER INFORMATION: amino acid sequence of antibody variable region

<400> SEQUENCE: 44

Asp Ile Gln Met Thr Gln Ser Pro Ser Ser Leu Ser Val Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Val
        35                  40                  45

His Ala Ala Thr Asn Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Gly Thr Tyr Tyr Cys Gln His Phe Trp Gly Thr Pro Arg
                85                  90                  95

Thr Phe Gly Gln Gly Thr Lys Leu Glu Ile Lys
            100                 105

<210> SEQ ID NO 45
<211> LENGTH: 107
<212> TYPE: PRT
<213> ORGANISM: Artificial Sequence
<220> FEATURE:
<223> OTHER INFORMATION: amino acid sequence of antibody variable region

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Asp Gly Lys Ser Pro Gln Leu Leu Val
        35                  40                  45

His Ala Ala Thr Asn Leu Ala Asp Gly Val Pro Ser Arg Phe Ser Gly
    50                  55                  60

Ser Gly Ser Gly Thr Gln Tyr Ser Leu Thr Ile Ser Ser Leu Gln Pro
65                  70                  75                  80

Glu Asp Phe Gly Ser Tyr Tyr Cys Gln His Phe Trp Gly Thr Pro Arg
                85                  90                  95

Thr Phe Gly Gly Gly Thr Lys Leu Glu Ile Lys
            100                 105

<210> SEQ ID NO 46
<211> LENGTH: 107
<212> TYPE: PRT
<213> ORGANISM: Artificial Sequence
<220> FEATURE:
<223> OTHER INFORMATION: amino acid sequence of antibody variable region

<400> SEQUENCE: 46

Asp Ile Gln Met Thr Gln Ser Pro Ser Ser Leu Ser Ala Ser Val Gly
1               5                   10                  15

-continued

```
Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Leu
        35                  40                  45

His Ala Ala Thr Asn Leu Ala Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Gly Thr Pro Arg
                85                  90                  95

Thr Phe Gly Gln Gly Thr Lys Leu Glu Ile Lys
                100                 105

<210> SEQ ID NO 47
<211> LENGTH: 444
<212> TYPE: PRT
<213> ORGANISM: Artificial Sequence
<220> FEATURE:
<223> OTHER INFORMATION: amino acid sequence of human CSF1

<400> SEQUENCE: 47

Met Thr Ala Pro Gly Ala Ala Gly Arg Cys Pro Pro Thr Thr Trp Leu
 1               5                  10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
 50                  55                  60

Ile Thr Phe Glu Phe Val Asp Gln Glu Gln Leu Lys Asp Pro Val Cys
 65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
                100                 105                 110

Gln Glu Leu Ser Leu Arg Leu Lys Ser Cys Phe Thr Lys Asp Tyr Glu
            115                 120                 125

Glu His Asp Lys Ala Cys Val Arg Thr Phe Tyr Glu Thr Pro Leu Gln
        130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Ala Pro Pro Arg Ser
                245                 250                 255

Thr Cys Gln Ser Phe Glu Pro Pro Glu Thr Pro Val Val Lys Asp Ser
            260                 265                 270
```

-continued

```
Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
                340                 345             350

Ser Ala Lys Gly Gln Gln Pro Ala Asp Val Thr Gly Thr Ala Leu Pro
            355                 360                 365

Arg Val Gly Pro Val Arg Pro Thr Gly Gln Asp Trp Asn His Thr Pro
    370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
                420                 425             430

Ser Val Leu Pro Leu Gly Glu Leu Glu Gly Arg Arg
                435                 440
```

ANTIBODY AGAINST THE CSF-1R

CROSS REFERENCE TO RELATED APPLICATIONS

This application is a continuation of U.S. application Ser. No. 13/026,944, filed Feb. 14, 2011, now U.S. Pat. No. 8,470,977, issued on Jul. 25, 2013, which is a continuation-in-part of U.S. application Ser. No. 12/922,441, now U.S. Pat. No. 8,604,170, issued on Dec. 10, 2013, with 35 U.S.C. §371(c) date Dec. 7, 2010, which is a U.S. national phase application based on PCT/EP2009/001733, filed Mar. 11, 2009, and which claimed priority of European Application No. 08 36 0005.6, filed Mar. 14, 2008, and the benefit of U.S. Provisional Application No. 61/043,884, filed Apr. 10, 2008.

SEQUENCE LISTING

The instant application contains a Sequence Listing which was submitted via EFS-Web on Apr. 4, 2011, in the parent application, U.S. patent application Ser. No. 13/026,944 filed Feb. 14, 2011, and is hereby incorporated by reference in its entirety.

DESCRIPTION

The CSF-1 (Colony-Stimulating Factor-1) is a cytokine expressed particularly by various types of cells. It is a differentiation, growth and survival factor for cells of the mononuclear phagocyte lineage which express the receptor for CSF-1 (CSF-1R) (SHERR. Colony-stimulating factor-1 receptor. *blood.* 1990, vol. 75, no. 1, p. 1-12.). CSF-1R is a tyrosine kinase receptor encoded by the c-fms protoonogene containing an intracellular kinase domain and a ligand-binding extracellular region organized in five immunoglobulin-like subdomains. Response to CSF-1 results in increased survival, growth, differentiation, and reversible changes in function. The c-fms gene is itself a macrophage differentiation marker. The extent of c-fms expression is stronger than that of other macrophage-specific genes including lysozyme and a macrophage-specific protein tyrosine phosphatase (HUME, et al. Regulation of CSF-1 receptor expression. *Molecular reproduction and development.* 1997, vol. 46, no. 1, p. 46-52.).

In addition to cells of the mononuclear phagocyte lineage, the CSF-1R is also expressed by many types of human tumors. In breast cancer, CSF-1R expression is associated with larger tumor sizes and decreased survival (KLUGER, et al. Macrophage colony-stimulating factor-1 receptor expression is associated with poor outcome in breast cancer by large cohort tissue microarray analysis. *Clinical cancer research.* 2004, vol. 10, no. 1, p. 173-7.; SCHOLL, et al. Anti-colony-stimulating factor-1 antibody staining in primary breast adenocarcinomas correlates with marked inflammatory cell infiltrates and prognosis. *Journal of the National Cancer Institute.* 1994, vol. 86, no. 2, p. 120-6.). In epithelial ovarian cancer, the majority of primary tumors and metastases strongly express the CSF-1R, and metastases frequently co-express CSF-1 and CSF-1R. The CSF-1R is also expressed by tumor-infiltrating macrophages (CHAMBERS, et al. Overexpression of epithelial macrophage colony-stimulating factor (CSF-1) and CSF-1 receptor: a poor prognostic factor in epithelial ovarian cancer, contrasted with a protective effect of stromal CSF-1. *Clinical Cancer Research.* 1997, vol. 3, no. 6, p. 999-1007.). In ovarian and endometrial cancers, Northern blot analysis shows that the vast majority of tumors co-express CSF-1 and CSF-1R, while CSF-1R expression is only weakly detected in normal endometrial tissue samples (BAÏOCCHI, et al. Expression of the macrophage colony-stimulating factor and its receptor in gynecologic malignancies. *Cancer.* 1991, vol. 67, no. 4, p. 990-6.). In cervical carcinomas, CSF-1R expression is up-regulated both in tumor stroma and in tumor epithelium, compared with normal endometrium (KIRMA, et al. Elevated expression of the oncogene c-fms and its ligand, the macrophage colony-stimulating factor-1, in cervical cancer and the role of transforming growth factor-beta1 in inducing c-fms expression. *Cancer res.* 2007, vol. 67, no. 5, p. 1918-26.). In renal carcinoma, infiltration of tumor-associated macrophages expressing high levels of CSF-1R is associated with tumor progression (HEMMERLEIN, et al. Expression of acute and late-stage inflammatory antigens, c-fms, CSF-1, and human monocytic serine esterase 1, in tumor-associated macrophages of renal cell carcinomas. *Cancer immunology, immunotherapy.* 2000, vol. 49, no. 9, p. 485-92.). CSF-1R is expressed by close to 100% prostatic intraepithelial neoplasia or cancer samples (IDE, et al. Expression of colony-stimulating factor 1 receptor during prostate development and prostate cancer progression. *Proc. Natl. Acad. Sci. U.S.A.* 2002, vol. 99, no. 22, p. 14404-9.). CSF-1R expression has also been detected in acute myeloblastic leukemias and B-cell chronic lymphocytic leukemias (RAMBALDI, et al. Expression of the macrophage colony-stimulating factor and c-fms genes in human acute myeloblastic leukemia cells. *Journal of Clinical Investigation.* 1988, vol. 81, no. 4, p. 1030-5.).

Work done by immunohistochemistry and in situ hybridization has demonstrated specificity of the expression of CSF-1 in invasive breast cancer cells while such production is not observed in intra-canal or non-invasive tumor cells (SCHOLL, et al. Anti-colony-stimulating factor-1 antibody staining in primary breast adenocarcinomas correlates with marked inflammatory cell infiltrates and prognosis. *Journal of the National Cancer Institute.* 1994, vol. 86, no. 2, p. 120-6; TANG, et al. M-CSF (monocyte colony stimulating factor) and M-CSF receptor expression by breast tumor cells: M-CSF mediated recruitment of tumor infiltrating monocytes?. *Journal of cellular biochemistry.* 1992, vol. 50, no. 4, p. 350-6). Production of CSF-1 by invasive tumor cells correlates with its increase in concentration in the plasma of patients, where it can exceed 1000 pg/ml compared with less than 300 pg/ml in normal subjects. High serum concentration correlates with advanced stages of the disease and unfavorable short term prognostic (SCHOLL, et al. Circulating levels of colony-stimulating factor 1 as a prognostic indicator in 82 patients with epithelial ovarian cancer. *British journal of cancer.* 1994, vol. 69, no. 2, p. 342-6; SCHOLL. Circulating levels of the macrophage colony stimulating factor CSF-1 in primary and metastatic breast cancer patients. A pilot study. *Breast cancer research and treatment.* 1996, vol. 39, no. 3, p. 275-83). Moreover, it has been demonstrated that CSF-1 stimulates mobility and invasiveness of tumor cells (DORSCH, et al. Macrophage colony-stimulating factor gene transfer into tumor cells induces macrophage infiltration but not tumor suppression. *European journal of immunology.* 1993, vol. 23, no. 1, p. 186-90; WANG, et al. Induction of monocyte migration by recombinant macrophage colony-stimulating factor. *Journal of immunology.* 1988, vol. 141, no. 2, p. 575-9; FILDERMAN, et al. Macrophage colony-stimulating factor (CSF-1) enhances invasiveness in CSF-1 receptor-positive carcinoma cell lines. *Cancer res.* 1992, vol. 52, no. 13, p. 3661-6).

CSF-1 also has a chemotactic effect on precursors of the myeloid line, which facilitates infiltration of monocytes in the tumor. However, the presence of these monocytes is not sufficient to observe destruction of the tumor by the immune system (DORSCH, et al. Macrophage colony-stimulating factor gene transfer into tumor cells induces macrophage infiltration but not tumor suppression. *European journal of immunology*. 1993, vol. 23, no. 1, p. 186-90). It appears that at the high serum contents commonly found in patients suffering from tumors of the breast, ovaries or pancreas, CSF-1 orients the differentiation of these monocytes into macrophages and not into dendritic cells capable of presenting tumoral antigens and thus initiating an efficient cytotoxic immune response directed against tumor cells (SCHOLL. Circulating levels of the macrophage colony stimulating factor CSF-1 in primary and metastatic breast cancer patients. A pilot study. *Breast cancer research and treatment*. 1996, vol. 39, no. 3, p. 275-83; BARON, et al. Modulation of MHC class II transport and lysosome distribution by macrophage-colony stimulating factor in human dendritic cells derived from monocytes. *Journal of cell science*. 2001, vol. 114, no. pt5, p. 999-1010).

CSF-1 is also essential for proliferation and differentiation of osteoclasts (CECCHINI, et al. Role of CSF-1 in bone and bone marrow development. *Molecular reproduction and development*. 1997, vol. 46, no. 1, p. 75-83). Osteoclasts are multinucleated cells that express the CSF-1R, deriving from hematopoietic precursors that are primarily responsible for the degradation of mineralized bone during bone development, homeostasis and repair. In various skeletal disorders such as osteoporosis, hypercalcemia of malignancy, rheumatoid arthritis, tumor metastases and Paget's disease, bone resorption by osteoclasts exceeds bone formation by osteoblasts leading to decreased bone mass, skeletal fragility and bone fracture (BRUZZANITI, et al. Molecular regulation of osteoclast activity. *Reviews in endocrine*. 2006, vol. 7, no. 1-2, p. 123-39). For example, patients with advanced breast cancer frequently develop metastasis to bone. Bone metastasis results in intractable pain and a high risk of fractures due to tumor-driven bone loss (osteolysis), which is caused by increased osteoclast activity (CICEK, et al. Breast cancer bone metastasis and current small therapeutics. *Cancer metastasis reviews*. 2006, vol. 25, no. 4, p. 635-44). It has been shown that osteolysis is linked to a high level of circulating CSF-1 (KITAURA, et al. The journal of clinical investigation. *M-CSF mediates TNF-induced inflammatory osteolysis*. 2005, vol. 115, no. 12, p. 3418-27).

The CSF-1 pathway is also involved in mediating intestinal inflammation in disease such as Inflammatory bowel disease (MARSHALL, et al. Blockade of colony stimulating factor-1 (CSF-I) leads to inhibition of DSS-induced colitis. *Inflammatory bowel diseases*. 2007, vol. 13, no. 2, p. 219-24), in mediating macrophage proliferation during acute allograft rejection (JOSE, et al. Blockade of macrophage colony-stimulating factor reduces macrophage proliferation and accumulation in renal allograft rejection. *American journal of transplantation*. 2003, vol. 3, no. 3, p. 294-300. and in HIV-1 replication in infected macrophage (KUTZA, et al. Macrophage colony-stimulating factor antagonists inhibit replication of HIV-1 in human macrophages. *Journal of immunology*. 2000, no. 164, p. 4955-4960.

For these reasons, the inhibition of the CSF-1 activity by various compounds has been proposed for the treatment of cancer and bone degradation.

BACKGROUND ART

WO 01/30381 relates to the use of inhibitors of the CSF-1 activity in the production of medicaments for the treatment of tumor diseases. The two proposed approaches for the inhibition of the CSF-1 activity are the suppression of the CSF-1 activity itself, and the suppression of the activity of the CSF-1R. Neutralizing antibodies against CSF-1 or its receptor are preferred as the inhibitors of CSF-1 activity.

WO 03/059395 describes combination products comprising a substance capable of inhibiting CSF-1 activity and a substance having a cytotoxic activity for the treatment of cancer.

WO 2005/068503 discloses a method for preventing and treating osteolysis, cancer metastasis and bone loss associated with cancer metastasis by administering an antibody against CSF-1 to a subject.

EP 1488792 A relates to the use of mono- and/or bicyclic aryl or heteroaryl quinazoline compounds which exhibit selective inhibition of differentiation, proliferation or mediator release by effectively inhibiting CSF-1R tyrosine kinase activity. This application also relates to the use of such compounds for the manufacture of a medicament for inhibiting abnormal cell proliferation.

US 2005059113 relates to antibodies and antigen-binding portions thereof that specifically bind to aCSF-1. The invention also relates to human anti-CSF-1 antibodies and antigen-binding portions thereof. This application invention also provides gene therapy methods using nucleic acid molecules encoding the heavy and/or light immunoglobulin molecules that comprise the human anti-CSF-1 antibodies.

Roussel and Sherr, 1989, PNAS, 86, 7924-7927 and Ashmun et al., 1989, Blood, 73, 827-837 are disclosing monoclonal antibodies to the human CSF-1 receptor (e.g. 12-3A3 and 2-4A5) which specifically block CSF-1 binding to the human receptor, thereby inhibiting ligand-dependent growth. The recognized epitope has been localized between positions amino acids 349-512.

WO2009/026303 provides antigen binding proteins that are able to compete with CSF-1 and therefore prevent CSF-1 from binding to its receptor, and in certain embodiments inhibit binding between IL-34 and CSF-1R. Moreover the experimental section of WO2009/026303 indicates that the antibodies developed by the Inventors are binding epitopes that are mainly located at the N-terminus between amino acids 20 to 223 of SEQ ID NO 29 (corresponding to Ig-like loop 1 and Ig-like loop 2 in WO2009/026303) of CSF-1R and require the presence of both the Ig-like loop 1 and Ig-like loop 2 regions.

DISCLOSURE OF INVENTION

The present invention relates to an antibody that specifically binds to the CSF-1R, and more specifically to human CSF-1R.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, the terms "comprising" and "comprise" are intended to mean that the kits of parts, products, compositions and methods include the referenced components or steps, but not excluding others. "Consisting essentially of"

when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "specifically binds to" refers to a binding reaction which is determinative of the presence of a target protein in the presence of a heterogeneous population of proteins and other biologics. Thus, under designated assay conditions, the antibody according to the invention bind preferentially to at least part of the CSF-1R and do not bind in a significant amount to other components present in a test sample. Specific binding between the antibody according to the invention and the CSF-1R target means that the binding affinity is of at least $10^3$ $M^{-1}$, and preferably $10^5$ $M^{-1}$, $10^6$ $M^{-1}$, $10^7$ $M^{-1}$, $10^8$ $M^{-1}$, $10^9$ $M^{-1}$ or $10^{10}$ $M^{-1}$. In particularly advantageous embodiment, the binding affinity is of at least $10^9$ $M^{-1}$ or $10^{10}$ $M^{-1}$.

As used herein, the term "CSF-1R" refers to the human CSF1 receptor. The human CSF-1 receptor has been sequenced and its amino acid sequence is depicted in SEQ ID NO: 29.

As used herein, "antibody" or "Ab" is used in the broadest sense. Therefore, an "antibody" or "Ab" can be naturally occurring or man-made such as monoclonal antibodies (mAbs) produced by conventional hybridoma technology, recombinant technology and/or a functional fragment thereof. Antibodies of the present invention are meant to include both intact immunoglobulin molecules for example a polyclonal antibody, a monoclonal antibody (mAb), a monospecific antibody, a bispecific antibody, a polyspecific antibody, a human antibody, an animal antibody (e.g. camelid antibody), chimeric antibodies, as well as portions, fragments, regions, peptides and derivatives thereof (provided by any known technique, such as, but not limited to, enzymatic cleavage, peptide synthesis, or recombinant techniques), such as, for example, immunoglobulin devoid of light chains (see for example U.S. Pat. No. 6,005,079), Fab, Fab', F (ab')$_2$, Fv, scFv, antibody fragment, diabody, Fd, CDR regions, or any portion or peptide sequence of the antibody that is capable of binding antigen or epitope. An antibody is said to be "capable of binding" a molecule if it is capable of specifically reacting with the molecule to thereby bind the molecule to the antibody. Antibody fragments or portions may lack the Fc fragment of intact antibody, clear more rapidly from the circulation, and may have less non-specific tissue binding than an intact antibody. Examples of antibody may be produced from intact antibodies using methods well known in the art, for example by proteolytic cleavage with enzymes such as papain (to produce Fab fragments) or pepsin (to produce F(ab')$_2$ fragments (see e.g., Wahl et al., 24 J. Nucl. Med. 316-25 (1983). Portions of antibodies may be made by any of the above methods, or may be made by expressing a portion of the recombinant molecule. For example, the CDR region(s) of a recombinant antibody may be isolated and subcloned into the appropriate expression vector.

As used herein, the term "variable region" refers to the variable region, or domain, of the light chain (VL) or heavy chain (VH) which contain the determinants for binding recognition specificity. The variable domains are involved in antigen recognition and form the antigen binding site. As used herein, the term "framework region" refers to portions of light and heavy chain variable regions that are at least 85% homologous (i.e., other than the CDR's) among different antibodies in the same species. As used herein, the term "homologous>>" refers to a comparison of the amino acids of two polypeptides which, when aligned by using the Smith-Waterman algorithm (SMITH, et al. Identification of common molecular subsequences. *Journal of Molecular Biology.* 1981, no. 147, p. 195-7), have approximately the designated percentage of the same amino acids. For example, "85% homologous" refers to a comparison of the amino acids of two polypeptides which when optimally aligned have 85% amino acid identity. The variable region of both the heavy and light chain is divided into segments comprising four framework sub-regions (FR1, FR2, FR3, and FR4), interrupted by three stretches of hypervariable sequences, or the complementary determining regions (CDR's), as defined in Kabat's database (Kabat et al., op. cit.), with the CDR1 positioned between FR1 and FR2, CDR2 between FR2 and FR3, and CDR3 between FR3 and FR4. Without specifying the particular sub-regions as FR1, FR2, FR3 or FR4, a framework region as referred by others, represents the combined FR's within the variable region of a single, naturally occurring immunoglobulin chain. As used herein, a FR represents one of the four sub-regions, and FR's represents two or more of the four sub-regions constituting a framework region. The sequences of the framework regions of different light or heavy chains are relatively conserved within a species. The framework region of an antibody is the combined framework regions of the constituent light and heavy chains and serves to position and align the CDR's. The CDR's are primarily responsible for forming the binding site of an antibody conferring binding specificity and affinity to an epitope of an antigen. Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure. The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The accepted CDR regions have been described by Kabat et al, 252 J. Biol. Chem. 6609-16 (1977), and CDR loops may be identified by applying these rules during an examination of a linear amino acid sequence. The rules for defining the CDR-H3 loop can vary, however (see Chapter 4, Antibody Engineering: Methods & Protocols, (Lo, ed. Humana Press, Totowa, N.J., 2004)), and the actual boundaries of some CDR-H3 loops may not be identified without experimental techniques such as circular dichroism, nuclear magnetic resonance, or X-ray crystallography. In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs. The CDR regions can also be defined using Chothia nomenclature (CHOTHIA and LESK. Canonical structures for the hypervariable regions of immunoglobulins (1987) J Mol. Biol. 1987 Aug. 20; 196(4):901-17). Therefore, in certain embodiments, the CDRs are Kabat defined CDRs, and in other embodiments, the CDRs are Chothia defined CDRs. Regarding the antigenic determinate recognized by the CDR regions of the antibody, this is also referred to as the "epitope." In other words, epitope refers to that portion of any molecule capable of being recognized by, and bound by, an antibody (the corresponding antibody binding region may be referred to as a paratope). In general, epitopes consist of chemically active surface groupings of molecules, for example, amino acids or sugar side chains, and have specific three-dimensional structural characteristics as well as specific charge characteristics.

The term "monoclonal antibody" or "mAb" as used herein refers to an antibody that is derived from a single clone. Monoclonal antibodies can be prepared using hybridoma techniques such as those disclosed in HARLOW. Antibodies: A Laboratory manual. 2nd edition. Cold Spring Harbor: Laboratory press, 1988 and HAMMERLING, et al. Monoclonal Antibodies and T Cell Hybridomas. New York: Elsevier, 1981. p. 563-681.

As used herein, the term "human antibody" refers to an antibody having variable and constant regions derived from or closely matching human germline immunoglobulin sequences. The human antibody of the invention may include amino acid residues not encoded by human germline immunoglobulin sequences (e.g., mutations introduced by random or site-specific mutagenesis in vitro or by somatic mutation in vivo). Thus, as used herein, the term "human antibody" refers to an antibody in which substantially every part of the protein is substantially similar to a human germline antibody. "Substantially similar" refers to an antibody having a nucleic acid sequence which is at least 80, preferably 85, more preferably 90 and even more preferably 95% homologous to the nucleic acid sequence a human germline antibody.

As used herein, the term "Fab" refers to regions of antibody molecules which include the variable region of the heavy chain and light chain and which exhibit binding activity. "Fab" includes aggregates of one heavy and one light chain (commonly known as Fab), whether any of the above are covalently or non-covalently aggregated so long as the aggregation is capable of selectively reacting with a particular antigen or antigen family. The Fab fragment is a heterodimer comprising a VL and a second polypeptide comprising the VH and CH1 domains. In a preferred embodiment the antibody is an Fab' fragment. By Fab' fragments differ from Fab fragments in that the Fab' fragment contains a few residues at the carboxy terminus of the heavy chain CH1 domain including one or more cysteines from the antibody "hinge region".

"F(ab')$_2$" refers to an antibody fragment obtained by the pepsin treatment of an antibody or to the equivalent protein obtained by other techniques such as recombinant technologies. F(ab')$_2$ fragment has two antigen-combining sites and is still capable of cross-linking an antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Single-chain Fv" or "scFv" comprise the VH and VL domains of antibody, wherein these domains are present in a single polypeptide chain. Preferably, the scFv further comprises a polypeptide linker between the VH and VL domains which enables the scFv to form the desired structure for antigen binding (LENNARD. Standard protocols for the construction of scFv libraries. *Methods in molecular biology*. 2002, no. 178, p. 59-71).

As used herein, the term "antibody fragment" refers to one or more fragments of an antibody that retain the ability to specifically bind to the CSF-1R.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies may bind to one or more than one epitope. Diabodies are more fully described in POLAK. Production and structure of diabodies. *Structure*. 1994, vol. 2, no. 12, p. 1121-3, HUDSON, et al. High avidity scFv multimers; diabodies and triabodies. *Journal of immunological methods*. 1999, vol. 231, no. 1-2, p. 177-89 and KIPRIYANOV. Generation of bispecific and tandem diabodies. *Methods in molecular biology*. 2002, no. 178, p. 317-31.

Various techniques have been developed for the production of antibody fragments. Traditionally, these fragments were derived via proteolytic digestion of intact antibodies. However, these fragments can now be produced directly by recombinant host cells. Fab, Fv and scFv antibody fragments can all be expressed in and secreted from *E. coli*, thus allowing the production of large amounts of these fragments. Techniques for the production of antibody fragments will be apparent to the skilled in the art. In other embodiments, the antibody of choice is a single chain Fv fragment (scFv).

As used herein "Domain Antibodies" (dAbs) consist in the smallest functional binding units of antibodies, corresponding to the variable regions of either the heavy (VH) or light (VL) chains of the antibodies. Domain Antibodies have a molecular weight of approximately 13 kDa, or less than one-tenth the size of a full antibody.

As used herein, "Fd" refers to an antibody fragment that consists of the VH and CH1 domains.

The term "antibody" or "Ab" also refers to other antibody fragment well known to the one skilled in the art, for example those described in HOLLIGER, et al. Engineered antibody fragments and the rise of single domains. *Nature biotechnology*. 2005, vol. 23, no. 9, p. 1126-36 and HOOGENBOOM, et al. Natural and designer binding sites made by phage display technology. *Immunology today*. 2000, vol. 21, no. 8, p. 371-8.

According to one embodiment, the antibody of the Invention binds specifically to CSF-1R, and more specifically to human CSF-1R, and comprises:
(i) at least one CDR wherein said CDR is comprising at least five consecutive amino acids of the sequence starting in position 45 and finishing in position 54 of SEQ ID NO:2, of the sequence starting in position 66 and finishing in position 87 of SEQ ID NO:2 or of the sequence starting in position 117 and finishing in position 126 of SEQ ID NO:2;
or,
(ii) at least one CDR wherein said CDR is comprising at least five consecutive amino acids of the sequence starting in position 44 and finishing in position 56 of SEQ ID NO:4, of the sequence starting in position 66 and finishing in position 76 of SEQ ID NO:4 or of the sequence starting in position 109 and finishing in position 117 of SEQ ID NO:4.

According to another embodiment, the antibody of the Invention binds specifically to CSF-1R, and more specifically to human CSF-1R, and comprises at least one CDR wherein said CDR is, independently from one another, selected in the group of CDRs comprising at least five consecutive amino acids:
- of the sequence starting in position 45 and finishing in position 54 of SEQ ID NO:2,
- of the sequence starting in position 66 and finishing in position 87 of SEQ ID NO:2,
- of the sequence starting in position 117 and finishing in position 126 of SEQ ID NO:2,
- of the sequence starting in position 44 and finishing in position 56 of SEQ ID NO:4,
- of the sequence starting in position 66 and finishing in position 76 of SEQ ID NO:4
- or of the sequence starting in position 109 and finishing in position 117 of SEQ ID NO:4.

According to a preferred embodiment, the antibody of the Invention binds specifically to CSF-1R, and more specifically to human CSF-1R, and comprises 2, 3, 4 or 5 and even more preferably 6 CDRs wherein said CDRs are, independently from one another, selected in the group of CDRs comprising at least five consecutive amino acids:
- of the sequence starting in position 45 and finishing in position 54 of SEQ ID NO:2,
- of the sequence starting in position 66 and finishing in position 87 of SEQ ID NO:2,
- of the sequence starting in position 117 and finishing in position 126 of SEQ ID NO:2,
- of the sequence starting in position 44 and finishing in position 56 of SEQ ID NO:4,
- of the sequence starting in position 66 and finishing in position 76 of SEQ ID NO:4
- or of the sequence starting in position 109 and finishing in position 117 of SEQ ID NO:4.

According to a another preferred embodiment, the antibody of the Invention binds specifically to CSF-1R, and more specifically to human CSF-1R, and comprises:
(i) 2 and even more preferably 3 CDRs wherein said CDRs are, independently from one another, selected in the group of CDRs comprising at least five consecutive amino acids:
- of the sequence starting in position 45 and finishing in position 54 of SEQ ID NO:2,
- of the sequence starting in position 66 and finishing in position 87 of SEQ ID NO:2,
- of the sequence starting in position 117 and finishing in position 126 of SEQ ID NO:2, or (ii) 2 and even more preferably 3 CDRs wherein said CDRs are, independently from one another, selected in the group of CDRs comprising at least five consecutive amino acids:
- of the sequence starting in position 44 and finishing in position 56 of SEQ ID NO:4,
- of the sequence starting in position 66 and finishing in position 76 of SEQ ID NO:4
- or of the sequence starting in position 109 and finishing in position 117 of SEQ ID NO:4.

According to another embodiment, the antibody of the Invention binds specifically to CSF-1R, and more specifically to human CSF-1R, and comprises:
(i) at least one CDR selected, independently from one another, in the group of the CDR as set forth in:
- the sequence starting in position 45 and finishing in position 54 of SEQ ID NO:2,
- the sequence starting in position 66 and finishing in position 87 of SEQ ID NO:2 and
- the sequence starting in position 117 and finishing in position 126 of SEQ ID NO:2;

or (ii) at least one CDR selected, independently from one another, in the group of the CDR as set forth in:
- the sequence starting in position 44 and finishing in position 56 of SEQ ID NO:4,
- the sequence starting in position 66 and finishing in position 76 of SEQ ID NO:4 and
- the sequence starting in position 109 and finishing in position 117 of SEQ ID NO:4.

According to another embodiment, the antibody of the Invention binds specifically to CSF-1R, and more specifically to human CSF-1R, and comprises at least one CDR selected, independently from one another, in the group of the CDR as set forth in:
- the sequence starting in position 45 and finishing in position 54 of SEQ ID NO:2,
- the sequence starting in position 66 and finishing in position 87 of SEQ ID NO:2,
- the sequence starting in position 117 and finishing in position 126 of SEQ ID NO:2,
- the sequence starting in position 44 and finishing in position 56 of SEQ ID NO:4,
- the sequence starting in position 66 and finishing in position 76 of SEQ ID NO:4 and
- the sequence starting in position 109 and finishing in position 117 of SEQ ID NO:4.

According to another embodiment, the antibody of the Invention binds specifically to CSF-1R, and more specifically to human CSF-1R, and comprises 2, 3, 4 or 5 and even more preferably 6 CDRs selected, independently from one another, in the group of the CDR as set forth in:
- the sequence starting in position 45 and finishing in position 54 of SEQ ID NO:2,
- the sequence starting in position 66 and finishing in position 87 of SEQ ID NO:2,
- the sequence starting in position 117 and finishing in position 126 of SEQ ID NO:2,
- the sequence starting in position 44 and finishing in position 56 of SEQ ID NO:4,
- the sequence starting in position 66 and finishing in position 76 of SEQ ID NO:4 and
- the sequence starting in position 109 and finishing in position 117 of SEQ ID NO:4.

According to a another preferred embodiment, the antibody of the Invention binds specifically to CSF-1R, and more specifically to human CSF-1R, and comprises:
(i) 2 and even more preferably 3 CDRs wherein said CDRs are, independently from one another, selected in the group of the CDRs as set forth in:
- the sequence starting in position 45 and finishing in position 54 of SEQ ID NO:2,
- the sequence starting in position 66 and finishing in position 87 of SEQ ID NO:2,
- the sequence starting in position 117 and finishing in position 126 of SEQ ID NO:2, or (ii) 2 and even more preferably 3 CDRs wherein said CDRs are, independently from one another, selected in the group of the CDRs as set forth in:
- the sequence starting in position 44 and finishing in position 56 of SEQ ID NO:4, the sequence starting in position 66 and finishing in position 76 of SEQ ID NO:4, the sequence starting in position 109 and finishing in position 117 of SEQ ID NO:4.

According to one embodiment, the antibody of the Invention binds specifically to CSF-1R, and more specifically to human CSF-1R, and comprises (i) at least one CDR comprising an amino acid sequence as set forth in any one of SEQ ID NOs: 11, 12, or 13; or (ii) at least one CDR comprising an amino acid sequence as set forth in any one of SEQ ID NOs: 14, 15 or 16.

According to another embodiment, the antibody of the Invention binds specifically to CSF-1R, and more specifically to human CSF-1R, and comprises at least one CDR comprising an amino acid sequence as set forth in any one of SEQ ID NOs: 11, 12, 13, 14, 15 or 16.

According to a preferred embodiment, the antibody of the Invention binds specifically to CSF-1R, and more specifically to human CSF-1R, and comprises 2, 3, 4, 5 and even more preferably 6 CDRs comprising an amino acid sequence as set forth in any one of SEQ ID NOs: 11, 12, 13, 14, 15 or 16.

According to another embodiment, the antibody of the Invention binds specifically to CSF-1R, and more specifically to human CSF-1R, and comprises (i) at least one CDR as set forth in any one of SEQ ID NOs: 11, 12 or 13; or (ii) at least one CDR set forth in any one of SEQ ID NOs: 14, 15 or 16.

According to another embodiment, the antibody of the Invention binds specifically to CSF-1R, and more specifically to human CSF-1R, and comprises at least one CDR as set forth in any one of SEQ ID NOs: 11, 12, 13, 14, 15 or 16.

According to one preferred embodiment, the antibody of the Invention binds specifically to CSF-1R, and more specifically to human CSF-1R, and comprises 2, 3, 4, 5 and even more preferably 6 CDRs as set forth in any one of SEQ ID NOs: 11, 12, 13, 14, 15 or 16.

According to another embodiment, the antibody of the Invention binds specifically to CSF-1R, and more specifically to human CSF-1R, and comprises (i) at least one CDR comprising an amino acid sequence as set forth in any one of SEQ ID NOs: 17, 18 or 19; or (ii) at least one CDR comprising an amino acid sequence as set forth in any one of SEQ ID NOs: 20, 21 or 22.

According to another embodiment, the antibody of the Invention binds specifically to CSF-1R, and more specifically to human CSF-1R, and comprises at least one CDR comprising an amino acid sequence as set forth in any one of SEQ ID NOs: 17, 18, 19, 20, 21 or 22.

According to one preferred embodiment, the antibody of the Invention binds specifically to CSF-1R, and more specifically to human CSF-1R, and comprises 2, 3, 4, 5 and even more preferably 6 CDRs comprising an amino acid sequence as set forth in any one of SEQ ID NOs: 17, 18, 19, 20, 21 or 22.

According to another embodiment, the antibody of the Invention binds specifically to CSF-1R, and more specifically to human CSF-1R, and comprises (i) at least one CDR as set forth in any one of SEQ ID NOs: 17, 18 or 19; or (ii) at least one CDR as set forth in any one of SEQ ID NOs: 20, 21 or 22.

According to another embodiment, the antibody of the Invention binds specifically to CSF-1R, and more specifically to human CSF-1R, and comprises at least one CDR set forth in any one of SEQ ID NOs: 17, 18, 19, 20, 21 or 22.

According to one preferred embodiment, the antibody of the Invention binds specifically to CSF-1R, and more specifically to human CSF-1R, and comprises 2, 3, 4, 5 and even more preferably 6 CDRs as set forth in any one of SEQ ID NOs: 17, 18, 19, 20, 21 or 22.

According to another embodiment, the antibody of the Invention binds specifically to CSF-1R, and more specifically to human CSF-1R, and comprises (i) at least one CDR comprising an amino acid sequence as set forth in any one of SEQ ID NOs: 23, 24 or 25; or (ii) at least one CDR comprising an amino acid sequence as set forth in any one of SEQ ID NOs: 26, 27 or 28.

According to another embodiment, the antibody of the Invention binds specifically to CSF-1R, and more specifically to human CSF-1R, and comprises at least one CDR comprising an amino acid sequence as set forth in any one of SEQ ID NOs: 23, 24, 25, 26, 27 or 28.

According to one preferred embodiment, the antibody of the Invention binds specifically to CSF-1R, and more specifically to human CSF-1R, and comprises 2, 3, 4, 5 and even more preferably 6 CDRs comprising an amino acid sequence as set forth in any one of SEQ ID NOs: 23, 24, 25, 26, 27 or 28.

According to another embodiment, the antibody of the Invention binds specifically to CSF-1R, and more specifically to human CSF-1R, and comprises (i) at least one CDR as set forth in any one of SEQ ID NOs: 23, 24 or 25; or (ii) at least one CDR as set forth in any one of SEQ ID NOs: 26, 27 or 28.

According to another embodiment, the antibody of the Invention binds specifically to CSF-1R, and more specifically to human CSF-1R, and comprises at least one CDR as set forth in any one of SEQ ID NOs: 23, 24, 25, 26, 27 or 28.

According to one preferred embodiment, the antibody of the Invention binds specifically to CSF-1R, and more specifically to human CSF-1R, and comprises 2, 3, 4, 5 and even more preferably 6 CDRs as set forth in any one of SEQ ID NOs: 23, 24, 25, 26, 27 or 28.

According to another embodiment, the antibody of the Invention binds specifically to CSF-1R, and more specifically to human CSF-1R, and comprises a variable region, wherein said variable region comprises the CDRs as set forth in:

the sequence starting in position 45 and finishing in position 54 of SEQ ID NO:2, the sequence starting in position 66 and finishing in position 87 of SEQ ID NO:2 and the sequence starting in position 117 and finishing in position 126 of SEQ ID NO:2.

According to another embodiment, the antibody of the Invention binds specifically to CSF-1R, and more specifically to human CSF-1R, and comprises a variable region, wherein said variable region comprises the CDRs as set forth in:

the sequence starting in position 44 and finishing in position 56 of SEQ ID NO:4, the sequence starting in position 66 and finishing in position 76 of SEQ ID NO:4 and the sequence starting in position 109 and finishing in position 117 of SEQ ID NO:4.

According to another embodiment, the antibody of the Invention binds specifically to CSF-1R, and more specifically to human CSF-1R, and comprises a variable region, wherein said variable region comprises the three CDRs as set forth in SEQ ID NOs: 11, 12, and 13.

According to another embodiment, the antibody of the Invention binds specifically to CSF-1R, and more specifically to human CSF-1R, and comprises a variable region, wherein said variable region comprises the three CDRs as set forth in SEQ ID NOs: 14, 15, and 16.

According to another embodiment, the antibody of the Invention binds specifically to CSF-1R, and more specifically to human CSF-1R, and comprises a variable region, wherein said variable region comprises the three CDRs set forth in SEQ ID NOs: 17, 18, and 19.

According to another embodiment, the antibody of the Invention binds specifically to CSF-1R, and more specifically to human CSF-1R, and comprises a variable region, wherein said variable region comprises the three CDRs as set forth in SEQ ID NOs: 20, 21, and 22.

According to another embodiment, the antibody of the Invention binds specifically to CSF-1R, and more specifically to human CSF-1R, and comprises a variable region, wherein said variable region comprises the three CDRs as set forth in SEQ ID NOs: 23, 24, and 25.

According to another embodiment, the antibody of the Invention binds specifically to CSF-1R, and more specifically to human CSF-1R, and comprises a variable region, wherein said variable region comprises the three CDRs as set forth in SEQ ID NOs: 26, 27, and 28.

In preferred embodiments, the said variable region further comprises one, more preferably two, even more preferably three and definitely preferably four framework region, and more preferably human FR. As used herein, a "human FR" is a framework region that is at least 75% homologous to the framework region of a naturally occurring human antibody.

According to one preferred embodiment, the antibody of the Invention binds specifically to CSF-1R and comprises a variable region, wherein the variable region comprises an amino acid sequence as set forth in SEQ ID NO:6.

In a more preferred embodiment, the antibody of the Invention binds specifically to CSF-1R and comprises a variable region, wherein the variable region is as set forth in SEQ ID NO:6.

In another preferred embodiment, the antibody of the Invention binds specifically to CSF-1R and comprises a variable region, wherein the variable region comprises an amino acid sequence as set forth in SEQ ID NO:9.

In another more preferred embodiment, the antibody of the Invention binds specifically to CSF-1R and comprises a variable region, wherein the variable region is as set forth in SEQ ID NO:9.

In another embodiment, the antibody of the Invention binds specifically to CSF-1R and comprises two variable regions, wherein the variable regions are, independently from one another, selected in the group of
(i) variable regions comprising the CDRs as set forth in:
the sequence starting in position 45 and finishing in position 54 of SEQ ID NO:2,
the sequence starting in position 66 and finishing in position 87 of SEQ ID NO:2 and
the sequence starting in position 117 and finishing in position 126 of SEQ ID NO:2;
(ii) variable regions comprising the CDR as set forth in:
the sequence starting in position 44 and finishing in position 56 of SEQ ID NO:4,
the sequence starting in position 66 and finishing in position 76 of SEQ ID NO:4 and
the sequence starting in position 109 and finishing in position 117 of SEQ ID NO:4;
(iii) variable regions comprising the three CDRs set forth in SEQ ID NOs: 11, 12, and 13;
(iv) variable regions comprising the three CDRs set forth in SEQ ID NOs: 14, 15, and 16;
(v) variable regions comprising the three CDRs set forth in SEQ ID NOs: 17, 18, and 19;
(vi) variable regions comprising the three CDRs set forth in SEQ ID NOs: 20, 21, and 22;
(vii) variable regions comprising the three CDRs set forth in SEQ ID NOs: 23, 24, and 25
and
(viii) variable regions comprising the three CDRs set forth in SEQ ID NOs: 26, 27 and 28.

According to a preferred embodiment, the antibody of the Invention binds specifically to CSF-1R and comprises:
(i) a first variable region, wherein said variable region comprises:
the CDR as set forth in the sequence starting in position 45 and finishing in position 54 of SEQ ID NO:2,
the CDR as set forth in the sequence starting in position 66 and finishing in position 87 of SEQ ID NO:2 and
the CDR as set forth in the sequence starting in position 117 and finishing in position 126 of SEQ ID NO:2;
and
(ii) a second variable region, wherein said variable region comprises:
the CDR as set forth in the sequence starting in position 44 and finishing in position 56 of SEQ ID NO:4,
the CDR as set forth in the sequence starting in position 66 and finishing in position 76 of SEQ ID NO:4 and
the CDR as set forth in the sequence starting in position 109 and finishing in position 117 of SEQ ID NO:4.

According to a preferred embodiment, the antibody of the Invention binds specifically to CSF-1R and comprises:
a variable region comprising the three CDRs as set forth in SEQ ID NOs: 11, 12, and 13, and
a variable region comprising the three CDRs as set forth in SEQ ID NOs: 14, 15, and 16.

According to a preferred embodiment, the antibody of the Invention binds specifically to CSF-1R and comprises:
a variable region comprising the three CDRs as set forth in SEQ ID NOs: 17, 18, and 19, and
a variable region comprising the three CDRs as set forth in SEQ ID NOs: 20, 21, and 22.

According to a preferred embodiment, the antibody of the Invention binds specifically to CSF-1R and comprises:
a variable region comprising the three CDRs as set forth in SEQ ID NOs: 23, 24, and 25, and
a variable region comprising the three CDRs as set forth in SEQ ID NOs: 26, 27, and 28.

According to a preferred embodiment, the antibody of the Invention binds specifically to CSF-1R and comprises:
a variable region as set forth in SEQ ID NO:6 and a variable region as set forth in SEQ ID NO:9.

According to a preferred embodiment, the antibody of the Invention binds specifically to CSF-1R and comprises:
(i) a heavy-chain variable region comprising:
the CDR as set forth in the sequence starting in position 45 and finishing in position 54 of SEQ ID NO:2,
the CDR as set forth in the sequence starting in position 66 and finishing in position 87 of SEQ ID NO:2 and
the CDR as set forth in the sequence starting in position 117 and finishing in position 126 of SEQ ID NO:2;
and
(ii) a light-chain variable region comprising:
the CDR as set forth in the sequence starting in position 44 and finishing in position 56 of SEQ ID NO:4,
the CDR as set forth in the sequence starting in position 66 and finishing in position 76 of SEQ ID NO:4 and the CDR as set forth in the sequence starting in position 109 and finishing in position 117 of SEQ ID NO:4.

According to another embodiment, the antibody of the Invention binds specifically to CSF-1R and comprises (i) a heavy-chain variable region comprising the three CDRs as set forth in SEQ ID NOs: 11, 12, and 13, and (ii) a light-chain variable region comprising the three CDRs as set forth in SEQ ID NOs: 14, 15, and 16.

According to another embodiment, the antibody of the Invention binds specifically to CSF-1R and comprises (i) a heavy-chain variable region comprising the three CDRs as set forth in SEQ ID NOs: 17, 18, and 19, and (ii) a light-chain variable region comprising the three CDRs as set forth in SEQ ID NOs: 20, 21, and 22.

According to another embodiment, the antibody of the Invention binds specifically to CSF-1R and comprises (i) a heavy-chain variable region comprising the three CDRs as set forth in SEQ ID NOs: 23, 24, and 25, and (ii) a light-chain variable region comprising the three CDRs as set forth in SEQ ID NOs: 26, 27, and 28.

According to a preferred embodiment, the antibody of the Invention binds specifically to CSF-1R and comprises (i) a heavy-chain variable region as set forth in SEQ ID NO:6 and (ii) a light-chain variable region as set forth in SEQ ID NO:9.

According to another preferred embodiment, the antibody of the Invention binds specifically to CSF-1R and is a scFv, wherein said scFv comprises:
  (i) a variable regions comprising:
    the CDR as set forth in the sequence starting in position 45 and finishing in position 54 of SEQ ID NO:2,
    the CDR set forth in the sequence starting in position 66 and finishing in position 87 of SEQ ID NO:2 and
    the CDR set forth in the sequence starting in position 117 and finishing in position 126 of SEQ ID NO:2; and
  (ii) a variable region comprising:
    the CDR set forth in the sequence starting in position 44 and finishing in position 56 of SEQ ID NO:4,
    the CDR set forth in the sequence starting in position 66 and finishing in position 76 of SEQ ID NO:4 and
    the CDR set forth in the sequence starting in position 109 and finishing in position 117 of SEQ ID NO:4.

According to another preferred embodiment, the antibody of the Invention binds specifically to CSF-1R and is a scFv, wherein said scFv comprises:
  a variable region comprising the three CDRs as set forth in SEQ ID NOs: 11, 12, and 13, and
  a variable region comprising the three CDRs as set forth in SEQ ID NOs: 14, 15, and 16.

According to another preferred embodiment, the antibody of the Invention binds specifically to CSF-1R and is a scFv, wherein said scFv comprises:
  a variable region comprising the three CDRs as set forth in SEQ ID NOs: 17, 18, and 19, and
  a variable region comprising the three CDRs as set forth in SEQ ID NOs: 20, 21, and 22.

According to another preferred embodiment, the antibody of the Invention binds specifically to CSF-1R and is a scFv, wherein said scFv comprises
  a variable region comprising the three CDRs as set forth in SEQ ID NOs: 23, 24, and 25, and
  a variable region comprising the three CDRs as set forth in SEQ ID NOs: 26, 27, and 28.

According to a more preferred embodiment, the antibody of the Invention binds specifically to CSF-1R and is a scFv, wherein said scFv comprises:
  a variable region as set forth in SEQ ID NO:6 and
  a variable region as set forth in SEQ ID NO:9.

According to another preferred embodiment, the antibody of the Invention binds specifically to CSF-1R and is a scFv, wherein said scFv comprises:
  (i) a heavy-chain variable region comprising:
    the CDR set forth in the sequence starting in position 45 and finishing in position 54 of SEQ ID NO:2,
    the CDR set forth in the sequence starting in position 66 and finishing in position 87 of SEQ ID NO:2 and
    the CDR set forth in the sequence starting in position 117 and finishing in position 126 of SEQ ID NO:2 and
  (ii) a light-chain variable region comprising:
    the CDR set forth in the sequence starting in position 44 and finishing in position 56 of SEQ ID NO:4,
    the CDR set forth in the sequence starting in position 66 and finishing in position 76 of SEQ ID NO:4 and
    the CDR set forth in the sequence starting in position 109 and finishing in position 117 of SEQ ID NO:4.

According to another preferred embodiment, the antibody of the Invention binds specifically to CSF-1R and is a scFv, wherein said scFv comprises:
  a heavy-chain variable region comprising the three CDRs as set forth in SEQ ID NOs: 11, 12, and 13, and
  a light-chain variable region comprising the three CDRs as set forth in SEQ ID NOs: 14, 15, and 16.

According to another preferred embodiment, the antibody of the Invention binds specifically to CSF-1R and is a scFv, wherein said scFv comprises:
  a heavy-chain variable region comprising the three CDRs as set forth in SEQ ID NOs: 17, 18, and 19, and
  a light-chain variable region comprising the three CDRs as set forth in SEQ ID NOs: 20, 21, and 22.

According to another preferred embodiment, the antibody of the Invention binds specifically to CSF-1R and is a scFv, wherein said scFv comprises:
  a heavy-chain variable region comprising the three CDRs as set forth in SEQ ID NOs: 23, 24, and 25, and
  a light-chain variable region comprising the three CDRs as set forth in SEQ ID NOs: 26, 27, and 28.

According to a more preferred embodiment, the antibody of the Invention binds specifically to CSF-1R and is a scFv, wherein said scFv comprises:
  the heavy-chain variable region as set forth in SEQ ID NO:6 and
  the light-chain variable region as set forth in SEQ ID NO:9.

In an even more preferred embodiment, the scFv is provided wherein at least one amino acid is substituted (according to Table 1 and Table 2) within the amino acid sequence as set forth in SEQ ID NO 6 and 9. In a definitely preferred embodiment the human antibody is provided wherein all the amino acid depicted in Table 1 and Table 2 are substituted (according to Table 1 and Table 2) within the amino acid sequence as set forth in SEQ ID NO 6 and 9.

According to another preferred embodiment, the antibody of the Invention binds specifically to CSF-1R and comprises the heavy chain as set forth in SEQ ID NO:2.

According to another preferred embodiment, the antibody of the Invention binds specifically to CSF-1R and comprises the light chain as set forth in SEQ ID NO:4.

According to a more preferred embodiment, the antibody of the Invention binds specifically to CSF-1R and comprises the heavy chain as set forth in SEQ ID NO:2 and the light chain as set forth in SEQ ID NO:4.

According to an even more preferred embodiment, the antibody of the Invention binds specifically to CSF-1R and comprises two heavy chains as set forth in SEQ ID NO:2 and two light chain as set forth in SEQ ID NO:4. This particular antibody will be named CXIIG6 throughout the present application.

According to another preferred embodiment, the present invention relates to a human antibody, that specifically binds to CSF-1R, comprising:
 (i) a heavy-chain variable region comprising:
  the CDR as set forth in the sequence starting in position 45 and finishing in position 54 of SEQ ID NO:2,
  the CDR as set forth in the sequence starting in position 66 and finishing in position 87 of SEQ ID NO:2 and
  the CDR as set forth in the sequence starting in position 117 and finishing in position 126 of SEQ ID NO:2;
and
 (ii) a light-chain variable region comprising:
  the CDR as set forth in the sequence starting in position 44 and finishing in position 56 of SEQ ID NO:4,
  the CDR as set forth in the sequence starting in position 66 and finishing in position 76 of SEQ ID NO:4 and
  the CDR as set forth in the sequence starting in position 109 and finishing in position 117 of SEQ ID NO:4.

According to another embodiment, the present invention relates to an human antibody, that specifically binds to CSF-1R, comprising:
 a heavy-chain variable region comprising the three CDRs as set forth in SEQ ID NOs: 11, 12, and 13, and
 a light-chain variable region comprising the three CDRs as set forth in SEQ ID NOs: 14, 15, and 16.

According to another embodiment, the present invention relates to an human antibody, that specifically binds to CSF-1R, comprising:
 a heavy-chain variable region comprising the three CDRs as set forth in SEQ ID NOs: 17, 18, and 19, and
 a light-chain variable region comprising the three CDRs as set forth in SEQ ID NOs: 20, 21, and 22.

According to another embodiment, the present invention relates to an human antibody, that specifically binds to CSF-1R, comprising:
 a heavy-chain variable region comprising the three CDRs as set forth in SEQ ID NOs: 23, 24, and 25, and
 a light-chain variable region comprising the three CDRs as set forth in SEQ ID NOs: 26, 27, and 28.

According to a preferred embodiment, the present invention relates to an human antibody, that specifically binds to CSF-1R, comprising:
 the heavy-chain variable region set forth in SEQ ID NO:6 and
 the light-chain variable region set forth in SEQ ID NO:9.

In a more preferred embodiment, the human antibody is provided wherein at least one amino acid is substituted (according to Table 1 and Table 2) within the amino acid sequence as set forth in SEQ ID NO: 6 and 9. In a even more preferred embodiment the human antibody is provided wherein all the amino acid depicted in Table 1 and Table 2 are substituted (according to Table 1 and Table 2) within the amino acid sequence as set forth in SEQ ID NO: 6 and 9.

TABLE 1

| SEQ ID NO: 6 | position | Preferred substitution |
|---|---|---|
| K | 3 | Q |
| E | 5 | V |
| M | 18 | L |

TABLE 1-continued

| SEQ ID NO: 6 | position | Preferred substitution |
|---|---|---|
| K | 19 | R |
| W | 33 | Y |
| S | 40 | A |
| E | 42 | G |
| M | 43 | K |
| A | 49 | G |
| E | 50 | R |
| I | 51 | T |
| A | 59 | T |
| F | 61 | E |
| E | 64 | A |
| S | 79 | N |
| V | 81 | L |
| R | 89 | K |
| P | 90 | T, A |
| G | 94 | A |
| I | 95 | V |
| T | 99 | A |
| N | 107 | Y, V |
| T | 113 | L |
| L | 114 | V |

TABLE 2

| SEQ ID NO: 9 | Position | Preferred substitution |
|---|---|---|
| A | 9 | S |
| V | 13 | A |
| E | 17 | D |
| T | 18 | R |
| E | 27 | Q |
| N | 28 | G |
| Q | 40 | P, D |
| S | 43 | A |
| Q | 45 | K |
| V | 48 | L |
| H | 49 | Y |
| N | 53 | R |
| A | 55 | E |
| D | 56 | S |
| Q | 70 | D |
| Y | 71 | F |
| S | 72 | T |
| K | 74 | T |
| N | 76 | S |
| S | 80 | P |
| G | 84 | A |
| S | 85 | T |
| H | 90 | Q |
| G | 100 | Q |

According to another embodiment, the present invention relates to an isolated, recombinant or purified antibody that specifically binds to CSF-1R, more preferably human CSF-1R, comprising:
(a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has at least five consecutive amino acids of the sequence starting in position 45 and finishing in position 54 of SEQ ID NO:2;
CDR2 has at least five consecutive amino acids of the sequence starting in position 66 and finishing in position 87 of SEQ ID NO:2; and CDR3 has at least five consecutive amino acids of the sequence starting in position 117 and finishing in position 126 of SEQ ID NO:2; and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has at least five consecutive amino acids of the sequence starting in position 44 and finishing in position 56 of SEQ ID NO:4;
CDR2 has at least five consecutive amino acids of the sequence starting in position 66 and finishing in position 76 of SEQ ID NO:4; and
CDR3 has at least five consecutive amino acids of the sequence starting in position 109 and finishing in position 117 of SEQ ID NO:4.

According to another embodiment, the present invention relates to an isolated, recombinant or purified antibody that specifically binds to CSF-1R, comprising:
(a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has an amino acid sequence selected from the group consisting of: SEQ ID NO: 11, 17 and 23;
CDR2 has an amino acid sequence selected from the group consisting of: SEQ ID NO: 12, 18 and 24; and
CDR3 has an amino acid sequence selected from the group consisting of: SEQ ID NO: 13, 19 and 25; and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has an amino acid sequence selected from the group consisting of: SEQ ID NO: 14, 20 and 26;
CDR2 has an amino acid sequence selected from the group consisting of: SEQ ID NO: 15, 21 and 27; and
CDR3 has an amino acid sequence selected from the group consisting of: SEQ ID NO: 16, 22 and 28.

According to another embodiment, the present invention relates to an isolated, recombinant or purified antibody that specifically binds to CSF-1R, more preferably human CSF-1R, comprising any one of the following (i), (ii) or (iii):
(i)
(a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 11;
CDR2 is as set forth in SEQ ID NO: 12; and
CDR3 is as set forth in SEQ ID NO: 13;
and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 14;
CDR2 is as set forth in SEQ ID NO: 15; and
CDR3 is as set forth in SEQ ID NO: 16;
or
(ii) (a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 17;
CDR2 is as set forth in SEQ ID NO: 18; and
CDR3 is as set forth in SEQ ID NO: 19;
and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 20;
CDR2 is as set forth in SEQ ID NO: 21; and
CDR3 is as set forth in SEQ ID NO: 22;
or
(iii) (a) a first variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 is as set forth in SEQ ID NO: 23;
CDR2 is as set forth in SEQ ID NO: 24; and
CDR3 is as set forth in SEQ ID NO: 25;
and
(b) a second variable region being defined by the following formula

FR1-CDR1-FR2-CDR2-FR3-CDR3-FR4 wherein:
FR1, FR2, FR3 and FR4 are each framework regions;
CDR1, CDR2 and CDR3 are each complementarity determining regions;

wherein:
CDR1 is as set forth in SEQ ID NO: 26;
CDR2 is as set forth in SEQ ID NO: 27; and
CDR3 is as set forth in SEQ ID NO: 28.

According to another embodiment, the present invention relates to an isolated, recombinant or purified antibody that specifically binds to CSF-1R, more preferably human CSF-1R, comprising:
  a first variable region comprising the amino acid sequence of SEQ ID NO: 6; and
  a second variable region comprising the amino acid sequence of SEQ ID NO: 9.

According to another embodiment, the present invention relates to an isolated, recombinant or purified antibody that specifically binds to CSF-1R, more preferably human CSF-1R, comprising:
  a first variable region comprising the amino acid sequence of SEQ ID NO: 2; and
  a second variable region comprising the amino acid sequence of SEQ ID NO: 4.

According to another embodiment, the present invention relates to an isolated, recombinant or purified antibody that specifically binds to CSF-1R, more preferably human CSF-1R, comprising:
  an heavy chain selected in the group consisting in SEQ ID NO:37 (see FIGS. 32A through 32H) and SEQ ID NO:38, and
  a light chain selected in the group consisting in SEQ ID NO:39, SEQ ID NO:40 and SEQ ID NO:41.

According to another embodiment, the present invention relates to an isolated, recombinant or purified antibody that specifically binds to CSF-1R, more preferably human CSF-1R, comprising:
  a first variable region selected in the group consisting of SEQ ID NO:42 and SEQ ID NO:43; and
  a second variable region selected in the group consisting of SEQ ID NO:44, SEQ ID NO:45 and SEQ ID NO:46.

According to one preferred embodiment, the present invention relates to an isolated, recombinant or purified antibody that specifically binds to CSF-1R, more preferably human CSF-1R, comprising (a) an heavy chain consisting in SEQ ID NO:37, and (b) a light chain consisting in SEQ ID NO:39.

According to another preferred embodiment, the present invention relates to an isolated, recombinant or purified antibody that specifically binds to CSF-1R, more preferably human CSF-1R, comprising (a) an heavy chain consisting in SEQ ID NO:38, and (b) a light chain consisting in SEQ ID NO:40.

According to one advantageous embodiment, the present invention relates to an isolated, recombinant or purified antibody that specifically binds to CSF-1R, more preferably human CSF-1R, comprising (a) an heavy chain consisting in SEQ ID NO:37, and (b) a light chain consisting in SEQ ID NO:41.

According to one preferred embodiment, the present invention relates to an isolated, recombinant or purified antibody that specifically binds to CSF-1R, more preferably human CSF-1R, comprising (a) first variable region consisting in SEQ ID NO:42, and (b) a second variable region consisting in SEQ ID NO:44.

According to another preferred embodiment, the present invention relates to an isolated, recombinant or purified antibody that specifically binds to CSF-1R, more preferably human CSF-1R, comprising (a) first variable region consisting in SEQ ID NO:43, and (b) a second variable region consisting in SEQ ID NO:45.

According to one advantageous embodiment, the present invention relates to an isolated, recombinant or purified antibody that specifically binds to CSF-1R, more preferably human CSF-1R, comprising (a) first variable region consisting in SEQ ID NO:42, and (b) a second variable region consisting in SEQ ID NO:46.

The antibody, more specifically the human antibody, according to the invention may be of different isotypes, such as IgG, IgA, IgM or IgE. In a preferred embodiment the antibody, more specifically the human antibody, according to the invention is an IgG.

In a related embodiment, the human antibody comprises a modified or unmodified constant region of a human IgG1, IgG2, IgG3 or IgG4. In a preferred embodiment, the constant region is human IgG1 or IgG4, which may optionally be modified to enhance or decrease certain properties.

In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

The desired binding affinity may be retained even though one or more of the amino acids in the antibody are mutated. These variants have at least one amino acid in the antibody replaced by a different residue. According to another embodiment, the present invention provides an antibody that specifically binds to CSF1 as above described in which at least one of the amino acid comprised in the CDR(s) is conservatively substituted. Conservative substitutions are shown in Table 3.

TABLE 3

| Original Amino Acid | Preferred conservative substitution | More preferred conservative substitution |
| --- | --- | --- |
| A | V, L, I | V |
| R | K, Q, N | K |
| N | Q, H, D, K, R | Q |
| D | E, N | E |
| C | S, A | S |
| Q | N, E | N |
| E | D, Q | D |
| G | A | A |
| H | N, Q, K, R | R |
| I | L, V, M, A, F | L |
| L | I, V, M, A, F | I |
| K | R, Q, N | R |
| M | L, F, I | L |
| F | W, L, V, I, A, Y | Y |
| P | A | A |
| S | T | T |
| T | V, S | S |
| W | Y, F | Y |
| Y | W, F, T, S | F |
| V | L, M, F, A | L |

The present invention also relates to a process of modifying the antibody of the invention by affinity maturation.

As used herein, "affinity maturation" refers to the substitution of one or more amino acid comprised in one or more CDRs, said substitution resulting in an improvement in the affinity of the antibody to CSF-1R, compared to a parent antibody which does not possess those substitution(s). Affinity maturation processes are known in the art. See for example methods disclosed in MARKS, et al. By-passing immunization: building high affinity human antibodies by chain shuffling. *Biotechnology*. 1992, vol. 10, no. 7, p.

779-83; BARBAS, et al. In vitro evolution of a neutralizing human antibody to human immunodeficiency virus type 1 to enhance affinity and broaden strain cross-reactivity. *Proceedings of the National Academy of Sciences of the United States of America*. 1994, vol. 91, no. 9, p. 3809-13; SCHIER. Identification of functional and structural amino-acid residues by parsimonious mutagenesis. *Gene*. 1996, vol. 169, no. 2, p. 147-55; YELTON. Affinity maturation of the BR96 anti-carcinoma antibody by codon-based mutagenesis. *J. immunol*. 1995, vol. 155, no. 4, p. 1994-2004; JACKSON, et al. In vitro antibody maturation. Improvement of a high affinity, neutralizing antibody against IL-1 beta. *J. immunol*. 1995, vol. 154, no. 7, p. 3310-9. and HAWKINS, et al. Selection of phage antibodies by binding affinity. Mimicking affinity maturation. *Journal of molecular biology*. 1992, vol. 226, no. 3, p. 889-96.

The present invention also relates to an antibody, which specifically binds to CSF-1R, obtained by affinity maturation as previously described.

In another embodiment, the present invention provides variants of the antibody previously described, having an amino acid sequence which is at least 80%, preferably at least 85%, more preferably at least 90%, and even more preferably at least 98% homologous to the amino acid sequence of the previously described antibody.

In another embodiment, the antibody according to the invention specifically binds to more than one epitope. For example, the antibody according to the invention may bind to two different epitopes of CSF-1R. Alternatively, the antibody according to the invention can be able to bind to CSF-1R and to another molecule. As used herein, antibodies that specifically bind to more than one epitope can be cross-linked antibodies. For example, an antibody can be coupled to avidin, the other to biotin. Cross-linked antibodies may be made using any convenient cross-linking methods well known in the art. Techniques for generating bispecific antibodies from antibody fragments have also been described see for example BRENNAN, et al. Preparation of bispecific antibodies by chemical recombination of monoclonal immunoglobulin G1 fragments. *Science*. 1985, vol. 229, no. 4708, p. 81-3 and SHALABY, et al. Development of humanized bispecific antibodies reactive with cytotoxic lymphocytes and tumor cells overexpressing the HER2 protooncogene. *The Journal of experimental medicine*. 1992, vol. 175, no. 1, p. 217-25; KOSTELNY, et al. Formation of a bispecific antibody by the use of leucine zippers. *J. immunol*. 1992, vol. 148, no. 5, p. 1547-33.

According to a preferred embodiment, the antibody that specifically binds to more than one epitope according to the invention is a diabody.

According to another preferred embodiment, the antibody that specifically binds to more than one epitope according to the invention is a linear antibody as described in ZAPATA, et al. Engineering linear F(ab')2 fragments for efficient production in *Escherichia coli* and enhanced antiproliferative activity. *Protein engineering* 1995, vol. 8, no. 10, p. 1057-62.

In preferred embodiment, the antibody according to the Invention specifically binds to at least one epitope located between position amino acids 20 to 41 of SEQ ID NO:29 (i.e. N-terminal part of the human domain D1). In preferred embodiment, the antibody according to the Invention binds to one epitope located between position amino acids 20 to 41 of SEQ ID NO:29 (i.e. N-terminal part of the human domain D1) and does not bind to any epitope located between position amino acids 42 to 90, and/or between position amino acids 91 to 104, and/or between position amino acids 105 to 199, and/or between position amino acids 200 to 298 of SEQ ID NO:29. According to preferred embodiment, the antibody of the present Invention is able to recognize the minimal epitope located between position amino acids 20 to 41 of SEQ ID NO:29 (i.e. N-terminal part of the human domain D1). According to advantageous embodiment, the antibody of the present Invention is able to recognize and bind to construct pTG18016 (see FIG. 19 and related example).

In preferred embodiment, the antibody according to the Invention does not compete with IL-34 ligand for binding to the CSF-1R receptor. The term "does not compete with IL-34 ligand" as used herein refers to no inhibition of the IL34 ligand to its receptor CSF-1R binding.

In preferred embodiment, the antibody according to the Invention competes partially with CSF-1 ligand for binding to the CSF-1R receptor. The term "competes partially with CSF-1 ligand" as used herein refers to an inhibition of the CSF-1 ligand to its receptor CSF-1R binding which is less than 100%, preferably less than 50%, and even more preferably less than 20%, and advantageously less than 10%. This partial inhibitor only reduces but does not totally exclude ligand binding, the inhibition is called partial inhibition.

In preferred embodiment, the antibody according to the Invention is able to Invention partially prevents binding of CSF1 to its receptor CSF-1R, and is not able to totally inhibit said binding. More particularly, the antibodies according to the Invention are able to decrease the CSF-1 binding to CSF-1R by approximately 5 to 10%. According to special embodiment, said binding decrease is measured as described in the present Experiment Section, by measuring CSF-1 (having an amino acid sequence extending from position 1 to 444 of SEQ ID: 47—see FIG. 21) binding on receptor CSF-1R having an amino acid sequence extending from Ile 20 to Glu 512 of SEQ ID NO:29.

In preferred embodiment, the antibodies according to the Invention are characterized by high affinity binding to CSF1-R. More particularly, the antibodies according to the Invention have a Ki of less than 1 nM, preferably less than 0.8 nM, and more preferably less than 0.6 nM. As a result of such unexpectedly high affinity, the antibodies of the Invention may be administered in less quantity and therefore eliminate potential side effects.

In particular embodiments, an antibody of the present invention is an antagonist antibody, which partially or fully blocks or inhibits a biological activity of a polypeptide or cell to which it specifically or preferentially binds, i.e. a CSF1-R-expressing cells, more preferably a CSF1-R-expressing human cells, and advantageously a CSF1-R-expressing human cancer cells.

According to specific embodiment of the present invention, the antibody of the present invention has at least one of the following advantageous properties:
  In Vitro Test: the antibody according to the Invention does not compete with IL-34 ligand for binding to the CSF-1R receptor;
  In Vitro Test: the antibody according to the Invention competes partially with CSF-1 ligand for binding to the CSF-1R receptor;
  ADCC Test: in the presence of normal human peripheral blood mononuclear cells, the antibody of the present invention exerts antibody-dependent cellular cytotoxicity (ADCC) against CSF1-R-expressing human cells, especially CSF1-R-expressing human cancer cells;

In Vivo Test: the antibody of the present invention exerts antitumor effects against non-human animals bearing CSF1-R-expressing human cancer cells;

In Vivo Test: the antibody of the present invention exerts antitumor effects against animals, including human, bearing CSF1-R-expressing human cancer cells, In Vivo Test: the antibody of the present invention inhibits the CSF-1-dependent proliferation of AML5 cells.

In Vivo Test: the antibody of the present invention partially inhibits CSF-1-dependent phosphorylation of CSF-1R;

In Vivo Test: the antibody of the present invention has no direct agonistic activity on CSF-1R.

The antibody according to the invention may be glycosylated or non-glycosylated.

As used herein, the term "glycosylation" refers to the presence of carbohydrate units that are covalently attached to the antibody.

In another embodiment, the antibody according to the invention is conjugated to a radiosensitizer agent, a receptor and/or a cytotoxic agent As used herein, the term "radiosensitizer" refers to a molecule that makes cells more sensitive to radiation therapy. Radiosensitizer includes, but are not limited to, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine(IUdR), bromodeoxycytidine, fluorodeoxyuridine (FUdR), hydroxyurea and cisplatin.

As used herein, the term "receptor" refers to a compound able to specifically bind to a ligand. According to a preferred embodiment of the invention, the receptor is biotin.

As used herein, the term cytotoxic agent refers to a compound that is directly toxic to cells, preventing their reproduction or growth. According to a preferred embodiment, the cytotoxic agent used in the context of the present invention is chosen from the group comprising cancer therapeutic agent, toxin (e.g., an enzymatically active toxin of bacterial, fungal, plant or animal origin, or fragments thereof), or a radioactive isotope.

In another embodiment, the antibody according to the invention is conjugated to a labeling agent.

As used herein, "a labeling agent" refers to a detectable compound. The labeling agent may be detectable by itself (e.g., radioisotope labels or fluorescent labels) or, in the case of an enzymatic label, may catalyze chemical modification of a substrate compound which is detectable.

As used herein, the term "conjugated" means that the antibody according to the invention and the labeling agent are covalently or non-covalently linked.

"Covalent link" refers to coupling through reactive functional groups, optionally with the intermediary use of a cross linker or other activating agent (see for example HERMANSON. Bioconjugate techniques. Academic press, 1996). The antibody according to the invention and/or the conjugated agent may be modified in order to allow their coupling via, for example, substitution on an activated carbonyl group (including those activated in situ) or on an imidoester, via addition on an unsaturated carbonyl group, by reductive amination, nucleophilic substitution on a saturated carbon atom or on a heteroatom, by reaction on aromatic cycles, In particular, coupling may be done using homobifunctional or heterobifunctional cross-linking reagents. Homobifunctional cross linkers including glutaraldehyde, succinic acid and bis-imidoester like DMS (dimethyl suberimidate) can be used to couple amine groups which may be present on the various moieties. Numerous examples are given in HERMANSON. Bioconjugate techniques. Academic press, 1996. p. 118-228. which are well known by those of the art. Heterobifunctional cross linkers include those having both amine reactive and sulfhydryl-reactive groups, carbonyl-reactive and sulfhydryl-reactive groups and sulfhydryl-reactive groups and photoreactive linkers. Suitable heterobifunctional cross-linkers are, for example, described in HERMANSON. Bioconjugate techniques. Academic press, 1996. p. 229-285. Examples are, for example, SPDP(N-succinimidyl 3-(2-pyridyldithio) propionate), SMBP (succinimidyl-4-(p-maleimidophenyl) butyrate), SMPT (succinimidyloxycarbonyl-α-methyl-α-(2-pyridyldithio)toluene), MBS (m-maleimidobenzoyl-N-hydroxysuccinimide ester), SIAB (N-succinimidyl (4 iodoacetyl) aminobenzoate), GMBS (γ-maleimidobutyryloxy) succinimide ester), SIAX (succinimidyl-6-iodoacetyl amino hexonate, SIAC (succinimidyl-4-iodoacetyl amino methyl), NPIA (p-nitrophenyl iodoacetate). Other examples are useful to couple carbohydrate-containing molecules (e.g. env glycoproteins, antibodies) to sulfydryl-reactive groups. Examples include MPBH (4-(4-N maleimidophenyl) butyric acid hydrazide) and PDPH (4-(N-maleimidomethyl)cyclohexane-1-carboxylhydrazide (M2C2H and 3-2(2-pyridyldithio) proprionyl hydrazide).

According to another embodiment, the present invention relates to a nucleic acid sequence coding the antibody of the invention.

The term "nucleic acid sequence" refers to a linear sequence of nucleotides. The nucleotides are either a linear sequence of polyribonucleotides or polydeoxyribonucleotides, or a mixture of both. Examples of polynucleotides in the context of the present invention include single and double stranded DNA, single and double stranded RNA, and hybrid molecules that have both mixtures of single and double stranded DNA and RNA. Further, the polynucleotides of the present invention may have one or more modified nucleotides.

According to a preferred embodiment of the invention, the nucleic acid sequence according to the invention is comprised in a vector.

The vector can be of plasmid or viral origin and can, where appropriate, be combined with one or more substances which improve the transfectional efficiency and/or stability of the vector. These substances are widely documented in the literature which is available to the skilled person (see, for example, FELGNER, et al. Cationic liposome mediated transfection. *Proceedings of the Western Pharmacology Society*. 1989, vol. 32, p. 115-21; HODGSON, et al. Virosomes: cationic liposomes enhance retroviral transduction. *Nature biotechnology*. 1996, vol. 14, no. 3, p. 339-42; REMY, et al. Gene transfer with a series of lipophilic DNA-binding molecules. *Bioconjugate chemistry*. 1994, vol. 5, no. 6, p. 647-54). By way of non-limiting illustration, the substances can be polymers, lipids, in particular cationic lipids, liposomes, nuclear proteins or neutral lipids. These substances can be used alone or in combination. A combination which can be envisaged is that of a recombinant plasmid vector which is combined with cationic lipids (DOGS, DC-CHOL, spermine-chol, spermidine-chol, etc.), lysophospholipides (for example Hexadecylphosphocholine) and neutral lipids (DOPE).

According to a preferred embodiment, the cationic lipids which can be used in the present invention are the cationic lipids describes in EP 901463 and more preferably pcTG90.

The choice of the plasmids which can be used within the context of the present invention is huge. They can be cloning vectors and/or expression vectors. In a general manner, they are known to the skilled person and, while a number of them are available commercially, it is also possible to construct them or to modify them using the techniques of genetic manipulation. Examples which may be mentioned are the plasmids which are derived from pBR322 (Gibco BRL), pUC (Gibco BRL), pBluescript (Stratagene), pREP4, pCEP4 (Invitrogen) or p Poly (LATHE, et al. Plasmid and bacteriophage vectors for excision of intact inserts. *Gene.* 1987, vol. 57, no. 2-3, p. 193-201). Preferably, a plasmid which is used in the context of the present invention contains an origin of replication which ensures that replication is initiated in a producer cell and/or a host cell (for example, the ColE1 origin will be chosen for a plasmid which is intended to be produced in *E. coli* and the oriP/EBNA1 system will be chosen if it desired that the plasmid should be self-replicating in a mammalian host cell, LUPTON, et al. Mapping genetic elements of Epstein-Barr virus that facilitate extrachromosomal persistence of Epstein-Barr virus-derived plasmids in human cells. *Molecular and cellular biology.* 1985, vol. 5, no. 10, p. 2533-42; YATES, et al. Stable replication of plasmids derived from Epstein-Barr virus in various mammalian cells. *Nature.* 1985, vol. 313, no. 6005, p. 812-5). The plasmid can additionally comprise a selection gene which enables the transfected cells to be selected or identified (complementation of an auxotrophic mutation, gene encoding resistance to an antibiotic, etc.). Naturally, the plasmid can contain additional elements which improve its maintenance and/or its stability in a given cell (cer sequence, which promotes maintenance of a plasmid in monomeric form (SUMMERS, et al. Multimerization of high copy number plasmids causes instability: ColE1 encodes a determinant essential for plasmid monomerization and stability. *Cell.* 1984, vol. 36, no. 4, p. 1097-103, sequences for integration into the cell genome).

With regard to a viral vector, it is possible to envisage a vector which is derived from a poxvirus (vaccinia virus, in particular MVA, canarypoxvirus, etc.), from an adenovirus, from a retrovirus, from a herpesvirus, from an alphavirus, from a foamy virus or from an adenovirus-associated virus. It is possible to use replication competent or replication deficient viral vectors. Preference will be given to using a vector which does not integrate. In this respect, adenoviral vectors and vectors deriving from poxvirus and more preferably vaccinia virus and MVA are very particularly suitable for implementing the present invention.

According to a preferred embodiment, the viral vector according to the invention derives from a Modified Vaccinia Virus Ankara (MVA). MVA vectors and methods to produce such vectors are fully described in European patents EP 83286 and EP 206920, as well as in SUTTER, et al. Nonreplicating vaccinia vector efficiently expresses recombinant genes. *Proc. Natl. Acad. Sci. U.S.A.* 1992, vol. 89, no. 22, p. 10847-51. According to a more preferred embodiment, the nucleic acid sequence according to the invention may be inserted in deletion I, II, III, IV, V and VI of the MVA vector and even more preferably in deletion III (MEYER, et al. Mapping of deletions in the genome of the highly attenuated vaccinia virus MVA and their influence on virulence. *The Journal of general virology.* 1991, vol. 72, no. Pt5, p. 1031-8; SUTTER, et al. A recombinant vector derived from the host range-restricted and highly attenuated MVA strain of vaccinia virus stimulates protective immunity in mice to influenza virus. *Vaccine.* 1994, vol. 12, no. 11, p. 1032-40).

Retroviruses have the property of infecting, and in most cases integrating into, dividing cells and in this regard are particularly appropriate for use in relation to cancer. A recombinant retrovirus according to the invention generally contains the LTR sequences, an encapsidation region and the nucleotide sequence according to the invention, which is placed under the control of the retroviral LTR or of an internal promoter such as those described below. The recombinant retrovirus can be derived from a retrovirus of any origin (murine, primate, feline, human, etc.) and in particular from the MoMuLV (Moloney murine leukemia virus), MVS (Murine sarcoma virus) or Friend murine retrovirus (Fb29). It is propagated in an encapsidation cell line which is able to supply in trans the viral polypeptides gag, pol and/or env which are required for constituting a viral particle. Such cell lines are described in the literature (PA317, Psi CRIP GP+Am-12 etc.). The retroviral vector according to the invention can contain modifications, in particular in the LTRs (replacement of the promoter region with a eukaryotic promoter) or the encapsidation region (replacement with a heterologous encapsidation region, for example the VL3O type) (see U.S. Pat. No. 5,747,323)

Preference will be also given to using an adenoviral vector which lacks all or part of at least one region which is essential for replication and which is selected from the E1, E2, E4 and L1-L5 regions in order to avoid the vector being propagated within the host organism or the environment. A deletion of the E1 region is preferred. However, it can be combined with (an)other modification(s)-/deletion(s) affecting, in particular, all or part of the E2, E4 and/or L1-L5 regions, to the extent that the defective essential functions are complemented in trans by means of a complementing cell line and/or a helper virus. In this respect, it is possible to use second-generation vectors of the state of the art (see, for example, international applications WO 94/28152 and WO 97/04119). By way of illustration, deletion of the major part of the E1 region and of the E4 transcription unit is very particularly advantageous. For the purpose of increasing the cloning capacities, the adenoviral vector can additionally lack all or part of the non-essential E3 region. According to another alternative, it is possible to make use of a minimal adenoviral vector which retains the sequences which are essential for encapsidation, namely the 5' and 3' ITRs (Inverted Terminal Repeat), and the encapsidation region. The various adenoviral vectors, and the techniques for preparing them, are known (see, for example, GRAHAM, et al. Methods in molecular biology. Edited by MURREY. The human press inc, 1991. p. 109-128).

Furthermore, the origin of the adenoviral vector according to the invention can vary both from the point of view of the species and from the point of view of the serotype. The vector can be derived from the genome of an adenovirus of human or animal (canine, avian, bovine, murine, ovine, porcine, simian, etc.) origin or from a hybrid which comprises adenoviral genome fragments of at least two different origins. More particular mention may be made of the CAV-1 or CAV-2 adenoviruses of canine origin, of the DAV adenovirus of avian origin or of the Bad type 3 adenovirus of bovine origin (ZAKHARCHUK, et al. Physical mapping and homology studies of egg drop syndrome (EDS-76) adenovirus DNA. *Archives of virology.* 1993, vol. 128, no. 1-2, p. 171-6; SPIBEY, et al. Molecular cloning and restriction endonuclease mapping of two strains of canine adenovirus type 2. *The Journal of general virology.* 1989, vol. 70, no. Pt 1, p. 165-72; JOUVENNE, et al. Cloning, physical mapping and cross-hybridization of the canine adenovirus types 1 and 2 genomes. *Gene.* 1987, vol. 60, no. 1, p. 21-8; MITTAL, et al. Development of a bovine adenovirus type 3-based expression vector. *The Journal of general virology.*

1995, vol. 76, no. Pt 1, p. 93-102). However, preference will be given to an adenoviral vector of human origin which is preferably derived from a serotype C-adenovirus, in particular a type 2 or 5 serotype C adenovirus.

The term "replication-competent" as used herein refers to a viral vector capable of replicating in a host cell in the absence of any trans-complementation.

According to a preferred embodiment of the invention, the replication competent vector is a replication competent adenoviral vector. These replication competent adenoviral vectors are well known by the one skilled in the art. Among these, adenoviral vectors deleted in the E1b region coding the 55 kD P53 inhibitor, as in the ONYX-015 virus (BISCHOFF, et al. An adenovirus mutant that replicates selectively in p53-deficient human tumor cells. *Science.* 1996, vol. 274, no. 5286, p. 373-6; He HEISE, et al. An adenovirus E1A mutant that demonstrates potent and selective systemic anti-tumoral efficacy. *Nature Medicine.* 2000, vol. 6, no. 10, p. 1134-9; WO 94/18992), are particularly preferred. Accordingly, this virus can be used to selectively infect and kill p53-deficient neoplastic cells. A person of ordinary skill in the art can also mutate and disrupt the p53 inhibitor gene in adenovirus 5 or other viruses according to established techniques. Adenoviral vectors deleted in the E1A Rb binding region can also be used in the present invention. For example, Delta24 virus which is a mutant adenovirus carrying a 24 base pair deletion in the E1A region (FUEYO, et al. A mutant oncolytic adenovirus targeting the Rb pathway produces anti-glioma effect in vivo. *Oncogene.* 2000, vol. 19, no. 1, p. 2-12). Delta24 has a deletion in the Rb binding region and does not bind to Rb. Therefore, replication of the mutant virus is inhibited by Rb in a normal cell. However, if Rb is inactivated and the cell becomes neoplastic, Delta24 is no longer inhibited. Instead, the mutant virus replicates efficiently and lyses the Rb-deficient cell.

An adenoviral vector according to the present invention can be generated in vitro in *Escherichia coli* (*E. coli*) by ligation or homologous recombination (see, for example, international application WO 96/17070) or else by recombination in a complementing cell line.

According to a preferred embodiment of the invention, the vector further comprises the elements necessary for the expression of the antibody according to the invention.

The elements necessary for the expression consist of all the elements which enable the nucleic acid sequence to be transcribed into RNA and the mRNA to be translated into polypeptide. These elements comprise, in particular, a promoter which may be regulable or constitutive. Naturally, the promoter is suited to the chosen vector and the host cell. Examples which may be mentioned are the eukaryotic promoters of the PGK (phosphoglycerate kinase), MT (metallothionein; MCIVOR. Human purine nucleoside phosphorylase and adenosine deaminase: gene transfer into cultured cells and murine hematopoietic stem cells by using recombinant amphotropic retroviruses. *Molecular and cellular biology.* 1987, vol. 7, no. 2, p. 838-46), α-1 antitrypsin, CFTR, surfactant, immunoglobulin, actin TABIN, et al. Adaptation of a retrovirus as a eukaryotic vector transmitting the herpes simplex virus thymidine kinase gene. *Molecular and cellular biology.* 1982, vol. 2, no. 4, p. 426-36) and SRα (TAKEBE, et al. SR alpha promoter: an efficient and versatile mammalian cDNA expression system composed of the simian virus 40 early promoter and the R-U5 segment of human T-cell leukemia virus type 1 long terminal repeat. *Molecular and cellular biology.* 1988, vol. 8, no. 1, p. 466-72) genes, the early promoter of the SV40 virus (Simian virus), the LTR of RSV (Rous sarcoma virus), the HSV-I TK promoter, the early promoter of the CMV virus (Cytomegalovirus), the p7.5K pH5R, pK1 L, p28 and p11 promoters of the vaccinia virus, chimeric promoters such as p11K7.5 and the E1A and MLP adenoviral promoters. The promoter can also be a promoter which stimulates expression in a tumor or cancer cell. Particular mention may be made of the promoters of the MUC-I gene, which is overexpressed in breast and prostate cancers (CHEN, et al. Breast cancer selective gene expression and therapy mediated by recombinant adenoviruses containing the DF3/MUC1 promoter. *The Journal of clinical investigation.* 1995, vol. 96, no. 6, p. 2775-82), of the CEA (standing for carcinoma embryonic antigen) gene, which is overexpressed in colon cancers (SCHREWE, et al. Cloning of the complete gene for carcinoembryonic antigen: analysis of its promoter indicates a region conveying cell type-specific expression. *Molecular and cellular biology.* 1990, vol. 10, no. 6, p. 2738-48) of the tyrosinase gene, which is overexpressed in melanomas (VILE, et al. Use of tissue-specific expression of the herpes simplex virus thymidine kinase gene to inhibit growth of established murine melanomas following direct intratumoral injection of DNA. *Cancer res.* 1993, vol. 53, no. 17, p. 3860-4), of the ERBB-2 gene, which is overexpressed in breast and pancreatic cancers (HARRIS, et al. Gene therapy for cancer using tumor-specific prodrug activation. *Gene therapy.* 1994, vol. 1, no. 3, p. 170-5) and of the α-fetoprotein gene, which is overexpressed in liver cancers (KANAI, et al. In vivo gene therapy for alpha-fetoprotein-producing hepatocellular carcinoma by adenovirus-mediated transfer of cytosine deaminase gene. *Cancer res.* 1997, vol. 57, no. 3, p. 461-5). The cytomegalovirus (CMV) early promoter is very particularly preferred.

However, when a vector deriving from a Vaccinia Virus (as for example an MVA vector) is used, the promoter of the thymidine kinase 7.5K gene and the pH5R promoter are particularly preferred.

The necessary elements can furthermore include additional elements which improve the expression of the nucleic acid sequence according to the invention or its maintenance in the host cell. Intron sequences, secretion signal sequences, nuclear localization sequences, internal sites for the reinitiation of translation of IRES type, transcription termination poly A sequences, tripartite leaders and origins of replication may in particular be mentioned. These elements are known to the skilled person. Among secretion signal sequence, sequences encoding the polypeptides as set forth in SEQ ID NO 5 and/or 8 are particularly preferred.

The recombinant vector according to the invention can also comprise one or more additional genes of interest, with it being possible for these genes to be placed under the control of the same regulatory elements (polycistronic cassette) or of independent elements. Genes which may in particular be mentioned are the genes encoding interleukins IL-2, IL-4, IL-7, IL-10, IL-12, IL-15, IL-18, chemokines as CCL19, CCL20, CCL21, CXCL-14, interferons, tumor necrosis factor (TNF), and factors acting on innate immunity and angiogenesis (for example PAI-1, standing for plasminogen activator inhibitor). In one particular embodiment, the recombinant vector according to the invention comprises the gene of interest encoding IL-2.

The present invention also relates to a cell comprising the nucleic acid sequence according to the invention. In a preferred embodiment, he cell according to the invention is eukaryotic cell and more preferably a mammalian cell. Mammalian cells available as hosts for expression are well known in the art and include many immortalized cell lines, such as but not limited to, Chinese Hamster Ovary (CHO)

cells, Baby Hamster Kidney (BHK) cells and many others. Suitable additional eukaryotic cells include yeast and other fungi.

The present invention also relates to a process for producing an antibody according to the invention comprising culturing the cell according to the invention under conditions permitting expression of the antibody and purifying the antibody from the cell or medium surrounding the cell.

In another embodiment, the present invention relates to a pharmaceutical composition comprising any one of the antibody, the nucleic acid sequence or the vector according to the invention and a pharmaceutically acceptable carrier. In a preferred embodiment, the pharmaceutical composition further comprises a compound of interest.

The pharmaceutically acceptable carrier is preferably isotonic, hypotonic or weakly hypertonic and has a relatively low ionic strength, such as for example a sucrose solution. Moreover, such a carrier may contain any solvent, or aqueous or partially aqueous liquid such as nonpyrogenic sterile water. The pH of the pharmaceutical composition is, in addition, adjusted and buffered so as to meet the requirements of use in vivo. The pharmaceutical composition may also include a pharmaceutically acceptable diluent, adjuvant or excipient, as well as solubilizing, stabilizing and preserving agents. For injectable administration, a formulation in aqueous, nonaqueous or isotonic solution is preferred. It may be provided in a single dose or in a multidose in liquid or dry (powder, lyophilisate and the like) form which can be reconstituted at the time of use with an appropriate diluent.

The present invention also relates, to a kit of part comprising (i) a pharmaceutical composition, an antibody, a nucleic acid sequence or a vector according to the invention and, (ii) a compound of interest.

As used herein the term, "compound of interest" relates to a therapeutic compound and preferably to a cancer therapeutic agent or a compound useful in the treatment of bone mass decrease.

According to a preferred embodiment, the cancer therapeutic agent is chosen from the group comprising Abraxane (Paclitaxel Albumin-stabilized Nanoparticle Formulation), Adriamycin (Doxorubicin Hydrochloride), Adrucil (Fluorouracil), Aldara (Imiquimod), Alemtuzumab, Alimta (Pemetrexed Disodium), Aminolevulinic Acid, Anastrozole, Aprepitant, Arimidex (Anastrozole), Aromasin (Exemestane), Arranon (Nelarabine), Arsenic Trioxide, Avastin (Bevacizumab), Azacitidine, Bevacizumab, Bexarotene, Bortezomib, Campath (Alemtuzumab), Camptosar (Irinotecan Hydrochloride), Capecitabine, Carboplatin, Cetuximab, Cisplatin, Clafen (Cyclophosphamide), Clofarabine, Clofarex (Clofarabine), Clolar (Clofarabine), Cyclophosphamide, Cytarabine, Cytosar-U (Cytarabine), Cytoxan (Cyclophosphamide), Dacogen (Decitabine), Dasatinib, Decitabine, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), Efudex (Fluorouracil), Ellence (Epirubicin Hydrochloride), Eloxatin (Oxaliplatin), Emend (Aprepitant), Epirubicin Hydrochloride, Erbitux (Cetuximab), Erlotinib Hydrochloride, Evacet (Doxorubicin Hydrochloride Liposome), Evista (Raloxifene Hydrochloride), Exemestane, Faslodex (Fulvestrant), Femara (Letrozole), Fluoroplex (Fluorouracil), Fluorouracil, Fulvestrant, Gefitinib, Gemcitabine Hydrochloride, Gemtuzumab Ozogamicin, Gemzar (Gemcitabine Hydrochloride), Gleevec (Imatinib Mesylate), Herceptin (Trastuzumab), Hycamtin (Topotecan Hydrochloride), Imatinib Mesylate, Imiquimod, Iressa (Gefitinib), Irinotecan Hydrochloride, Ixabepilone, Ixempra (Ixabepilone), Keoxifene (Raloxifene Hydrochloride), Kepivance (Palifermin), Lapatinib Ditosylate, Lenalidomide, Letrozole, Levulan (Aminolevulinic Acid), LipoDox (Doxorubicin Hydrochloride Liposome), Liposomal Cytarabine, Methazolastone (Temozolomide), Methotrexate, Mylosar (Azacitidine), Mylotarg (Gemtuzumab Ozogamicin), Nanoparticle Paclitaxel (Paclitaxel Albumin-stabilized Nanoparticle Formulation), Nelarabine, Neosar (Cyclophosphamide), Nexavar (Sorafenib Tosylate), Nilotinib, Nolvadex (Tamoxifen Citrate), Oncaspar (Pegaspargase), Oxaliplatin, Paclitaxel, Paclitaxel Albumin-stabilized Nanoparticle Formulation, Palifermin, Panitumumab, Paraplat (Carboplatin), Paraplatin (Carboplatin), Pegaspargase, Pemetrexed Disodium, Platinol-AQ (Cisplatin), Platinol (Cisplatin), Raloxifene Hydrochloride, Revlimid (Lenalidomide), Rituxan (Rituximab), Rituximab, Sclerosol Intrapleural Aerosol (Talc), Sorafenib Tosylate, Sprycel (Dasatinib), Sterile Talc Powder (Talc), Steritalc (Talc), Sunitinib Malate, Sutent (Sunitinib Malate), Synovir (Thalidomide), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalomid (Thalidomide), Thalidomide, Totect (Dexrazoxane Hydrochloride), Topotecan Hydrochloride, Torisel (Temsirolimus), Trastuzumab, Trisenox (Arsenic Trioxide), Tykerb (Lapatinib Ditosylate), Vectibix (Panitumumab), Velcade (Bortezomib), Vidaza (Azacitidine), Vorinostat, Xeloda (Capecitabine), Zinecard (Dexrazoxane Hydrochloride), Zoledronic Acid, Zolinza (Vorinostat) and Zometa (Zoledronic Acid).

According to a preferred embodiment of the invention the compound useful in the treatment of bone mass decrease is a biphosphonate, a selective oestrogen receptor modulators (SERMs), a parathyroid hormone (PTH) (e.g. teriparatide (Forteo)), strontium ranelate, Denosumab or calcitonin, or a combination thereof. According to a more preferred embodiment, the biphosphonate is chosen from the group comprising Alendronate (Fosamax, Fosamax Plus D), Etidronate (Didronel), Ibandronate (Boniva), Pamidronate (Aredia), Risedronate (Actonel, Actonel W/Calcium), Tiludronate (Skelid), and Zoledronic acid (Reclast, Zometa). According to a more preferred embodiment, the SERMs is chosen from the group comprising raloxifene (Evista), bazedoxifene/premarin (Aprelal) and tamoxifen.

According to another embodiment, the present invention relates to the use of the antibody, the nucleic acid sequence, the vector, the pharmaceutical composition or the kit of parts according to the invention for the treatment of diseases associated to an increased osteoclast activity. Such disease comprised but are not limited to endocrinopathies (hypercortisolism, hypogonadism, primary or secondary hyperparathyroidism, hyperthyroidism), hypercalcemia, deficiency states (rickets/osteomalacia, scurvy, malnutrition), chronic diseases (malabsorption syndromes, chronic renal failure (renal osteodystrophy), chronic liver disease (hepatic osteodystrophy), drugs (glucocorticoids (glucocorticoid-induced osteoporosis), androgen deprivation therapy, aromatase inhibitor therapy, heparin, alcohol), and hereditary diseases (osteogenesis imperfecta, homocystinuria), osteoporosis, osteopetrosis, inflammation of bone associated with arthritis and rheumatoid arthritis, periodontal disease, fibrous dysplasia, and/or Paget's disease.

According to another embodiment, the present invention relates to the use of the antibody, the nucleic acid sequence, the vector, the pharmaceutical composition or the kit of parts according to the invention for the treatment of diseases associated to inflammation and/or autoimmunity. Such diseases comprise but are not limited to seronegative spondyloarthropathy (psoriatic arthritis, ankylosing spondylitis, reiters syndrome, spondyloarthropathy associated with inflammatory bowel disease), prosthetic joint loosening, connective tissue diseases (juvenile rheumatoid arthritis, rheumatoid arthritis, systemic lupus erythematosus (SLE) and lupus nephritis, scleroderma, Sjogren's syndrome, mixed connective tissue disease, polymyositis, dermatomyositis), inflammatory bowel disease (e.g. Crohn's disease; ulcerative colitis), whipples disease, arthritis associated with granulomatous ileocolitis, inflammatory skin conditions (autoimmune bullous pemphigoid, autoimmune pemphigus vulgaris, eczema, dermatitis), inflammatory lung disease (alveolitis, pulmonary fibrosis, sarcoidoisis, asthma, bronchitis, bronchiolitis obliterans), inflammatory renal disease (glomerulonethritis, renal allograft rejection, renal tubular inflammation), atherosclerosis, systemic vasculitis (temporal arteritis/giant cell arteritis, takayasu arteritis, polyarteritis nodosa, Kawasaki disease, Wegener's granulomatosis, churg strauss syndrome, microscopic polyangiitis, necrotising glomerulonephritis, henoch schonlein purpura, essential cryoglobulinaemic vasculitis and other small vessel vasculitis, Behcets disease), macrophage activation diseases (macrophage activation syndrome (MAS), adult onset stills disease, haemophagocytic syndrome), polymyalgia rheumatica, primary biliary sclerosis, sclerosing cholangitis, autoimmune hepatitis, Type 1 Diabetes Mellitus, Hashimoto's thyroiditis, Graves' disease, multiple sclerosis (MS), Guillain-Barre syndrome, Addison's disease, and/or Raynaud's phenomenon, Goodpasture's syndrome.

According to another embodiment, the present invention relates to the use of the antibody, the nucleic acid sequence, the vector, the pharmaceutical composition or the kit of parts according to the invention for the treatment of cancer.

As used herein, the term "cancer" refers but is not limited to adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, tubular cell carcinoma, amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periosteal sarcoma, reticulum cell sarcoma (histiocytic lymphoma), round cell sarcoma, spindle cell sarcoma, synovial sarcoma, telangiectatic audiogenic sarcoma, Burkitt's lymphoma, NPDL, NML, NH and diffuse lymphomas. According to a preferred embodiment, the method according to the invention is directed to the treatment of metastatic cancer to bone, wherein the metastatic cancer is breast, lung, renal, multiple myeloma, thyroid, prostate, adenocarcinoma, blood cell malignancies, including leukemia and lymphoma; head and neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, and cervical cancer; bladder cancer; brain cancer, including neuroblastoma; sarcoma, osteosarcoma; and skin cancer, including malignant melanoma or squamous cell cancer.

The present invention further concerns a method for improving the treatment of a cancer patient which is undergoing chemotherapeutic treatment with a cancer therapeutic agent, which comprises co-treatment of said patient along with a method as above disclosed.

The present invention further concerns a method of improving cytotoxic effectiveness of cytotoxic drugs or radiotherapy which comprises co-treating a patient in need of such treatment along with a method as above disclosed.

The present invention further concerns a method for improving the treatment of a patient with a disease associated to an increased osteoclast activity which is undergoing treatment with a biphosphonate, a selective oestrogen receptor modulators (SERMs), a parathyroid hormone (PTH) (e.g. teriparatide (Forteo)), strontium ranelate, Denosumab or calcitonin, or a combination thereof, which comprises co-treatment of said patient along with a method as above disclosed.

In another embodiment use of an antibody of the invention is contemplated in the manufacture of a medicament for preventing or treating metastatic cancer to bone in a patient suffering from metastatic cancer. In a related embodiment, the metastatic cancer is breast, lung, renal, multiple myeloma, thyroid, prostate, adenocarcinoma, blood cell malignancies, including leukemia or lymphoma; head or neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, or cervical cancer; bladder cancer; brain cancer, including neuroblastoma; sarcoma, osteosarcoma; or skin cancer, including malignant melanoma or squamous cell cancer.

According to another embodiment, the present invention relates to the use of the antibody, the nucleic acid sequence, the vector, the pharmaceutical composition or the kit of parts according to the invention in the manufacture of a medicament.

According to another embodiment, the present invention relates to the use of the antibody, the nucleic acid sequence, the vector, the pharmaceutical composition or the kit of parts according to the invention in the manufacture of a medicament for treating a patient having cancer.

According to another embodiment, the present invention relates to the use of the antibody, the nucleic acid sequence, the vector, the pharmaceutical composition or the kit of parts according to the invention in the manufacture of a medicament for treating a patient having a disease associated to an increased osteoclast activity.

According to another embodiment, the present invention relates to the use of the antibody, the nucleic acid sequence, the vector, the pharmaceutical composition or the kit of parts according to the invention in the manufacture of a medicament for treating a patient having an inflammatory disease, more specifically an inflammatory bowel disease.

According to another embodiment, the present invention relates to the use of the antibody, the nucleic acid sequence, the vector, the pharmaceutical composition or the kit of parts according to the invention in the manufacture of a medicament for treating a patient suffering from rheumatoid arthritis.

Administering the antibody, the nucleic acid sequence, the vector, the pharmaceutical composition or the kit of parts according to the invention may be accomplished by any means known to the skilled artisan. Preferred routes of administration include but are not limited to intradermal, subcutaneous, oral, parenteral, intramuscular, intranasal, sublingual, intratracheal, inhalation, ocular, vaginal, and rectal. According to a preferred embodiment the antibody, the nucleic acid sequence, the vector, the pharmaceutical composition or the kit of parts according to the invention are delivered systemically.

The administration may take place in a single dose or a dose repeated one or several times after a certain time interval. Desirably, the antibody, the nucleic acid sequence, the vector, the pharmaceutical composition or the kit of parts according to the invention are administered 1 to 10 times at weekly intervals.

For general guidance, suitable dosage for the antibody is about 2 mg/kg to 30 mg/kg, 0.1 mg/kg to 30 mg/kg or 0.1 mg/kg to 10 mg/kg body weight. Suitable dosage for the vector according to the invention varies from about $10^4$ to $10^{10}$ pfu (plaque forming units), desirably from about $10^5$ and $10^8$ pfu for MVA vector whereas it varies from about $10^5$ to $10^{13}$ iu (infectious units), desirably from about $10^7$ and $10^{12}$ iu for adenovirus based vector. A composition based on vector plasmids may be administered in doses of between 10 μg and 20 mg, advantageously between 100 μg and 2 mg.

When the use or the method according to the invention is for the treatment of cancer, the method or use of the invention can be carried out in conjunction with one or more conventional therapeutic modalities (e.g. radiation, chemotherapy and/or surgery). The use of multiple therapeutic approaches provides the patient with a broader based intervention. In one embodiment, the method of the invention can be preceded or followed by a surgical intervention. In another embodiment, it can be preceded or followed by radiotherapy (e.g. gamma radiation). Those skilled in the art can readily formulate appropriate radiation therapy protocols and parameters which can be used (see for example PEREZ. Principles and practice of radiation oncology. 2nd edition. LIPPINCOTT, 1992).

BRIEF DESCRIPTION OF FIGURES IN THE DRAWINGS

FIG. 6 shows the nucleic acid sequence (SEQ ID NO: 1) and deduced amino acid sequence (SEQ ID NO: 2) of the CXIIG6 heavy chain. The primer sequences including restriction sites for cloning added to the nucleotide sequences are underlined. The restriction sites are shown in underlined italic type. The amino acid sequences of the V-domains are highlighted in bold type.

FIG. 7 shows the nucleic acid sequence (SEQ ID NO: 3) and deduced amino acid sequence (SEQ ID NO: 4) of the CXIIG6 light chain. The primer sequences including restriction sites for cloning added to the nucleotide sequences are underlined. The restriction sites are shown in underlined italic type. The amino acid sequences of the V-domains are highlighted in bold type.

Figure 8:
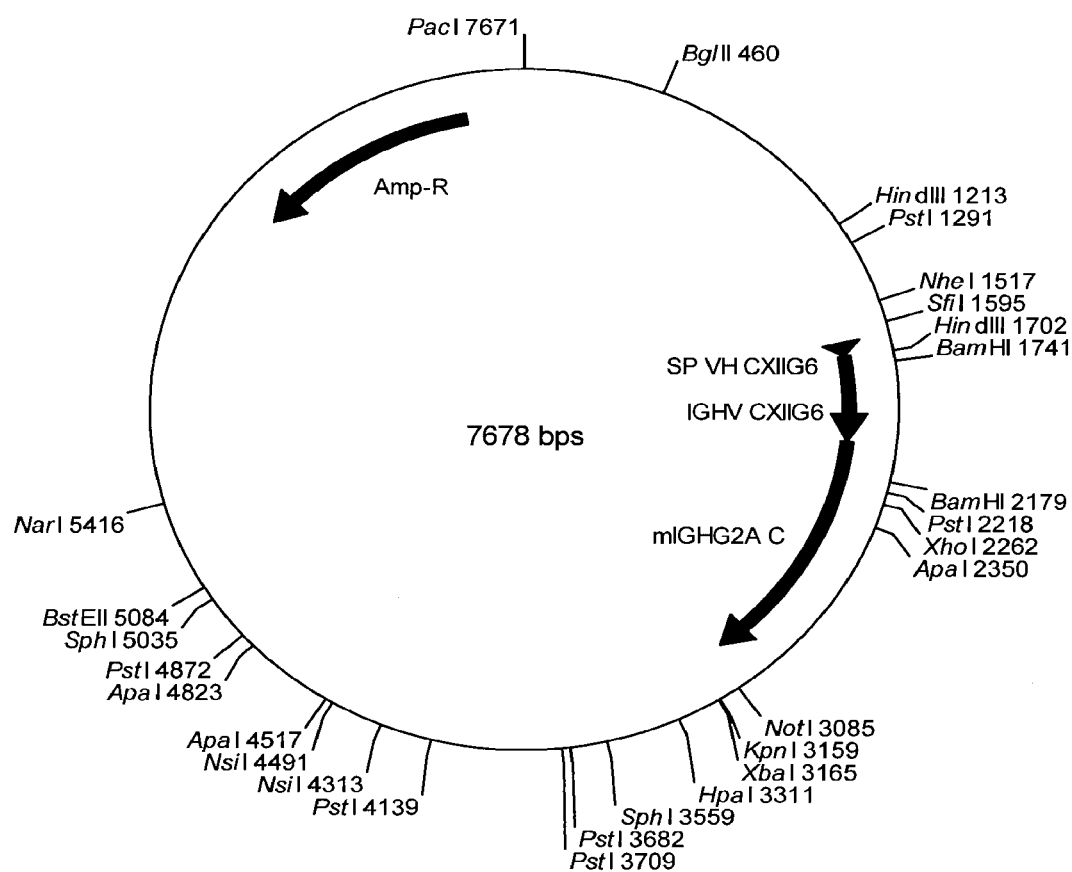

FIG. 8 shows the plasmid construct pTG17753.

Figure 9:
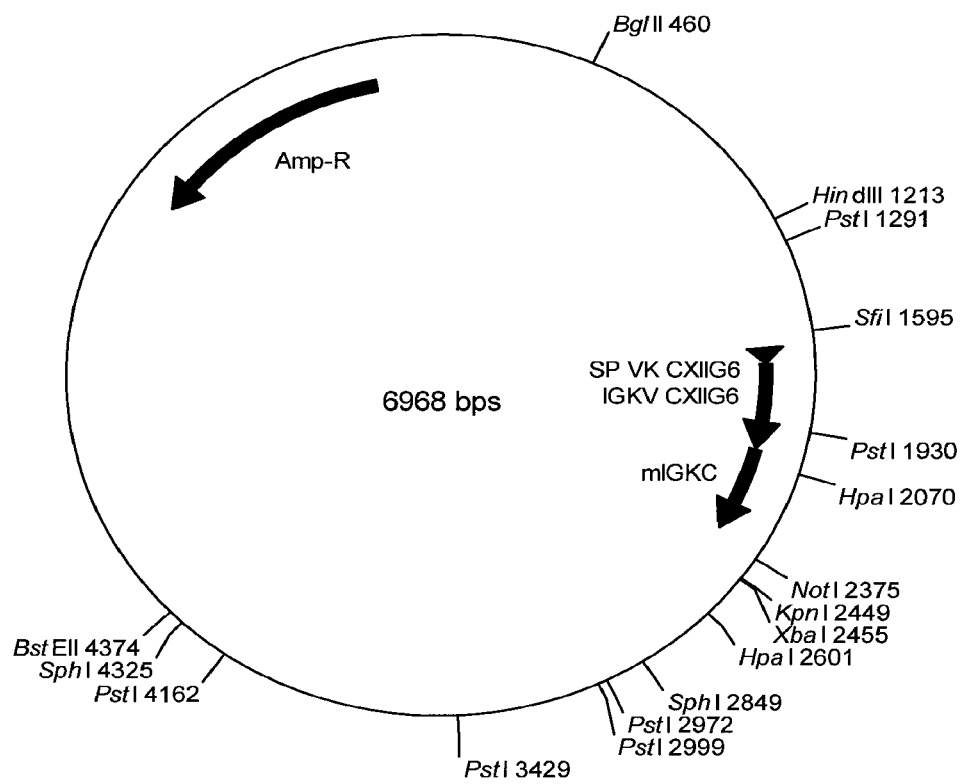

FIG. 9 shows the plasmid construct pTG17727.

Figure 10:
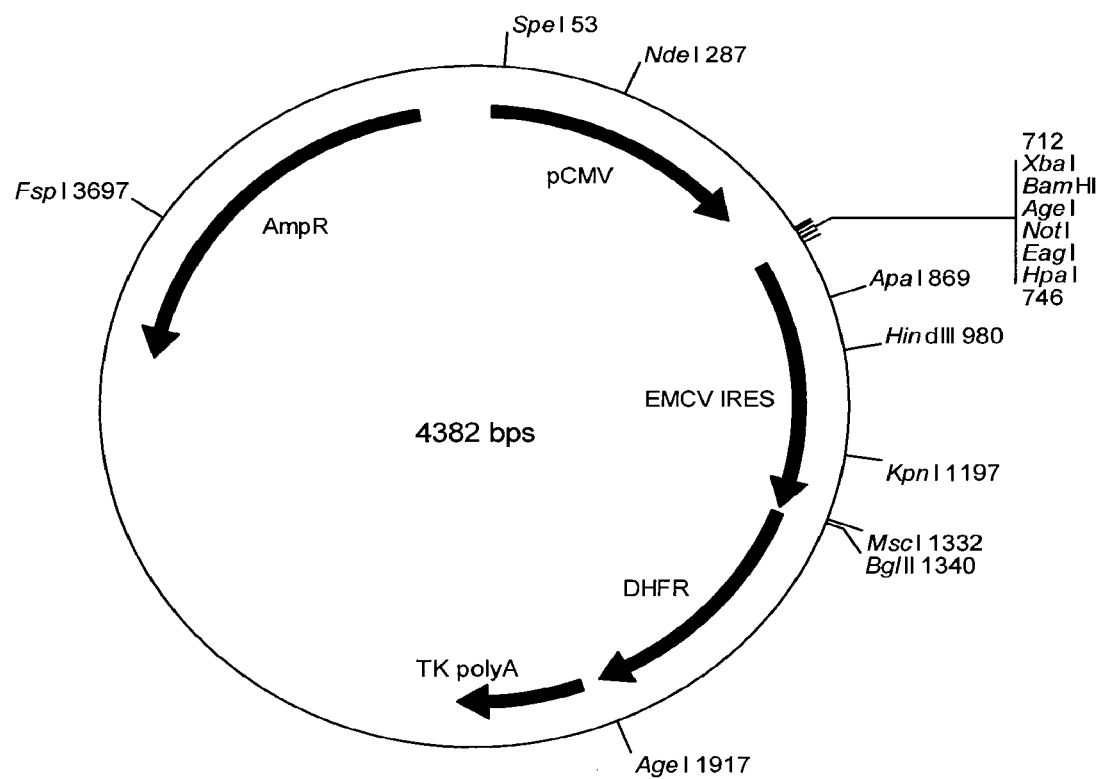

FIG. 10 shows the plasmid construct pOptiVEC™.

Figure 11:
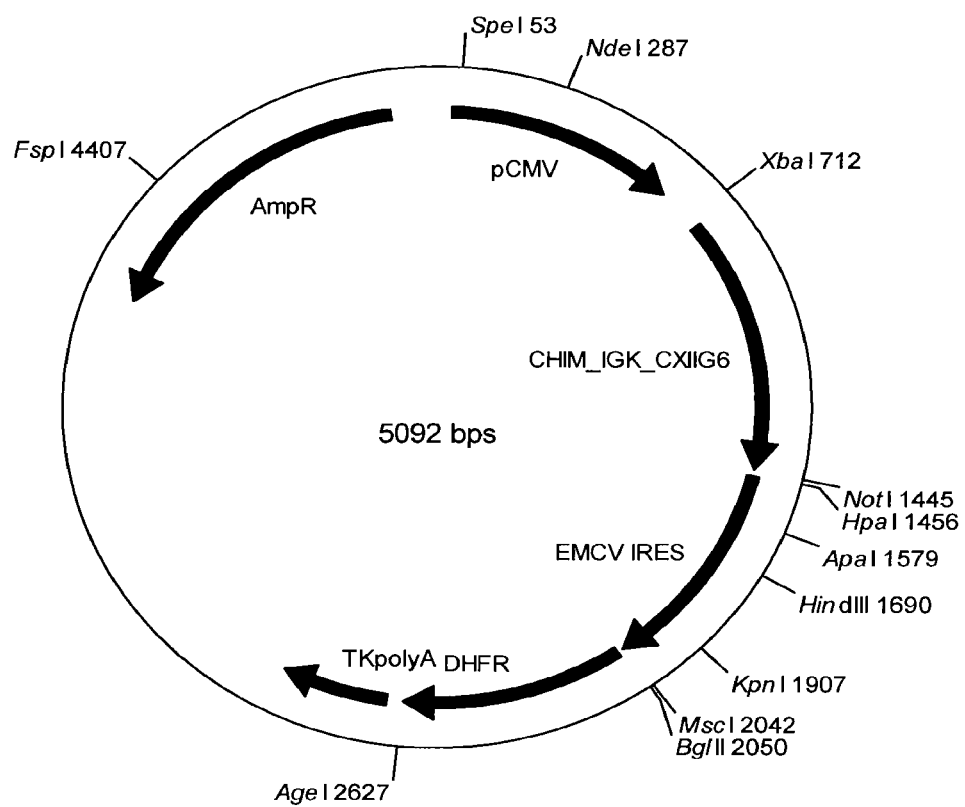

FIG. 11 shows the plasmid construct pTG17895.

Figure 12:
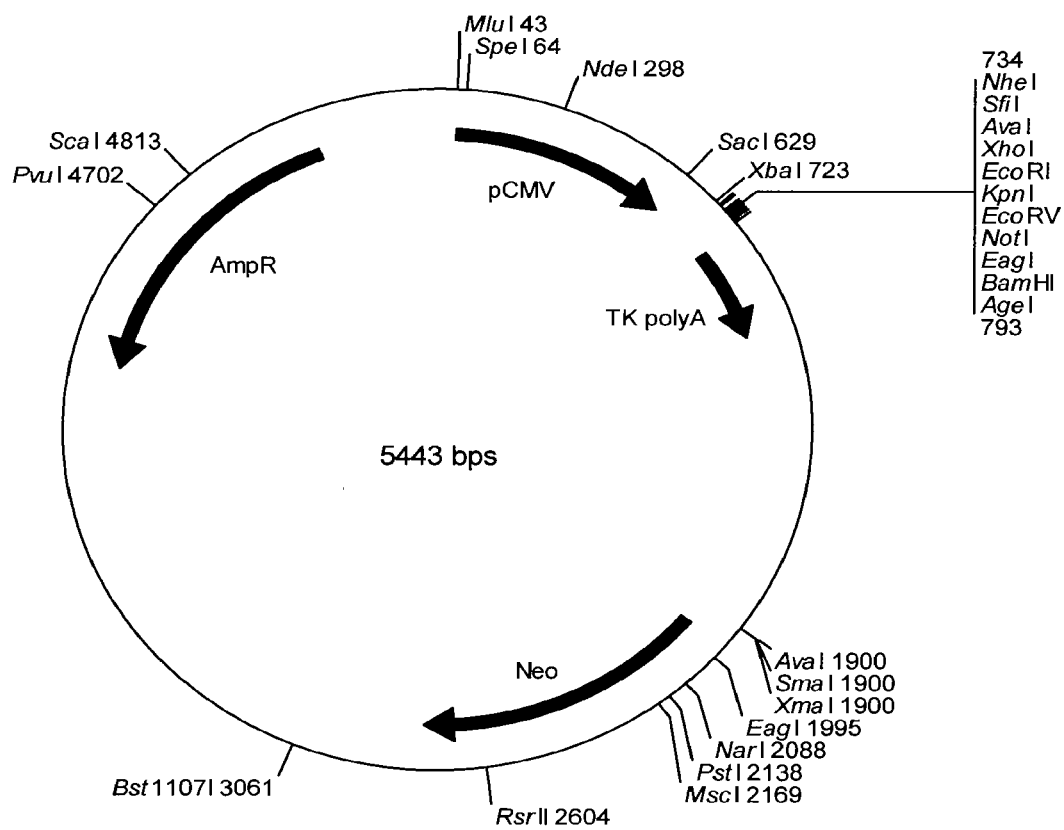

FIG. 12 shows the plasmid construct pTG17812.

Figure 13:
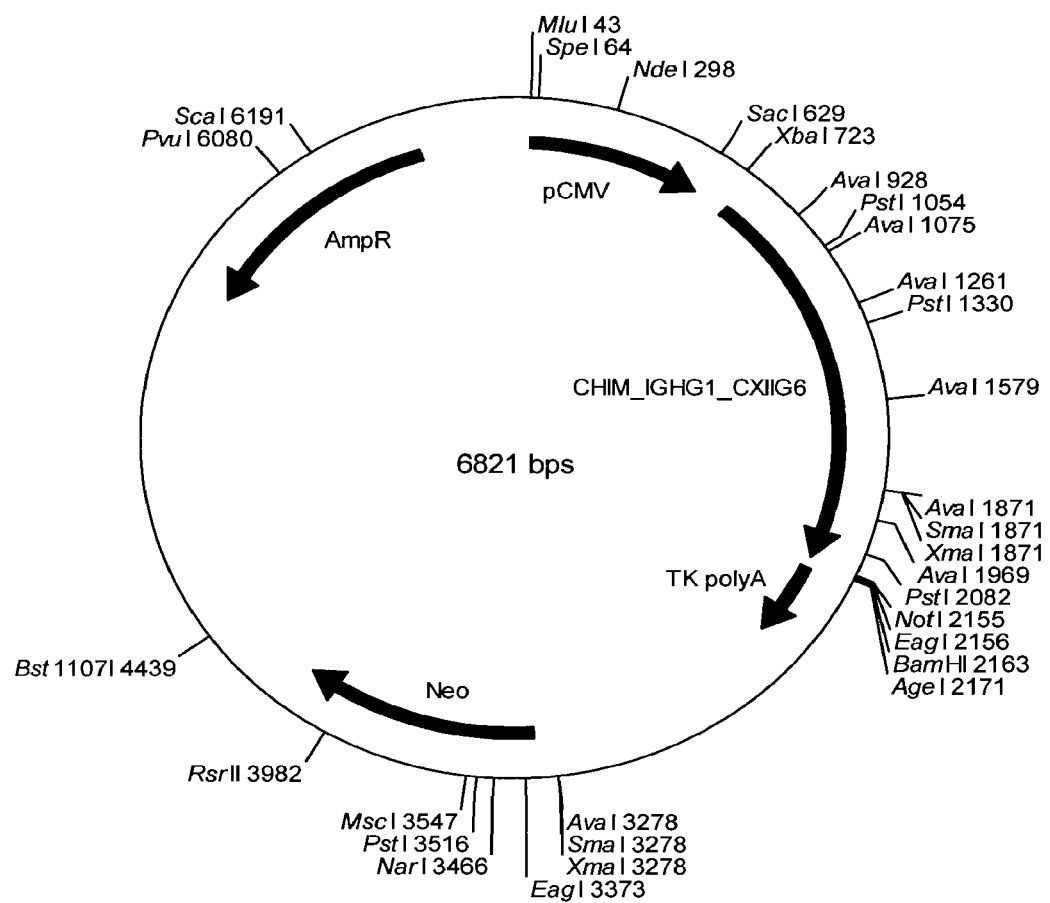

FIG. 13 shows the plasmid construct pTG17868.

Figure 14:
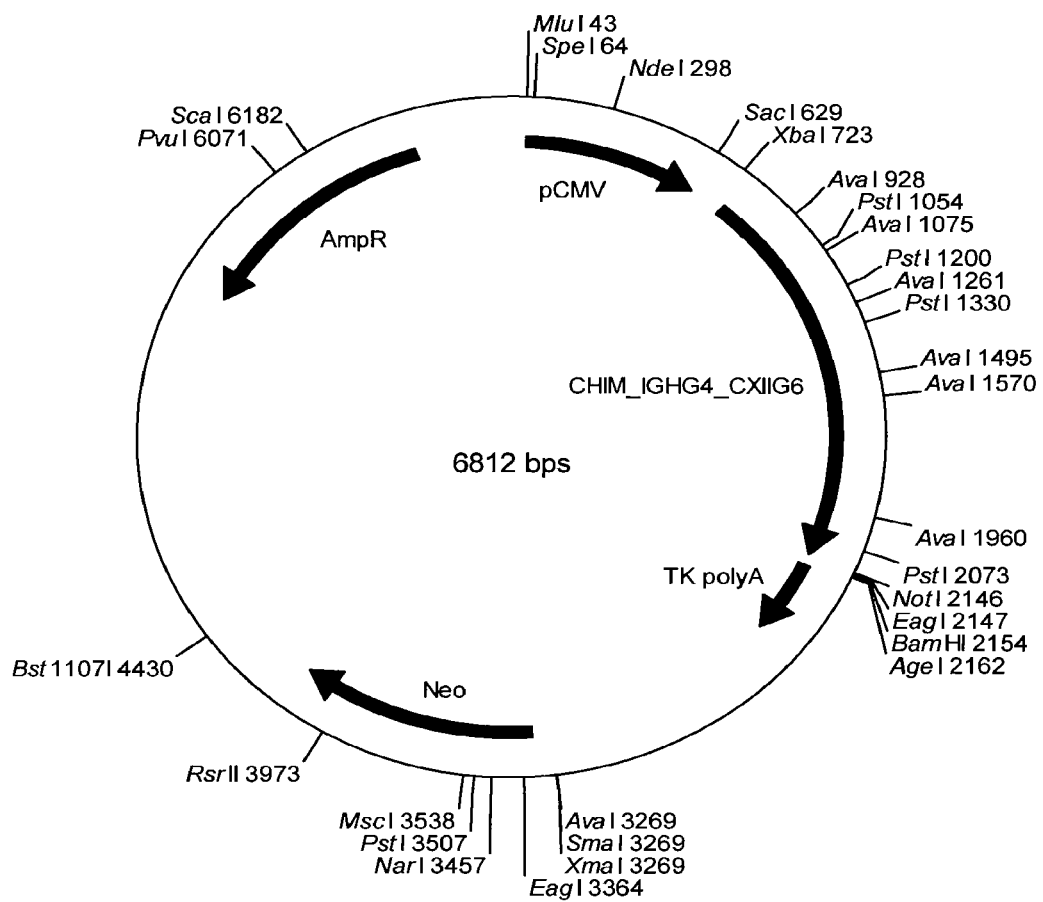

FIG. 14 shows the plasmid construct pTG17869.

FIG. 15 shows humanized CXIIG6 light chain variants.

FIG. 16 shows humanized CXIIG6 IgG1 heavy chain variants.

Figure 17:
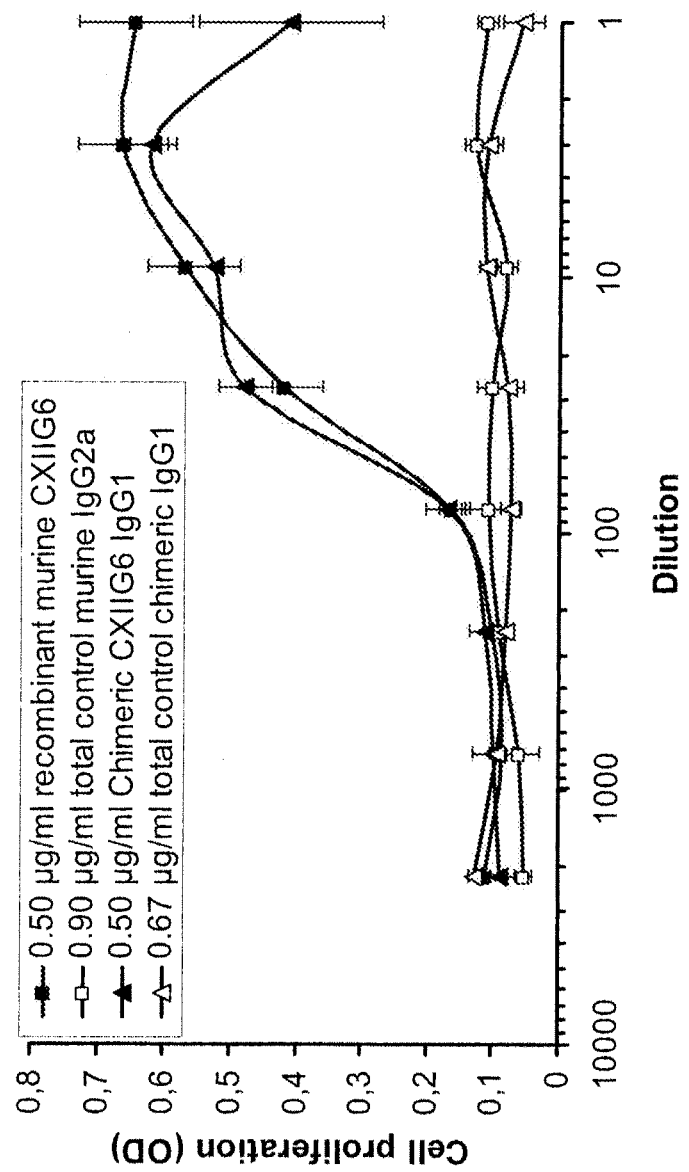

FIG. 17 shows the specific blockade of soluble human CSF-1R by recombinant murine CXIIG6 and chimeric CXIIG6 IgG1.

Figure 18:
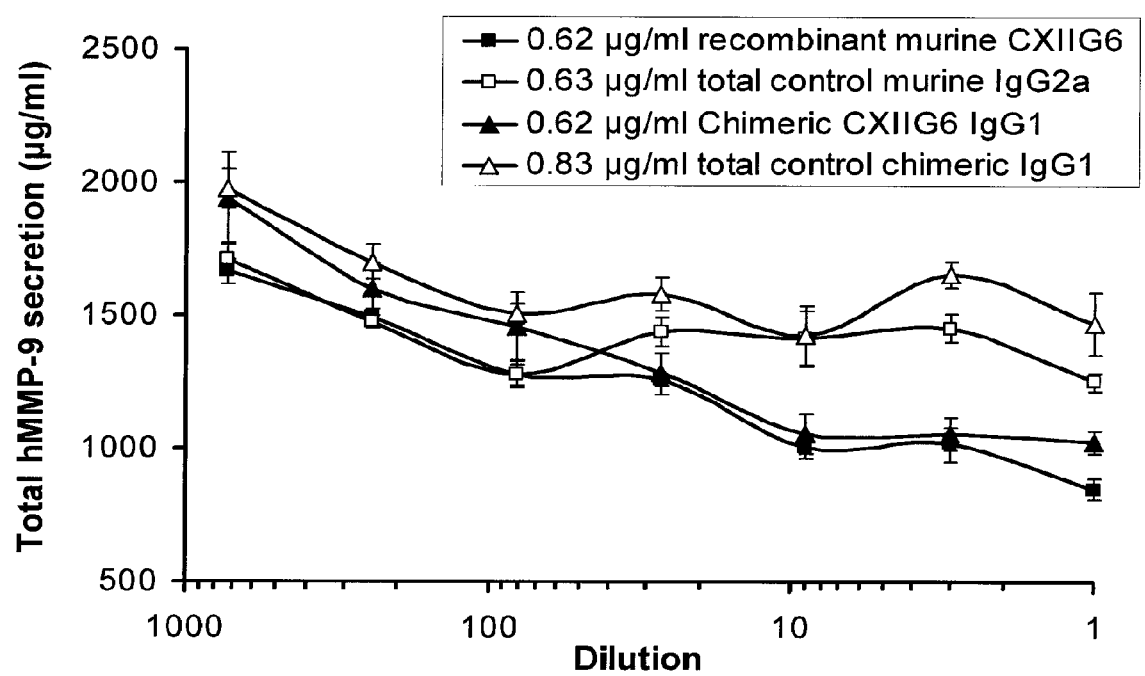

FIG. 18 shows the inhibition of human osteoclast differentiation and secretion of matrix-metalloprotease-9 (MMP-9) in presence of recombinant murine CXIIG6 and chimeric CXIIG6 IgG1

FIG. 19 shows the different constructs of CSF-1R used to map the epitope of the monoclonal antibodies of the Invention versus those of commercially available anti-CSF-1R antibodies. Human sequence is represented as an open bar and murine sequence as a filled bar. Antibodies with their names crossed indicate that they do not bind the construct.

FIG. 20 shows the limits of the Ig-like domains of the different constructs of CSF-1R used to map the epitope FIG. 21: Competition curve between $^{125}$I-H27K15 antibody and unlabeled H27K15 on EL4-CSF-1R FIG. 22: Competition curve between $^{125}$I-H27K15 antibody and various antibodies on EL4-CSF-1R FIG. 23: Post-incubation competition curves: CSF-1/mAb FIG. 24: Pre-incubation competition curves: mAb/CSF-1

FIG. 25: Co-incubation competition curves: mAB+CSF-1

FIG. 26: Co-incubation competition curves: mAB+CSF-1R

FIG. 27: Lack of cross-reactivity of mAB variants

FIG. 28: Blockade of soluble CSF-1R. The three hCXIIG6 variants and the chCXIIG6 block soluble human CD115 and restore the CSF-1-dependent growth of M-NFS-60 cells. Results are expressed as means+/−SEM of quadruplicate wells. ND50 values were calculated using GraphPadPrism five-parameter logistic equation.

FIGS. 29: A/B/C/D: Inhibition of CSF-1 dependent proliferation of AML3 cells. For FIG. 29A, AML5 cells were stained with either the anti-human CD115 mAN 3291 (left panel) or with chCXIIG6 (right panel). For each panel, the left histogram corresponds to AML5 cells stained with the isotope controls (respectively mouse $IgG_1$ and rituximab). FIG. 29B shows that AML5 cell growth is stimulated by CSF-1 in a dose-dependent fashion. FIG. 29C shows that hCXIIG6 variants and chCXIIG6 inhibit CSF-1-dependent proliferation of AML5 cells, showing results from three independent experiments. FIG. 29D includes the EC50 and R square values, as calculated by GraphPad Prism, from the results shown in FIG. 29C.

FIGS. 30 A/B: ADCC activity on EL4-CSF-R target cells. In 30A, PBMC from blood donor #1 were used as effector cells to measure the cytotoxic activity of H27K5, H27K15 and H19K12 on EL4-CD115 target cells at an E:T ratio of 25. In 30B, PBMC from donor #2 were tested in the same assay as FIG. 30A at the indicated E:T ratios. Asterisks (*) indicate p<0.05 compared with rituximab, while theta symbols (φ) indicate p<0.05 compared with chCXIIG6.

FIGS. 31A/B: Therapeutic effect in BeWo choriocarcinoma tumor model

FIGS. 32A through 32H: Listing of sequences SEQ ID NO: 37 to SEQ ID NO:47

EXAMPLES

Specific Staining of CSF-1R-Transfected NIH/3T3 Cells by mAb CXIIG6

Figure 1:
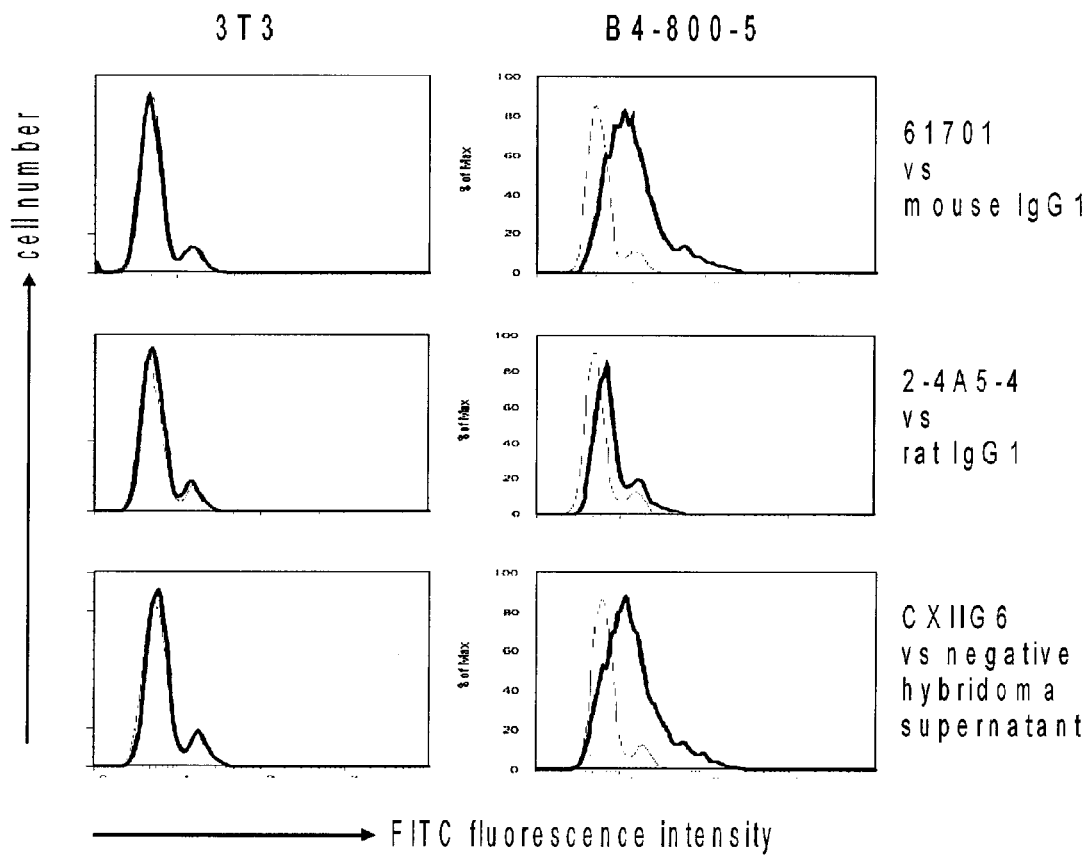
FIG. 1 depicts the specific staining of CSF-1R-transfected NIH/3T3 cells by mAb CXIIG6.

The B4-800-5 cell line was generated by stable transfection of NIH/3T3 cells with an expression plasmid encoding the full-length human CSF-1R. Cell-surface CSF-1R expression on B4-800-5 cells was verified by indirect immunostaining with the anti-human CSF-1R mAbs 61701 (mouse IgG$_1$, R&D Systems) or 2-4A5-4 (rat IgG$_{1,k}$, GeneTex), compared to isotype controls (FIG. 1, upper and middle panels). Culture supernatants from hybridoma CXIIG6 or from a negative control hybridoma were used for immunostaining B4-800-5 cells or parental NIH/3T3 cells (FIG. 1, lower panels).

Flow cytometry analysis showed that culture supernatant from hybridoma CXIIG6 selectively stained B4-800-5 cells, demonstrating the mAb specificity for cell-surface CSF-1R.

Partial Inhibition of CSF-1 Binding to Cell-Surface CSF-1R $3 \times 10^5$ THP-1 cells (human CSF-1R-positive monocytic leukemia cell line) were incubated for 30 min at 4° C. in the presence of either hybridoma culture supernatants, serum from a naive or an anti-CSF-1R-immunized mouse (dilution 1:1000), mAb anti-CSF-1R 2-4A5-4 (GeneTex) or a control rat IgG$_1$ (10 µg/ml), or no reagent. After two washes with cold PBS, cells were incubated with 1 µg/ml biotinylated recombinant human CSF-1 for 30 min. Cells were washed twice and further incubated for 30 min at 4° C. with 10 µg/ml streptavidin-Alexa Fluor 488 (Invitrogen). After washing with PBS and fixation with 4% paraformaldehyde, cell staining was analyzed by flow cytometry.

Figure 2:
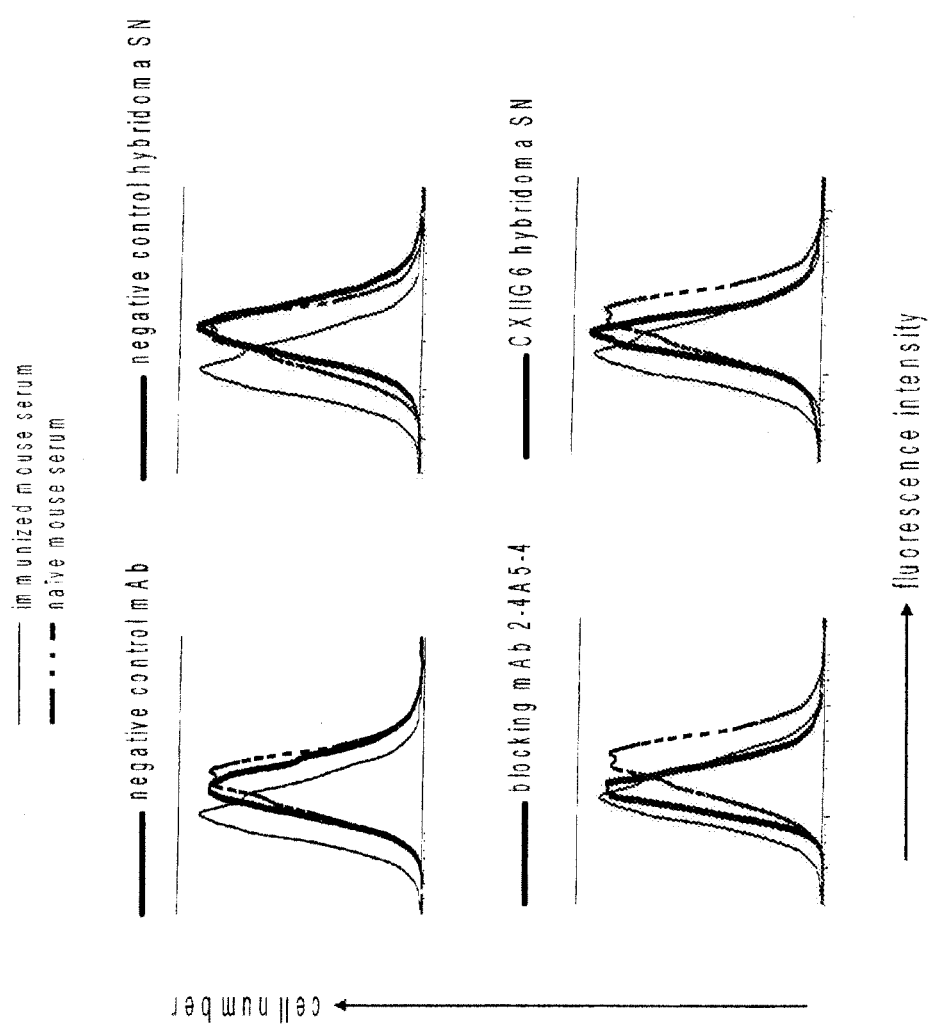
FIG. 2 shows the inhibition of CSF-1 binding to cell-surface CSF-1R in presence of mAb CXIIG6.

Decreased fluorescence intensities compared to control samples reflect the inhibition of CSF-1 binding to cell-surface CSF-1R. Serum from a CSF-1R-immunized mouse blocks CSF-1 binding to THP-1 cells (FIG. 2). While negative control hybridoma supernatant or an irrelevant mAb show no effect, culture supernatant from hybridoma CXIIG6 seems to inhibit, at least partially, CSF-1 binding to THP-1 cells (FIG. 2, lower right panel).

First Localization of mAb CXIIG6 Binding Site

To identify the binding site of mAb CXIIG6 on the CSF-1R, a Western blot was performed using soluble forms of the human CSF-1R comprising either the five extracellular immunoglobulin-like domains (Met 1 to Glu 512, R&D Systems) or only the three N-terminal immunoglobulin-like domains of the extracellular region of CSF-1R (Met 1 to Ser 290), both fused at their C-terminal ends to the Fc region of a human IgG$_1$. A soluble form of the EGFR fused to human IgG$_1$ Fc (R&D Systems) was used as a negative control.

Hundred nanograms of each soluble receptor were submitted to electrophoresis in native conditions before transfer to nitrocellulose sheet and probing with either hybridoma supernatants, rabbit pAb c-fms/CSF-1R H300 (Santa Cruz Biotechnology), mouse mAb 61701 (R&D Systems) or serum from naive or CSF-1R-immunized mice.

Both soluble forms of the CSF-1R were detected as broad bands when probed with pAb c-fms/CSF-1R H300, mAb 61701 or serum from the immunized mouse. No detectable signals were observed with naive mouse serum or a negative control hybridoma supernatant. CXIIG6 hybridoma supernatant recognized CSF-1R$_{1-290}$:Fc as well as CSF-1R$_{1-512}$:Fc, but not EGFR:Fc, indicating that CXIIG6 binds specifically to an epitope lying within the three N-terminal immunoglobulin-like domains (between residues 1 to 290) of the human CSF-1R.

Specific Blockade of Soluble Human CSF-1R by mAb CXIIG6

The CSF-1-dependent murine myeloid leukemia M-NFS-60 cell line (#CRL-1838, ATCC) was used to assess the blocking activity of CXIIG6 hybridoma supernatant on human and murine CSF-1R. Five nanograms of soluble human CSF-1R(CSF-1R$_{1-512}$: Fc from R&D Systems) were preincubated in white 96-well microplates with serial dilutions of either hybridoma supernatants, mAb 61701 (R&D Systems) or murine isotype control mAb. 10E4 M-NFS-60 cells cultured overnight in the absence of CSF-1 were then added into the culture wells together with 0.1 ng of human CSF-1 in a final assay volume of 100 µl. Cultures were incubated for 48 h at 37° C. and proliferation was quantified by BrdU incorporation using a Cell Proliferation ELISA (Roche).

Figure 3:
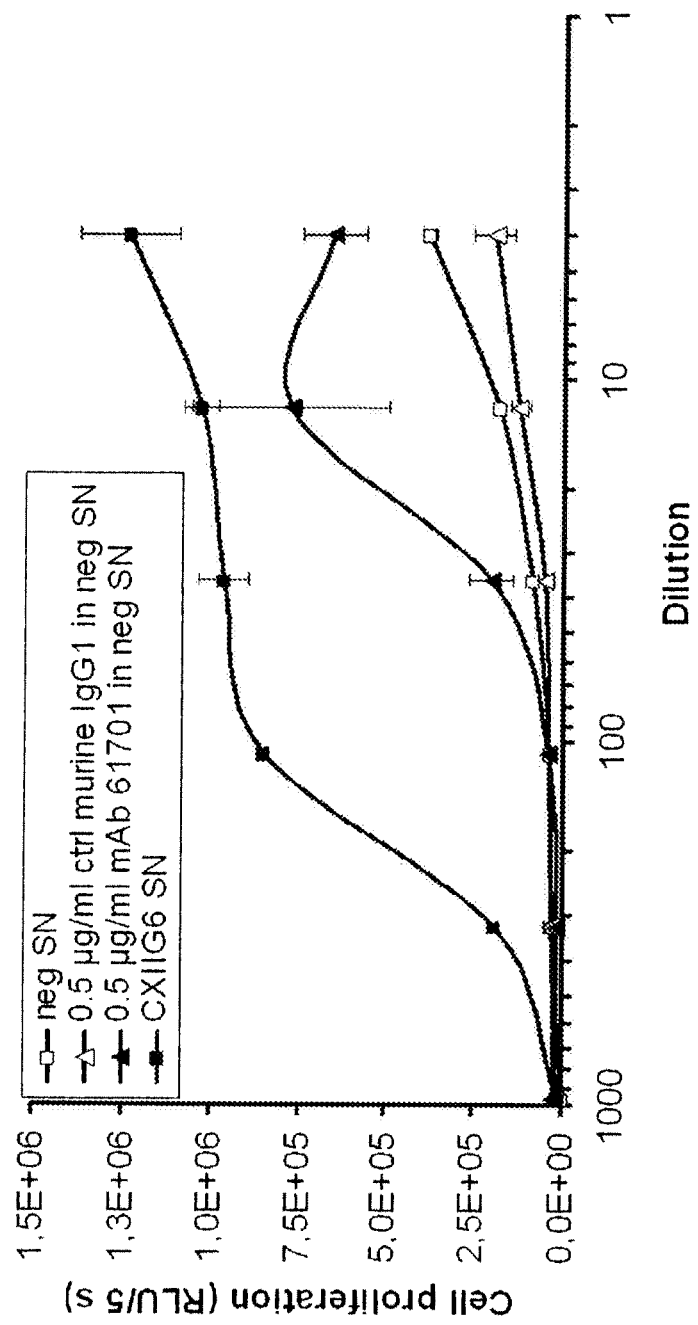
FIG. 3 shows the specific blockade of soluble human CSF-1R by mAb CXIIG6 ('ctrl' means control; 'neg SN' means negative control hybridoma supernatant).

Soluble human CSF-1R completely inhibited the proliferation of M-NFS-60 cells mediated by human CSF-1, as shown in the presence of negative hybridoma supernatant containing or not a negative control IgG$_1$ (FIG. 3; mean+/−SEM of 3 wells). In contrast, CXIIG6 hybridoma supernatant and positive control mAb 61701 were both able to restore cell proliferation in a dose-dependent manner, showing that they were able to neutralize soluble human CSF-1R.

In this assay, active M-NFS-60 cell proliferation in the presence of low dilutions of CXIIG6 hybridoma supernatant showed that mAb CXIIG6 was unable to block the murine CSF-1R expressed by M-NFS-60 cells. Moreover, in a murine CSF-1-supported M-NFS-60 proliferation assay performed in the absence of soluble CSF-1R, treatment with mAb AFS98 anti-mouse CSF-1R (eBioscience) resulted in a dramatic concentration-dependent decrease of cell growth (data not shown). CXIIG6 hybridoma supernatant, like negative control antibodies and negative hybridoma supernatant, caused no reduction in cell proliferation. These results demonstrate that mAb CXIIG6 specifically targets human CSF-1R.

Inhibition of Human Osteoclast Differentiation and Secretion of Matrix-Metalloprotease-9 (MMP-9)

Osteoclasts were generated from human monocytes obtained by elutriation of PBMCs from a healthy blood donor. In brief, monocytes were seeded at 2×10E4 cells per well in 96-well plates and treated for 45 min with either hybridoma culture supernatants, mAbs anti-human CSF-1R 61701 (R&D Systems) or 2-4A5-4 (GeneTex), mAb anti-human CSF-1 26730 (R&D Systems), murine or rat isotype controls, or sera from naive and CSF-1R-immunized mice diluted in hybridoma culture medium. Complete a-MEM medium was added to the culture wells with or without human CSF-1 and RANKL (PeproTech, 25 and 40 ng/ml respectively). Hybridoma supernatants, mAbs or/and medium with or without cytokines were replenished every 3 days for 9 days. Conditioned culture supernatants were harvested on day 9 and assayed for total human MMP-9 using an ELISA assay (R&D Systems). Osteoclast formation was evaluated by staining of tartrate-resistant acid phosphatase (TRAP) using the leukocyte acid phosphatase kit from Sigma-Aldrich.

Figure 4:
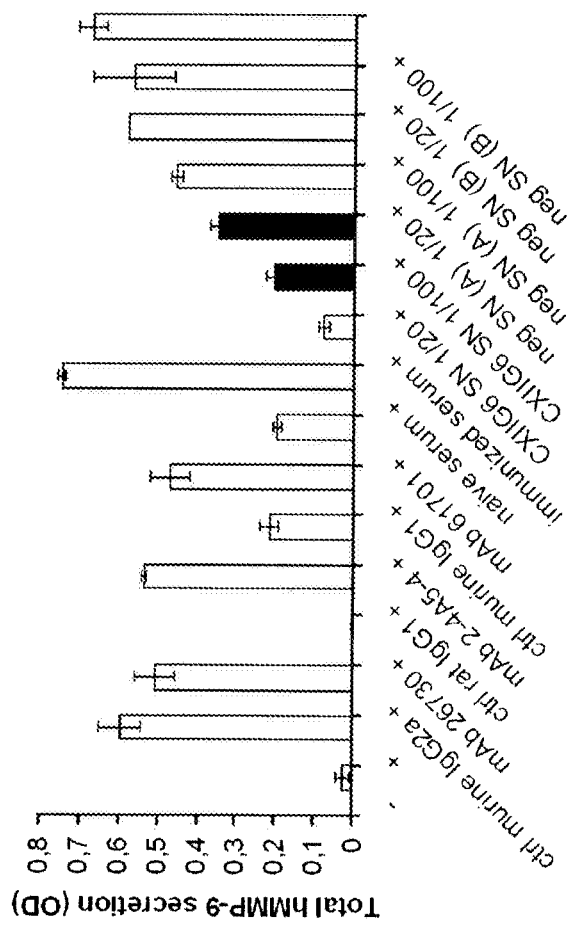
FIG. 4 shows the inhibition of human osteoclast differentiation and secretion of matrix-metalloprotease-9 (MMP-9) in presence of mAb CXIIG6 ('ctrl' means control; 'CXIIG6 SN' means CXIIG6 hybridoma supernatant; 'neg SN' means negative control hybridoma supernatant).

CSF-1+RANKL induced monocytes to differentiate into osteoclasts, defined as large multinucleated TRAP-positive cells, whereas no TRAP-positive osteoclasts were obtained in the absence of cytokines. Addition of 0.5 µg/ml anti-CSF-1 mAb 26730 completely abrogated osteoclast differentiation, as shown by lack of MMP-9 secretion. Anti-CSF-1R mAbs 61701 or 2-4A5-4 at the same concentration and immunized mouse serum (dilution 1:1000) inhibited osteoclast formation only partially (FIG. 4; with (+) or without (−) cytokines; mean+/−SEM of 3 wells; *: mean of 2 wells). Treatment with CXIIG6 hybridoma culture supernatant diluted 1:20 or 1:100 significantly reduced the level of MMP-9 production, compared with two negative control hybridoma supernatants (A, B). These results demonstrate that mAb CXIIG6 inhibits the differentiation of osteoclasts from human monocytes by blocking the function of cell surface CSF-1R.

Inhibition of the CSF-1-Dependent Phosphorylation of CSF-1R

The B4-800-5 cell line obtained by stable transfection of NIH/3T3 cells with a plasmid expressing human CSF-1R was used to investigate the effect of CXIIG6 hybridoma supernatant on CSF-1-dependent CSF-1R phosphorylation. Cells were seeded at 2×10E5 cells per 60-mm Petri dish and cultured for 48 to 72 h. Following serum deprivation for 1 h at 37° C., cells were treated for 1 h at 37° C. with culture medium containing either CXIIG6 hybridoma supernatant, mAb 2-4A5-4 (NeoMarkers) or isotype control mAbs (diluted in negative hybridoma supernatant), and then stimulated with 100 ng/ml hCSF-1 or left unstimulated for 5 min at 37° C. Cell layers were then lysed and total proteins were extracted. Ten µg proteins were analyzed by probing Western blots with either the rabbit pAb c-fms/CSF-1R H300 or the rabbit pAb p-c-fms/CSF-1R (Tyr708)-R (Santa Cruz Biotechnology), followed by goat anti-rabbit immunoglobulins$^{HRP}$.

In the absence of CSF-1, neither CXIIG6 hybridoma supernatant nor mAb 2-4A5-4 induced receptor phosphorylation as seen with the antibody specific for CSF-1R phosphorylated at position 708, showing that mAb CXIIG6 alone does not exert an agonistic effect. Upon stimulation with CSF-1, CSF-1R was phosphorylated on Tyr708 and the amount of CSF-1R decreased in isotype control-treated cells compared with unstimulated cells, reflecting receptor degradation (data not shown). Pretreatment with CXIIG6 hybridoma supernatant or with mAb 2-4A5-4 did not enhance CSF-1R disappearance. Phosphorylation of CSF-1R was decreased following treatment with CXIIG6 hybridoma supernatant or with mAb 2-4A5-4. These results show that mAb CXIIG6 is able to block the CSF-1-dependent phosphorylation of CSF-1R.

Cross-Reactivity of mAb CXIIG6

The cross-reactivity of mAb CXIIG6 was tested by ELISA on a series of purified soluble receptors belonging to the type III subfamily of tyrosine kinase receptors and showing homology to CSF-1R in their extracellular Ig-like domains: soluble VEGFR-1, VEGFR-2, Flt-3 and PDGFRβ (all four expressed as Fc fusion proteins), as well as PDGFRα and SCFR (c-kit) were obtained from R&D Systems and used for coating an ELISA plate. Soluble EGFR (R&D Systems), from the EGFR subfamily of tyrosine kinase receptors, was used as a negative control.

Figure 5:
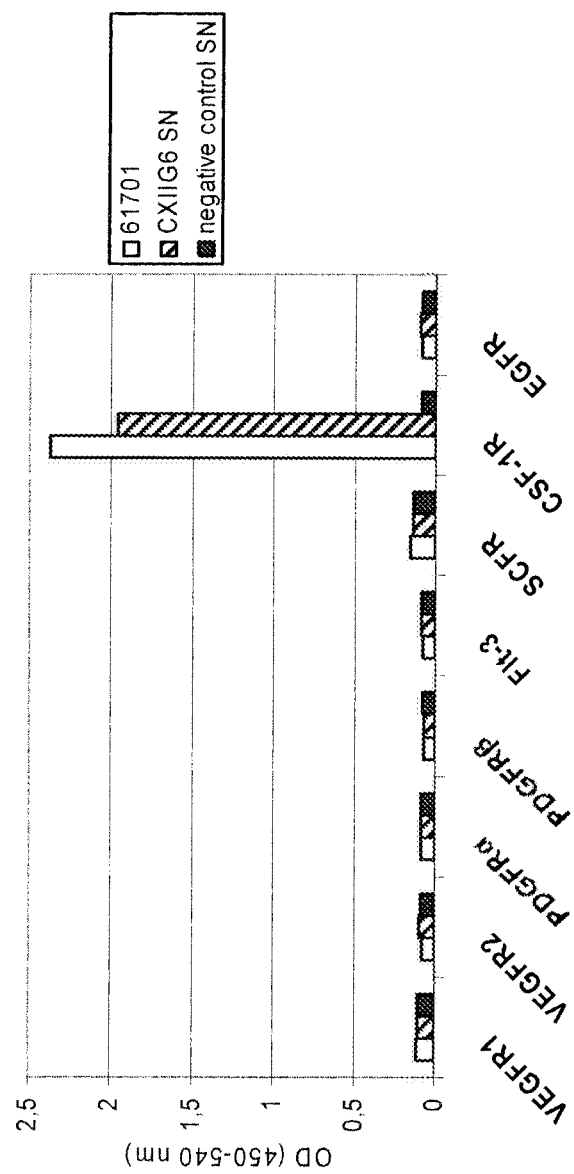
FIG. 5 shows the non-cross-reactivity of mAb CXIIG6 with other tyrosine kinase receptors having homology to CSF-1R ('SN' means hybridoma supernatant).

Culture supernatants from either hybridoma CXIIG6 (CXIIG6 SN) or a negative control hybridoma, or the anti-CSF-1R mouse IgG$_1$ 61701 (R&D Systems) were incubated on the coated ELISA plate at antibody concentrations of 500 ng/ml. After washing the ELISA plate, bound antibodies were revealed using peroxidase-conjugated goat anti-mouse Ig (Sigma) and OD (450-540 nm) was measured. Results depicted in FIG. 5 show that like mAb 61701, CXIIG6 strongly bound the CSF-1R while no specific signal was detected on any other tyrosine kinase receptor. This shows that among the various type III tyrosine kinase receptors tested, CXIIG6 is specific for CSF-1R.

Construction of Expression Vectors for mAb CXIIG6

The OptiCHO™ Antibody Express Kit (Invitrogen, Catalog No. 12762-019) was used for the cloning of the genes encoding the CXIIG6 heavy and light chains in order to produce the mAb CXIIG6 in DG44 mammalian cell line. The OptiCHO™ Antibody Express Kit includes: (1) The pOptiVEC™ vector, a bicistronic plasmid that allows the cloning of the gene of interest downstream of CMV promoter. The transcription of the gene of interest is separated from the dihydrofolate reductase (DHFR) auxotrophic selection marker by an internal ribosome entry site (IRES), allowing transcription of the gene of interest and of the selection marker on the same mRNA; (2) The pcDNA™3.3 vector that allows the cloning of the gene of interest downstream of CMV promoter. The pcDNA™3.3 contains a neomycin resistance gene allowing selection using Geneticin®. The pOptiVEC™ and pcDNA™3.3 vectors contain the TK poly-A sequence which directs proper processing of the 3' end of the mRNA of the gene of interest.

Specific primers (see Table 4) were synthesized and used for the PCR amplification and cloning of the entire CXIIG6 heavy chain and light chain genes (respectively SEQ ID NO:1 and SEQ ID NO:3; see respectively FIG. 6 and FIG. 7). The backward primers included the Kozak consensus sequence for efficient eukaryotic translation (KOZAK M. An analysis of 5'-noncoding sequences from 699 vertebrate messenger RNAs. *Nucleic Acids Res.* 1987, 15(20): 8125-8148).

TABLE 4

| Primer | Sequence |
| --- | --- |
| OTG18929 | GCCGCCACCATGTACTTGGGACTGAACTATGTATTC (SEQ ID NO: 30) |
| OTG18930 | GGAGATCTTCATTTACCCGGAGTCCGGGA (SEQ ID NO: 31) |
| OTG18931 | GCCGCCACCATGAGTGTGCCCACTCAGGTCCTG (SEQ ID NO: 32) |
| OTG18932 | GCCCGGGCTAACACTCATTCCTGTTGAAGCTC (SEQ ID NO: 33) |

CXIIG6 heavy chain was PCR amplified by using OTG18929 and OTG18930 with plasmid pTG17753 (FIG. 8) as template, and cloned into the vector pOptiVEC™-TOPO® (pOptiVEC™-TOPO® TA Cloning® Kit, Invitrogen, Catalog no. 12744-017-01) and the pcDNA™3.3-TOPO® vectors (pcDNA™3.3-TOPO® TA Cloning® Kit, Invitrogen, Catalog No. K8300-01) to obtain respectively pTG17786 and pTG17789.

CXIIG6 light chain was PCR amplified by using OTG18931 and OTG18932 with plasmid pTG17727 (FIG. 9) as template, and cloned into the vector pOptiVEC™-TOPO® (pOptiVEC™-TOPO® TA Cloning® Kit, Invitrogen, Catalog no. 12744-017-01) and the pcDNA™3.3-TOPO® vectors (pcDNA™3.3-TOPO® TA Cloning® Kit, Invitrogen, Catalog No. K8300-01) to obtain respectively pTG17788 and pTG17787.

The nucleotide sequence of the whole expression cassette, including CMV promoter and TK polyA signal of pTG17786, pTG17787, pTG17788 and pTG17789 were sequenced and found in compliance with their theoretical sequences.

Generation of Chimeric Antibodies from mAb CXIIG6

The variable domains of mAb CXIIG6 were combined with human constant regions.

To generate the chimeric light chain (named Chimeric CXIIG6 Igκ chain), a theoretical sequence was designed by joining the sequence encoding the CXIIG6 VK Domain (from SEQ ID NO:3) to the sequence encoding for the human IGKC region (GenBank accession number: J00241). This XbaI NotI DNA fragment kept the same non translated sequence at 5' end, including Kozak sequence, as the one used in the murine version (as in pTG17787 and pTG17788 described above). The chimeric CXIIG6 light chain sequence was codon optimized for expression in CHO, assembled from synthetic oligonucleotides, and subcloned into pOptiVEC™ (FIG. 10) via XbaI NotI by GeneArt AG. The obtained chimeric CXIIG6 light chain (variable and constant regions) codon optimized nucleic acid sequence is as set forth in SEQ ID NO:34. The obtained plasmid was named pTG17895 (FIG. 11).

To generate the chimeric heavy IgG$_1$ and IgG4 chains (respectively named Chimeric CXIIG6 IgG$_1$ and Chimeric CXIIG6 IgG4 chains), the theoretical sequences were designed by joining the sequence encoding the CXIIG6 VH Domain (from SEQ ID NO:1) to the sequences encoding either for the human IGHG1C region (GenBank accession number: J00228) or for the human IGHG4C region (GenBank accession number: K01316). These XbaI NotI DNA fragments kept the same non translated sequence at 5' end, including Kozak sequence, as the one used in the murine version (as in pTG17786 and pTG17789 as described above). The chimeric CXIIG6 heavy chains were then codon optimized for expression in CHO, synthesized and cloned into pTG17812 (FIG. 12) via XbaI NotI by GeneArt AG. The obtained chimeric CXIIG6 IgG$_1$ heavy chain (variable and constant regions) codon optimized nucleic acid sequence is as set forth in SEQ ID NO:35 and the obtained plasmids was named pTG17868 (FIG. 13). The obtained chimeric CXIIG6 IgG4 heavy chain (variable and constant regions) codon optimized nucleic acid sequence is as set forth in SEQ ID NO:36 and the obtained plasmids was named pTG17869 (FIG. 14).

Generation of Humanized Antibodies from mAb CXIIG6

To generate the humanized light chain variants, amino acid substitutions according to Table 2 were performed within the light-chain variable region as set forth in SEQ ID NO:9.

DNA sequences were designed by joining modified sequences bearing substitutions of the CXIIG6 VK Domain (from SEQ ID NO:3) to the sequence encoding for the human IGKC region (GenBank accession number: J00241). This XbaI NotI DNA fragment kept the same non translated sequence at 5' end including Kozak sequence as the one used in the murine version (as in pTG17787 and pTG17788 as described above). The humanized CXIIG6 light chain sequences were then codon optimized for expression in CHO, assembled from synthetic oligonucleotides and cloned into pOptiVEC™ (FIG. 10) via XbaI NotI by GeneArt AG. The obtained humanized CXIIG6 light chain variants and plasmids are listed in FIG. 15.

To generate the humanized heavy chain variants, amino acid substitutions according to Table 1 were performed within the heavy-chain variable region as set forth in SEQ ID NO:6.

DNA sequences were designed by joining modified sequences bearing substitutions of the CXIIG6 VH Domain (from SEQ ID NO:1) to the sequences encoding for the human IGHG1C region (GenBank accession number: J00228). The XbaI ApaI DNA fragments kept the same non translated sequence at 5' end including Kozak sequence as used the one in the murine version (as in pTG17786 and pTG17789 as described above). The DNA sequences were then codon optimized for expression in CHO, synthesized and cloned into pTG17812 (FIG. 12) via XbaI ApaI by GeneArt AG. The obtained humanized CXIIG6 IgG$_1$ heavy chain variants and plasmids are listed in FIG. 16.

In Vitro Inhibitory Activities of Recombinant Murine CXIIG6 and Chimeric CXIIG6 IgG1

To determine whether purified recombinant murine CXIIG6 (as previously described) and its chimeric IgG$_1$ variant (chimeric CXIIG6 IgG$_1$ as previously described) were able to block soluble human CSF-1R, dose-response studies were performed in the M-NFS-60 cell proliferation and osteoclast differentiation models (as previously described). Purified polyclonal murine IgG2a from Rockland (Rockland, 010-0141) and a chimeric IgG$_1$ produced by the applicant were tested in parallel as control antibodies. Blocking effect was evaluated by exposing cells to concentration ranges of active anti-CSF-1R antibodies, as measured by antigen binding in a SPR biosensor assay. Comparison between mAbs CXIIG6 and their respective control mAb was done by loading equal amounts of total antibody (SPR biosensor assay by Fc binding).

M-NFS-60 bioassay: In the M-NFS-60 bioassay, cells were treated with 0.23 ng/ml to 0.5 µg/ml active mAbs CXIIG6 (recombinant murine CXIIG6; chimeric CXIIG6 IgG$_1$) or corresponding concentrations of control mAbs in the presence of 50 ng/ml human soluble CSF-1R and 1 ng/ml human CSF-1 for 48 h. Results depicted in FIG. 17 show that M-NFS-60 cell growth increased in response to increasing concentrations of both mAbs CXIIG6 (recombinant murine CXIIG6; chimeric CXIIG6 IgG$_1$) demonstrating that they antagonized the binding of soluble CSF-1R to CSF-1 (mean+/−SEM of triplicate wells). Chimeric CXIIG6 IgG$_1$ was as effective as recombinant murine CXIIG6 in restoring cell proliferation. Control murine IgG2a and chimeric IgG₁ had no effect on CSF-1 neutralization by soluble CSF-1R over their respective concentration range. These results show that purified recombinant murine CXIIG6 and chimeric CXIIG6 IgG₁ inhibit soluble human CSF-1R.

Osteoclast bioassay: In the osteoclast bioassay, elutriated human monocytes were incubated for 8 days with 0.85 ng/ml to 0.62 µg/ml active mAbs CXIIG6 (recombinant murine CXIIG6; chimeric CXIIG6 IgG₁) in the presence of 25 ng/ml CSF-1 (ImmunoTools) and 40 ng/ml RANKL. The medium and all added agents were replenished on day 4 and 6 and total MMP-9 was measured in culture media conditioned from day 6 to 8. Results depicted in FIG. 18 show that in comparison with control antibodies, recombinant murine CXIIG6 and its chimeric variant (chimeric CXIIG6 IgG₁) each significantly reduced MMP-9 production which parallels osteoclast differentiation, indicating that growth retardation occurred (FIG. 18; mean+/−SEM of triplicate wells).

These results further demonstrate that purified recombinant murine CXIIG6 and chimeric CXIIG6 IgG₁ inhibit the function of cell-surface CSF-1R.

Epitope Mapping of the Antibody of the Invention Versus Commercial Antibodies These experiments have been designed in order to determine the epitope localization of the antibodies of the present invention, and more precisely to determine if they are binding identical or different epitopes than a number of commercially-available anti-CSF-1R antibodies.

Chimeric CXIIG6 (chCXIIG6) of the Invention, mAb 3291 (murine IgG₁, clone 61701, R&D Systems MAB3291) and mAb JF14 (murine IgG₁, Santa Cruz sc-80174) bind human but not murine CSF-1R. Monoclonal antibodies 3291 and JF14 have being selected as they have been generated against the N-terminal moiety of human CSF-1R. In order to map the mAb binding sites on CSF-1R, truncated mutants of human CSF-1R and chimeras between human and murine D1-D3 CSF-1R fused to Histidine tags were constructed (see FIGS. 19 and 20 for details). These constructs were expressed as secreted proteins using CHO cells. Expression of constructs was checked by immunoblot analysis using an anti-His tag antibody for detection. All constructs were captured on ELISA plate by incubating CHO culture supernatant into wells coated with an Anti-His tag antibody. Antibodies were biotinylated using Biotin-NHS (Sigma ref B3295-10MG). Biotinylated antibodies were added to each well and binding was detected with streptavidin-HRP. Biotinylated Rituximab (Du et al., 2007, J. Biol. Chem. 282 (20), 15073-15080, NCBI Access Numbers 2OSL_H & 2OSL_L) was used as a negative isotype control (not binding to CSF-1R). Results are summarized in FIG. 19.

Results:

As expected, Rituximab does not bind to any tested construct. Chimeric CXIIG6, mAb 3291 and mAb JF14 are able to bind the isolated domain 1 (D1) of human CSF-1R (see construct pTG18038; FIG. 19). Furthermore, replacement of human D1 by murine D1 completely abolishes the binding of the three mAb (see construct pTG18003; FIG. 19). Results obtained using constructs pTG18015 and pTG18000 combining human and murine D1 subdomains show that binding of mAbs 3291 and JF14 requires both the N-terminus and the central part of the human CSF-1R D1 domain, while binding of the monoclonal antibody of the Invention requires only the N-terminal part of the human domain D1 (see construct pTG18016; FIG. 19).

These data show that the epitope of the monoclonal antibody of the Invention binds to human CSF-1R on a different epitope than monoclonal antibodies 3291 and JF14. Interestingly, the N-terminal parts of human and murine CSF-1R differ by only 4 residues: I20A, V27G, K33E and A36E (starting methionine is residue 1).

Monoclonal Antibodies H19K12, H27K5 and H27K15

The generation of hybridoma CXIIG6, producing mouse IgG$_{2a}$ with blocking activity to human CSF-1R function, has been described above. The heavy and light chains of CXIIG6 IgG$_{2a}$ were cloned and sequenced (see FIGS. 6 and 7). A chimeric version of the monoclonal antibody (chCXIIG6) was constructed, combining the variable domains VH and VL of mAb CXIIG6 with human IgG₁ constant regions (see above). To increase homology to human antibody sequences and diminish potential immunogenicity of the monoclonal antibodies, humanized variants were generated by introducing mutations in the VH and VL domains (see FIGS. 15 and 16).

262 versions of the humanized monoclonal antibody of the Invention were expressed transiently in Chinese Hamster Ovary (CHO) cells and tested for their CSF-1R binding capacity. Out of this first screening, thirty-one humanized CXIIG6 variants (hCXIIG6) were selected on the basis of (i) affinity to human CSF-1R, (ii) highest homology with human germline sequences (preferably said homology is at least 76%, more preferably at least 85%) and (iii) lowest in silico immunogenicity. Affinity studies using quartz crystal microbalance (Attana) technology showed that all selected hCXIIG6 variants had similar affinities for recombinant human CSF-1R, in the range of $10^{-9}$ to $10^{-10}$ M like parental mAb chCXIIG6. Three out of 30 humanized variants characterized by high affinity to CSF-1R, highest degree of human homology and lowest in silico immunogenicity were selected for further studies: H19K12, H27K5 and H27K15.

Biochemical Characterization of Monoclonal Antibody H27K15 of the Invention

A—Radiolabeling of H27K15 antibody with Iodine-$^{125}$

Materials

Monoclonal antibody H27K15 of the Invention was provided as an aqueous solution (PBS pH7.5) at 2.1 mg/mL concentration.

Iodine-$^{125}$ radionuclide was purchased from Perkin Elmer as sodium iodide in $10^{-5}$N sodium hydroxide (specific activity: 643.8 GBq/mg—radionuclide purity: 99.95%).

Chloramine-T (N-chloro-p-toluenesulfonamide, PM: 227.6 g.mol$^{-1}$), sodium metabisulfite (PM=190.1 g.mol$^{-1}$), bovine serum albumin (BSA) and trichloroacetic acid were purchased from Sigma.

Phosphate-buffered saline 0.1M, pH7.2 was prepared in our laboratory.

Method

To 100 µg of antibody, 1.2 mCi of Na$^{125}$I solution (44.4 MBq) and 7.6 µL of freshly prepared chloramine-T solution (1 mg/mL in phosphate buffer) were added. After 2 min at room temperature, the reaction was stopped by adding 12.7 µL of sodium metabisulfite (1 mg/mL in phosphate buffer).

Nonincorporated Iodine-$^{125}$ was removed by gel filtration on Sephadex G-25 column (PD-10, Pharmacia) previously saturated with elution buffer (phosphate buffer 0.1M pH7.2/ 0.5% BSA). The column was eluted in 40 aliquots of 0.5 mL. Radioactivity in each fraction was measured in an automatic Gamma Counter calibrated for iodine-$^{125}$ radionuclide (Wallace Wizard 2470 automatic Gamma-counter calibrated for iodine-$^{125}$ radionuclide—Perkin Elmer) and the fractions containing the desired radioiodinated product were pooled.

The radiochemical purity of radiolabeled compound was estimated by ITLC analysis performed on Gelman Sciences precoated silica gel plates, using 10% TCA as eluant.

Results and Characteristics of Radiolabeled Antibody Solutions

Before purification, radiochemical yield as determined by ITLC was 97.8%.

The characteristics of radiolabeled antibody solution are summarized below:

|  | $^{125}$I-H27K15 |
| --- | --- |
| Molecular weight (Da) | 150 000 |
| Concentration  μg/mL | 58.19 |
| nM | 387.93 |
| Specific activity (mCi/mg) | 10.51 |
| Ratio Iodine/Antibody | 0.72 |
| Volumic activity | 612.57 |
| Radiochemical purity (%) | 99.84 |

The purity and integrity of the radiolabeled antibody were assessed by sodium dodecyl sulfatepolyacrylamide gel electrophoresis (SDS-PAGE) under reducing and non-reducing conditions. A broad range molecular weight standard (Biorad Laboratories) consisting of 10 molecular weight markers from 10 to 250 kDa was used to calibrate the gel. Gels were stained by coomassie blue. In a second step, gels were dried and exposed on a screen for autoradiography using a PhosphorImager 445 SI (Amersham Biosciences). ImageJ software (Molecular Dynamics) was used for data analysis.

Electrophoretic profiles obtained after coomassie blue staining and autoradiography are identical. In non-reducing conditions, one major band at 150 kDa is visualized, corresponding to entire IgG molecule. In reducing conditions, 50 kDa and 25 kDa bands are detected, corresponding to heavy and light chains of antibody, respectively. These electrophoresis results confirm that Chloramine-T method doesn't affect the integrity of antibody.

B—Binding Assays of Radiolabeled H27K15 Antibody on EL4-CSF-1R Cells b1 Measurement of Affinity Binding of $^{125}$I-H27K15

The equilibrium dissociation constant (KD) was used as a measurement of binding affinity. The KD for $^{125}$I-H27K15 antibody was determined by a saturation assay where an increasing concentration of radiolabeled antibody was added to a constant number of cells.

Materials
Solution of radiolabeled antibody in PBS containing 0.5% BSA

|  | $^{125}$I-H27K15 |
| --- | --- |
| Specific activity (mCi/mg) | 10.51 |
| Radiopurity (%) | 99.84 |
| Dilution in PBS containing 0.5% BSA | Range of concentrations: 4.5 μg/mL to 0.54 ng/mL (30 nM to 3.6 pM) 2-fold dilution series |

Solutions of radiolabeled antibody with 100-fold molar excess of unlabeled antibody (non-specific binding): A solution containing 45 μg/mL of unlabeled antibody and 0.45 μg/mL of radiolabeled antibody was prepared and then 4-fold dilution series in PBS/BSA 0.5% were performed.

Cells: A suspension of EL4-CSF-1R cells at $40 \times 10^6$ cells/mL in PBS containing 0.5% BSA was prepared.

Method

The EL4-CSF-1R cells were incubated ($2 \times 10^6$ in 50 μL PBS/BSA 0.5%) with increasing concentrations of radiolabeled antibody in a final volume of 150 μL for 1 h on ice with agitation.

Non-specific binding was determined by co-incubating an excess of unlabeled antibody (100-fold molar excess).

Following incubation, reaction mixtures were overlaid onto 200 μL of a dibutylphtalate oil cushion and centrifuged in microfuge tubes at 12000 rpm for 3 min. Tubes were frozen in liquid nitrogen and the tips of the tubes containing the cell pellets were cut off for determination of radioactivity using a Wallace Wizard 2470 automatic Gamma-counter calibrated for iodine-$^{125}$ radionuclide (efficiency: 63%).

Non-specific binding was determined by measuring the bound radioactivity of four point concentration of radiolabeled antibody containing 100-fold molar excess of unlabeled antibody. A graph plotting bound fraction versus free fraction was made and a linear regression was used in order to definite the slope of the straight line. Specific binding was defined by subtraction of the binding observed in the presence (non-specific binding) from that observed in the absence (total binding) of excess unlabeled antibody.

Results

The affinity constant of humanized $^{125}$I-H27K15 antibody for EL4-CSF-1R cells and the maximum binding sites per cell were determined by Prism software.

The binding characteristics of $^{125}$I-H27K15 antibody for EL4-CSF-1R cells are summarized below:

|  | $^{125}$I-H27K15 |
| --- | --- |
| Dissociation constant |  |
| in nM | 0.7161 ± 0.061 |
| in μg/mL | 0.107 ± 0.009 |
| Bmax in cpm | 26422 ± 552 |
| Number of binding sites per cell | 3393 ± 71 | b2 Measurement of Inhibition Constant of Unlabeled H27K15

The aim of this study was to determine whether the affinity of the immunoreactive radiolabeled antibody is the same as of the unlabeled antibody. A radiolabeled displacement binding assay was performed with a constant concentration of radiolabeled antibody and serial dilutions of unlabeled antibody.

Material

| Solutions of radiolabeled antibody in PBS containing 0.5% BSA | $^{125}$I-H27K15 |
|---|---|
| Specific activity (mCi/mg) | 10.51 |
| Radiopurity (%) | 99.84 |
| Concentration | 1.5 nM |

Solutions of Unlabeled Antibody:

A solution at 450 nM (67.5 μg/mL) was prepared and then 2.5-fold dilution series in PBS/BSA 0.5% were performed. Range concentration: 450 nM to 7.56 μM.

Cells:

A suspension of EL4-CSF-1R cells at $40 \times 10^6$ cells/mL in PBS containing 0.5% BSA was prepared.

Method:

The cells were incubated ($2 \times 10^6$ in 50 μL PBS/BSA 0.5%) with 50 μL of radiolabeled antibody at 1.5 nM in the absence (total binding: control well) and in the presence of variable concentrations (above mentioned) in 50 μL of unlabeled antibody for 1 h on ice with agitation.

Following incubation, reaction mixtures were overlaid onto 200 μL of dibutylphtalate oil cushion and centrifuged in microfuge tubes at 12000 rpm for 3 min. Tubes were frozen in liquid nitrogen and the tips of the tubes containing the cell pellets were cut off for determination of radioactivity using a gamma counter.

Percentage of relative binding of radiolabeled antibody was calculated as:

$$\frac{\text{Radioactivity in control well}}{\text{Radioactivity in test well} \times 100}$$

(Control well is that with no unlabeled antibody present)

Results

The binding data are presented in FIG. 21.

The $IC_{50}$ value obtained from competition curve was determined by Prism software and was converted to an absolute inhibition constant Ki using the Cheng-Prusoff equation (Biochem. Pharmacol., 22, 3099-3108, 1973):

$$Ki = \frac{IC_{50}}{1 + ([L]/K_D)}.$$

[L] is concentration of radiolabeled antibody used in the assay $IC_{50}$ is concentration of unlabeled antibody necessary to achieve 50% inhibition of radiolabeled antibody The $IC_{50}$ value and the inhibition constant are summarized below:

| | H27K15 |
|---|---|
| IC50 | |
| In nM | 0.856 ± 0.090 |
| In μg/mL | 0.128 ± 0.013 |
| Inhibition constant | |
| In nM | 0.504 ± 0.053 |
| In μg/mL | 0.076 ± 0.008 | b3 Competition Study Between $^{125}$I-H27K15 and Various Antibodies

Materials

Solution of Radiolabeled H27K15 Antibody in PBS Containing 0.5% BSA:

As above

Solutions of Unlabeled Antibody

The different antibodies are presented in table as follows:

| | H19K12 | H27K5 | chCXIIG6 | 3291 | JF14 | 2-4A5 |
|---|---|---|---|---|---|---|
| Concentration of stock solution (mg/mL) | 2.4 | 0.3 | 1 | 8.92 | 2 | 2 |

For each antibody, a solution at 450 nM (67.5 μg/mL) was prepared and then 2.5-fold dilution series in PBS/BSA 0.5% were performed. Range concentration: 450 nM to 7.56 pM.

Cells:

A suspension of EL4-CSF-1R cells at $40 \times 10^6$ cells/mL in PBS containing 0.5% BSA was prepared.

Method

The cells were incubated ($2 \times 10^6$ in 50 μL PBS/BSA 0.5%) with 50 μL of $^{125}$I-H27K15 antibody at 1.5 nM in the absence (total binding: control well) and in the presence of variable concentrations (above mentioned) in 50 μL of unlabeled competitor for 1 h on ice with agitation.

Following incubation, reaction mixtures were overlaid onto 200 μL of dibutylphtalate oil cushion and centrifuged in microfuge tubes at 12000 rpm for 3 min. Tubes were frozen in liquid nitrogen and the tips of the tubes containing the cell pellets were cut off for determination of radioactivity using a gamma counter.

Percentage of relative binding of radiolabeled antibody was calculated as:

$$\frac{\text{Radioactivity in test well} \times 100}{\text{Radioactivity in control well}}$$

Control well is that with no competitor present.

Results

Figure 22:
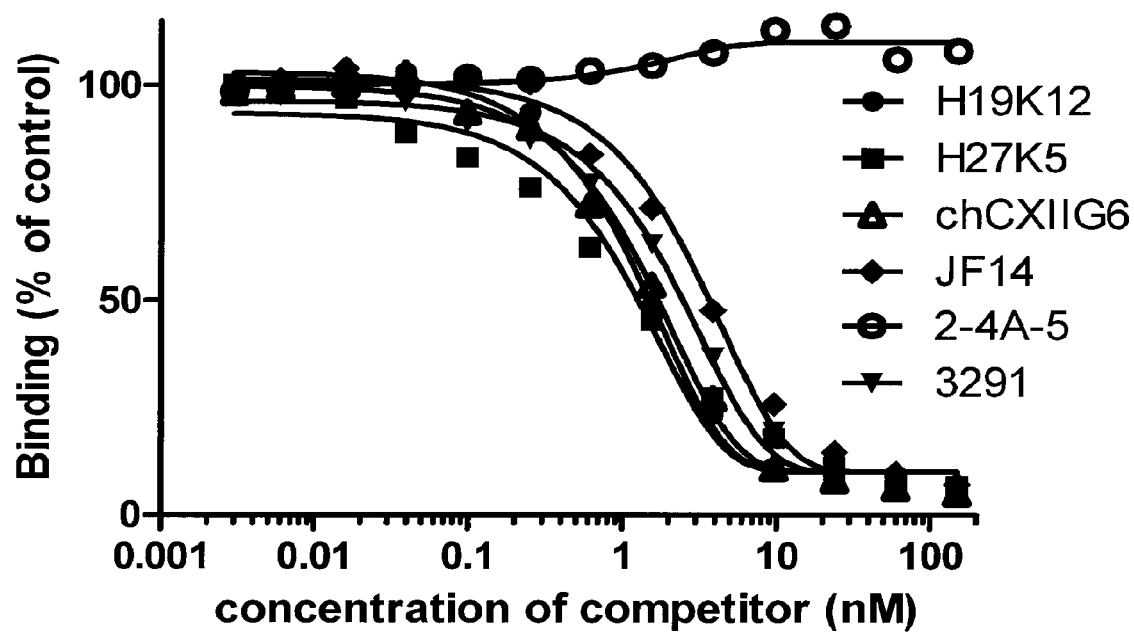

The binding data are presented FIG. 22

The $IC_{50}$ value obtained from competition curve was determined by Prism software and was converted to an absolute inhibition constant Ki using the Cheng-Pursoff equation:

$$Ki = \frac{IC_{50}}{1 + ([L]/K_D)}.$$

[L] is concentration of $^{125}$I-H27K15 antibody used in the assay $IC_{50}$ is concentration of competitor necessary to achieve 50% inhibition of $^{125}$I-H27K15 antibody $K_D$ is affinity constant of $^{125}$I-H27K15 antibody.

For each competitor, the $IC_{50}$ values and Ki constants are summarized below:

| | chCXIIG6 | H19K12 | H27K5 | 3291 | JF14 | 2-4A5 |
|---|---|---|---|---|---|---|
| IC50 (nM) | 1.483 ± 0.220 | 1.280 ± 0.246 | 0.998 ± 0.173 | 2.176 ± 0.281 | 3.025 ± 0.568 | No competition |
| Ki (nM) | 0.874 ± 0.130 | 0.754 ± 0.145 | 0.588 ± 0.102 | 1.281 ± 0.165 | 1.781 ± 0.334 | |

The affinity of the monoclonal antibodies of the Invention (H27K15, chCXIIG6, H19K12 and H27K5) are quite similar with a value of Ki from 0.5 to 0.8 nM.

The Ki values of commercial monoclonal antibodies 3291 and JF14 are higher than 1 nM. Consequently, these antibodies have lower affinity for CSF-1R antigen than the monoclonal antibodies of the Invention.

C—Competitive Binding Assays of Human CSF-1 to D1-D5 Human CSF-1R

CSF-1(1-444) was biotinylated using Biotin-NHS (Sigma ref. B3295-10MG). Biotinylated CSF-1(100 μl/well at 0.012 μg/ml) was added to wells coated with FC-D1-D5 human CSF-1R (100 μL/well at 1 μg/mL) (R&D systems ref. 329-MR-100) and bound molecule were detected using streptavidin-HRP. For competition experiments, increasing amounts of monoclonal antibodies (100 μl/well from 0.030 μg/ml to 200 μg/ml) were pre-, co- or post-incubated with biotinylated CSF-1.

We have tested commercial monoclonal antibody 3291 (R&D Systems ref. MAB3291), one monoclonal of the Invention H27K15, monoclonal antibody X (WO2009/026303) as positive control as it is known to compete with CSF-1 binding to its receptor, and Rituximab as negative control.

In case of pre-incubation, monoclonal antibodies were incubated with coated human CSF-1R one hour before addition of biotinylated CSF-1.

In case of post-incubation, biotinylated CSF-1 was incubated with coated human CSF-1R one hour before addition of monoclonal antibodies.

In case of co-incubation, biotinylated CSF-1 and monoclonal antibodies were incubated together with coated human CSF-1R.

Results:

It has been previously shown (see above) that both 3291 and H27K15 antibodies recognize one epitope (ie: Ig-like domain 1) that is different from the one recognized by the positive control antibody X known to bind to the same binding site as CSF-1 (i.e.: in Ig-like domains 2-3). Here, we show that contrary to the positive control, both 3291 and H27K15 antibodies are partial competitors of CSF-1 binding, even at high dose of antibody (i.e. ~100 fold the IC50). In all the settings (pre, co or post incubations), and at saturation doses, H27K15 is able to decrease the CSF-1 binding to CSF-1R by approximately 10 to 20% (see FIGS. 23, 24 and 25) while antibody 3291 is able to decrease the same binding by approximately 30 to 40% depending of the experimental setting.

Accordingly the monoclonal of the present Invention are able to partially prevent binding of CSF1 to its receptor CSF-1R.

This has been confirmed in the following experiment.

ELISA microplates were coated with 0.1 μg (i.e. 100 μL at 1 μg/ml) of human CSF1 1-444 (Geneart—see SEQ ID NO:47, FIGS. 32A through 32H). 100 μL of Fc-D1-D5 human CSF-1R(R&D systems ref 329-MR-100) at 0.125 μg/mL was coincubated in presence of increasing concentration of antibody. Bound Fc-D1-D5 human CSF-1R to CSF1 was detected using anti-IgG-Fc-human-HRP (Bethyl A80-204P). Since the antibody used for detection binds human Fc, murine antibody CXIIG6 instead of antibody H27K15 was used for competition. Competitor mAb X (WO2009/026303) was used as positive control as it is known to bind human CSF-1R at the same site as human CSF-1. Rat IgG2a was used as negative control (irrelevant isotypic antibody that does not bind hCD115).

Results:

mAb X, as indicated in WO2009/026303, inhibits totally the binding of CSF1 (1-444) to Fc-D1-D5 human CSF-1R as expected for a competitive antibody. Both 3291 and mCXIIG6, decrease only partially the Fc-D1-D5 human CSF-1R binding to CSF1 even at high dose of antibody (i.e. 100 μg/mL). mCXIIG6 and 3291 decreased the binding of CSF1 to Fc-hCD115 by approximately 5-10% and 10-20%, respectively (see FIG. 26). These results are in agreement with those described above demonstrating a partial inhibition of CSF1 binding to Fc-D1-D5 human CSF-1R by H27K15 or mAb 3291.

FIG. 26 shows the partial decrease of binding of recombinant human Fc-human D1-D5 CD115 to human CSF1 by various mAb (coincubation experiment). Human CSF1 (0.1 μg/mL) was coated on 96 wells plate and incubated 1 hour 45 min with a mix (coincubation experiment) of recombinant Fc-D1-D5 human CSF-1R (0.125 μg/mL) and increasing concentrations of mAb. The CD115 that bind to hCSF-1 was detected using anti-human Fc-IgG conjugated to HRP.

D—Competition Study Between $^{125}$I-H27K15 and IL-34, Known as One Natural Ligands of CSF-1R Receptor Materials Solutions of Radiolabeled Antibody in PBS Containing 0.5% BSA $^{125}$I-H27K15 (as above)

Solutions of Ligands:

Recombinant human IL-34 (26.1 kDa) was purchased by R&D Systems at a concentration of 0.422 mg/mL. A solution at 450 nM was prepared and then 2.5-fold dilution series in PBS/BSA 0.5% were performed. Range concentration: 450 nM to 7.56 μM.

Cells:

A suspension of EL4-CSF-1R cells at $40 \times 10^6$ cells/mL in PBS containing 0.5% BSA was prepared.

Method

Two different protocols were performed during this competition study with the natural ligands.

The first one, the cells were coincubated ($2 \times 10^6$ in 50 μL PBS/BSA 0.5%) with 50 μL of $^{125}$I-H27K15 antibody at 1.5 nM in the absence (total binding: control well) and in the presence of variable concentrations (above-mentioned) in 50 μL of unlabeled competitor for 1 h on ice with agitation.

The second protocol was to incubate EL4-CSF-1R cells with increasing concentrations of ligand for 30 min on ice prior to addition of radiolabeled H27K15 antibody. Then, the second incubation was also performed on ice for 1 hour with agitation.

For the two experiments, reaction mixtures were overlaid onto 200 μL of dibutylphtalate oil cushion and centrifuged in microfuge tubes at 12000 rpm for 3 min. Tubes were frozen in liquid nitrogen and the tips of the tubes containing the cell pellets were cut off for determination of radioactivity using a gamma counter.

Percentage of relative binding of radiolabeled antibody was calculated as:

$$\frac{\text{Radioactivity in test well} \times 100}{\text{Radioactivity in control well}}$$

(Control Well is that with No Ligand Present)

Results: No displacement of $^{125}$I-H27K15 antibody binding was observed. Consequently, H27K15 antibody and IL-34 ligand recognize different epitopes of the CSF-1R antigen.

Moreover, competition binding study between $^{125}$I-IL-34 and humanized H27K15 antibody has been performed which has shown that $^{125}$I-IL-34 binding was not displaced with increasing concentration of H27K15 antibody illustrating herein that the antibody of the Invention does not compete with IL-34 for binding to the CSF-1R receptor.

hCXIIG6 Variants H27K5, H27K15 and H19K12 Biological Characterization

A. Expression and Purification of Monoclonal Antibodies

Chimeric CXIIG6, hCXIIG6 variants H19K12, H27K5, H27K15 and rituximab were expressed either by transient transfection of adherent CHO-K1 or CHO-DG44 cells or by polyclonal pools of stable CHO-DG44 transfectants.

B. Specificity of H27K5, H27K15 and H19K12 for CSF-1R Among Other Tyrosine Kinase Receptors Method Microtiter plates (Maxisorp, Nunc) were coated with 300 ng per well of each of the following soluble receptors, purchased from R&D Systems: CSF-1R$_{20-512}$-Fc (cat. 329-MR/CF), (EGFR)$_2$-Fc-6×his (cat. 1129-ER), Flt-3-Fc-6×his (cat. 368-ST/CF), PDGFRβ-Fc-6×his (cat. 385-PR/CF), vascular endothelial growth factor receptor (VEGFR)$_2$-Fc-6×his (cat. 357-KD/CF), VEGFR1-Fc-6×his (cat. 321-FL-050), human SCFR (cat. 332-SR/CF) and PDGFRα ECDs (cat. 322-PR/CF. Fifty μl of either H27K5, H27K15, H19K12 mAbs or rituximab (500 ng/ml in PBS) were added to the wells and plates were incubated for 1 h at 37° C. To control efficient coating of the wells, anti-human IgG (goat anti-human IgG, Sigma cat. I3382) was also incubated with wells coated with receptor-human Fc fusion proteins Flt-3-Fc-, PDGFRβ-Fc, VEGFR2-Fc, VEGFR1-Fc, while PDGFRα- and SCFR-coated wells were incubated with respectively anti-PDGF-Rα (mouse IgG$_1$, R&Dsystems cat. MAB322) and anti-SCF-R goat IgG (R&DSystems cat. AF332). Antibody binding was detected with horseradish peroxidase (HRP)-conjugated Abs directed against either human Ig kappa light chain (Bethyl Laboratories, cat. A80-115P), goat IgG (Santa Cruz cat. sc2033) or mouse Ig (Sigma cat. A 0412). Following revelation with tetramethylbenzidine (Sigma, cat. T8665) (0.1 mg/ml in 0.05 M sodium acetate, 0.05 M citric acid, H$_2$O$_2$ 1/7000), absorbance was measured at 450 nm and corrected by subtraction of absorbance at 540 nm using a spectrophotometer (Berthold, Tristar LB941).

Results

Like chCXIIG6, none of the humanized variants showed immunoreactivity to any of the other receptors ECD, while they strongly bound to immobilized CSF-1R ECD (FIG. 27). This result shows that humanization did not alter the specificity of mAbs H19K12, H27K5 and H27K15 for CSF-1R among other tyrosine kinase receptors.

C. CSF-1R-Blocking Activity of hCXIIG6 Variants

C.1 Blockade of Soluble CSF-1R-Fc Tested in the M-NFS-60 Cell Proliferation Assay Method M-NFS-60 cells were washed twice with complete RPMI-1640 medium without CSF-1 and incubated overnight in the same medium for CSF-1 deprivation. To assay for neutralization of soluble human CSF-1R, 5 ng of human CSF-1R20-512-Fc were incubated for 30 min in white 96-well microplates (ViewPlate™-96, Packard) with serial dilutions of antibodies (H27K5, H27K15, H19K12 mAbs, chCXIIG6 or rituximab in complete RPMI-1640 medium. 104 CSF-1-deprived cells were then added to the culture wells together with 0.1 ng of human CSF-1 in a final assay volume of 100 μl. Cells were incubated for 48 h at 37° C. and proliferation was quantified after incorporation of 5-bromo-2'-deoxyuridine (BrdU) for 2 h using the Cell Proliferation ELISA from Roche (cat. #11647223001) according to the manufacturer's protocol. OD were measured in a spectrophotometer (Berthold Tristar LB941).

Results

The mouse myelogenous leukemia cell line M-NFS-60 is dependent on CSF-1 for its growth and has previously been used to demonstrate the CSF-1R-blocking activity of murine mAb CXIIG6. In this assay, M-NFS-60 cells are cultivated with human CSF-1 and human soluble homodimeric disulfide-linked CSF-1R20-512-Fc. Capture of CSF-1 by soluble CSF-1R leads to inhibition of cell proliferation. Addition of antibodies neutralizing human CSF-1R prevents CSF-1 capture by soluble CSF-1R and restores cell growth. In the presence of negative control rituximab, soluble CSF-1R completely inhibited the proliferation of M-NFS-60 cells mediated by CSF-1 (FIG. 28). H19K12, H27K5 and H27K15 produced a dose-dependent neutralization of soluble CSF-1R20-512-Fc and restored cell proliferation, as did chCXIIG6. ND50 (neutralization dose giving 50% of maximal CSF-1R-blocking effect), calculated with the GraphPad Prism software using a 5-parameter logistic equation, were similar for the 3 hCXIIG6 variants tested (29.8, 30.7 and 29.1 ng/ml for respectively H19K12, H27K5 and H27K15) and did not appear significantly different from that of parental mAb chCXIIG6 (18.1 ng/ml).

C.2 Blockade of Cell-Surface CSF-1R Tested in the AML5-Cell Based Assay

Methods

Immunocytochemistry and Flow Cytometry Analysis of AML5 Cells

AML5 cells (OCI-AML5, DSMZ cat. ACC-247) were analyzed by immunocytochemistry and flow cytometry. 5×105 cells were incubated for 30 min on ice with either anti-human CSF-1R mAb 3291 (murine IgG$_1$, clone 61701, 10 μg/ml) (R&D Systems cat. #MAB3291), murine IgG$_1$ isotype control (R&D Systems cat. #MAB002, 10 μg/ml), chCXIIG6 (10 μg/ml) or rituximab in 100 μl PBS. Cells were then labeled for 30 to 45 min on ice with either phycoerythrine-conjugated goat anti-mouse Ig (BD Pharmingen cat. #550589) or fluorescein isothiocyanate-conjugated anti-human IgG F(ab')2 (Millipore cat. #AQ112F).

Effect of CSF-1 on AML5 Cell Proliferation

AML5 cells were plated at 2.5 E4 cells/100 μl/well in either flat-bottomed (in experiments 1 and 2, TPP cat. #92096) or round-bottomed (in experiment 3, Falcon cat. #3077) 96-well plates. One hundred μl of medium containing human CSF-1 was added per well. Cells were cultured for 48 h and their proliferation was measured after a 4-h incorporation of BrdU, using the Cell Proliferation ELISA from Roche (cat. #11647223001) according to the manufacturer's protocol. OD were measured in a spectrophotometer (Berthold, Tristar LB941). Mean OD+/−sem were calculated from quadruplicate wells and plotted against log [CSF-1] (ng/ml) using GraphPad Prism to fit a nonlinear regression curve using a 3-parameter equation.

Effect of hCXIIG6 Variants on AML5 Cell Proliferation

Cells were cultured and plated in 96-well plates as described above. Graded amounts of chCXIIG6, H27K15, H27K5, H19K12 or negative control rituximab were added in 50 µl medium. Following a 30-min incubation at 37° C., 50 µl of medium containing 40 ng/ml hCSF-1 were added per well. Each experiment was performed on 4 identical 96-well plates, each comprising duplicates of each mAb concentration. Cells were cultured for 48 h and their proliferation was measured after a 4-h incorporation of BrdU as above. Result from each plate was first analyzed using GraphPad Prism to fit a nonlinear regression curve with a 5-parameter equation. Plates giving results fitted by GraphPad Prism for at least 3 out of the 4 tested mAbs were selected to calculate the means+/−sem. Thus, experiments 1 and 2 were analyzed based on the results from 2 out of 4 plates (means calculated from quadruplicate OD values) and experiment 3 based on the results from 3 out of 4 plates (means calculated from 6 OD values). EC50 and R squares were calculated by GraphPad Prism for each mAb tested.

Results

Colony-stimulating factor-1 has been reported to stimulate the growth of the human acute myeloid leukemia cell line OCI-AML5 (AML5) (Drexler H G, Zaborski M, Quentmeier H., 2007. Cytokine response profile of human myeloid factor-dependent leukaemia cell lines. Leukemia 11:701-8). AML5 cells were analyzed by immunocytochemistry and flow cytometry. Staining was positive with the commercial anti-hCSF-1R mouse IgG1 3291 (compared with mouse IgG$_1$ isotype control) and with chCXIIG6 (compared with rituximab), showing that AML5 cells expressed surface CSF-1R (FIG. 29A).

In order to set up a model for studying the effect of CSF-1R blockage, it was necessary to first verify that CSF-1 induced a dose-dependent increase in AML5 cell proliferation. FIG. 29B shows that while AML5 are capable of growing in the absence of exogenous CSF-1, addition of the growth factor in the culture medium increases cell proliferation in a dose-dependent manner. AML5 cells are therefore not strictly dependent on CSF-1 for their growth, but they are CSF-1-responsive.

The effects of hCXIIG6 variants and of chCXIIG6 were then tested on AML5 cells cultured with 10 ng/ml CSF-1, a concentration inducing near to maximal proliferation (FIG. 29B). FIG. 29C shows the results from 3 independent experiments. Humanized variants H27K5, H27K15 and H19K12 as well as chCXIIG6 induced a dose-dependent decrease in AML5 cell proliferation. Variability was observed between the experiments, reflected by differences in the EC50 for each mAb and the rather low R squares calculated using GraphPad Prism, particularly in experiment 1 (FIG. 29D). Therefore, hCXIIG6 variants could not be reliably ranked according to their EC50 in this assay. All 3 hCXIIG6 variants appeared equally potent in inhibiting the CSF-1-dependent proliferation of AML5 cells.

C.3 Non-Agonistic Effect on CSF-1R Signaling and Inhibitory Effect on CSF-1-Dependent Phosphorylation Methods B4-800-5 is a recombinant cell line obtained by stable transfection of murine NIH/3T3 cells with pTG17366, an expression plasmid encoding human CSF-1R. B4-800-5 cells were seeded at 2×10$^5$ cells per 60-mm Petri dishes and cultivated for 72 h. Cells were serum-deprived by culture in 1 ml DMEM medium containing 1% FCS at 37° C. for 1 h before the experiments.

For studying CSF-1R blockade or the effects of antibodies in the absence of cross-linking, cells were treated with 1 ml DMEM-1% FCS containing mAb chCXIIG6, H19K12, H27K5, H27K15 or human IgG$_1$ isotype control rituximab for 1 h at 37° C. One hundred ng/ml hCSF-1 (ImmunoTools cat. 11343115) were added to the cell culture for 5 min at 37° C., or cells were left unstimulated.

In the antibody cross-linking experiment, cells were treated with 1 ml DMEM-1% FCS containing mAb chCXIIG6, H19K12, H27K5, H27K15, human IgG$_1$ isotype control rituximab, recombinant mouse IgG2$_a$ CXIIG6 or mouse IgG2$_a$ isotype control (R&D Systems cat. MAB003) for 1 h on ice. Cells were washed with ice-cold PBS. Twenty µg/ml polyclonal goat anti-mouse IgG (R&D Systems cat. AF007), 20 µg/ml polyclonal goat anti-human IgG Fc$^{HRP}$ (Jackson cat. 109-035-098) or 100 ng/ml hCSF-1 were added to the cells for 10 min at 37° C., or cells were left untreated. Medium was removed and cell layers were lysed by adding extraction buffer (62 mM Tris, 10% glycerol, 2% SDS, 100 mM DTT, pH 6.8) in the Petri dishes. Cell extracts were analyzed on Western blots, probed with the following antibodies: polyclonal rabbit anti-phospho-CSF-1R$^{Tyr708}$ (Santa Cruz Biotechnology cat sc-33358-R), polyclonal rabbit anti-CSF-1R(H300, Santa Cruz Biotechnology cat. sc-13949, dilution 1/200) and monoclonal mouse anti-β-actin (Sigma-Aldrich cat. A2228, dilution 1/2000) for the detection of tyrosine$^{708}$-phosphorylated CSF-1R, total CSF-1R and β-actin, respectively. Rabbit and mouse primary antibodies were detected with polyclonal goat anti-rabbit or rabbit anti-mouse Ig$^{HRP}$ (DakoCytomation cat. P0448, P0260) respectively.

Results

We investigated the effects of hCXIIG6 variants H19K12, H27K5 and H27K15 and of chCXIIG6 on the CSF-1-dependent phosphorylation of tyrosine$^{708}$ and their lack of agonistic effect. In the absence of CSF-1, neither mAb induced receptor phosphorylation when tested at either 0.1, 1 or 10 µg/ml, as seen with the antibody specific for CSF-1R phosphorylated on tyrosine$^{708}$. This showed that all CXIIG6-mAb derivatives, either in chimeric or humanized forms, did not exert any agonistic effect when applied alone on B4-800-5 cells.

Upon CSF-1 stimulation, a band of ~150 kDa corresponding to full-length CSF-1R was phosphorylated and total cellular CSF-1R was decreased in cells cultured with rituximab isotype control or without antibody. Three other bands of lower molecular weights were detected with the anti-phospho-CSF-1R$^{Tyr\ 708}$ antibody. When B4-800-5 cells were incubated at 37° C. with chCXIIG6 or hCXIIG6 variants before stimulation with CSF-1, the intensities of the 4 bands recognized by the anti-phospho-CSF-1R$^{Tyr\ 708}$ mAb were decreased compared to those observed in rituximab-treated cells. Reduction of the intensity of the 150-kDa band was comparable to that previously observed with hybridoma-derived CXIIG6 in similar conditions. The decrease in intensity of the two lower bands appeared more drastic. The inhibitory effects of chCXIIG6 and the hCXIIG6 variants on CSF-1R Tyr$^{708}$ phosphorylation were observed at 0.1, 1 and 10 µg/ml.

To anticipate the potential development of a humoral response to hCXIIG6 in treated patients mAb (human anti-human antibody response), we next investigated the effect of mAb cross-linking by secondary anti-IgG Abs on CSF-1R receptor phosphorylation. Cross-linking of mouse CXIIG6 produced only a faint band of 150 kDa detected with the anti-phospho-CSF-1R$^{Tyr708}$ antibody as previously observed with hybridoma-derived CXIIG6 and a slight down-regulation of total CSF-1R was detectable, possibly reflecting a weak activation of CSF-1R. Upon cross-linking, hCXIIG6 variants and chCXIIG6 also produced a 150 kDa band with low intensity. The intensity of the 150 kDa phosphorylated CSF-1R band was extremely weak compared to that observed after stimulation with 100 ng/ml CSF-1. The lower MW bands induced by CSF-1 were not detected by the anti-CSF-1R$^{Tyr\ 708}$ antibody after cross-linking of any anti-CSF-1R mAb derivative, either chCXIIG6 or hCXIIG6 variants.

These experiments demonstrate that hCXIIG6 variants H19K12, H27K5 and H27K15, like chCXIIG6, are capable of partially inhibiting CSF-1-dependent phosphorylation of CSF-1R and have no direct agonistic activity on CSF-1R. Cross-linking of mAbs on the cell surface has only a minimal effect on CSF-1R phosphorylation.

D—Cytotoxicity to EL4-CSF-1R Target Cells

Method

The EL4-CSF-1R recombinant cell line was generated by stable transfection of the murine lymphoma-derived T cell line EL4 (ATCC cat. TIB-39) with a lentiviral vector encoding human full-length CSF-1R. Surface CSF-1R expression was verified by immunostaining with mAbs CXIIG6 (mouse IgG2a) or 3291 and flow cytometry analysis (data not shown).

EL4-CSF-1R cells were washed in DMEM complete medium, resuspended in the same medium and seeded in 96-well plates at 2×10$^4$ cells per well in 50 µl. Cells were opsonized for 45-60 min on ice with 50 µl of antibodies diluted in culture medium. 50 µl of human peripheral blood mononuclear cells (PBMC) were then added at various effector-to-target (E:T) ratios. Humanized CXIIG6 variants, chCXIIG6 and negative control Rituximab were tested at 10 ng/ml, 0.3 and 10 µg/ml. Control wells containing 150 µl of culture medium, target cells or PBMC alone were run in parallel to measure (i) culture medium (CM) background, (ii) culture medium+Lysis Solution background, (iii) target cell spontaneous release (SR), (iv) effector cell spontaneous release at each PBMC concentration and (v) target cell maximal release (MR) in presence of Lysis Solution. Plates were centrifuged at 250×g for 4 min and incubated overnight at 37° C. The next day, 15 µl of Lysis Solution 10×(Promega cat. G182A) were added to control wells containing culture medium or target cells alone and plates were further incubated for 45 min at 37° C. Lactate deshydrogenase (LDH) was quantified in the culture supernatants using the CytoTox 96® Non-Radioactive Cytotoxicity Assay (Promega cat. G1780) according to the manufacturer's instructions. Absorbance was recorded at 490 nm using the TriStar LB 941 reader and the MikroWin 2000 software from Berthold Technologies.

Mean CM background was subtracted from experimental, target SR and effector SR values. Mean CM+Lysis Solution background was subtracted from target MR values. Statistical analysis was done using the OD values, after subtraction of mean CM and SR controls, with GraphPad Prism software using a non-parametric Mann-Whitney one-tailed t-test (for comparing chCXIIG6 or each hCXIIG6 variant with rituximab) or two-tailed t-test (for comparing each hCXIIG6 variant with chCXIIG6). Percent lysis was calculated using the following formula:

$$\% \text{ lysis} = \frac{\text{experimental} - \text{mean target } SR - \text{mean effector } SR}{\text{mean target } MR - \text{mean target } SR} \times 100$$

Results

The ADCC activities of chCXIIG6 and of hCXIIG6 variants (human IgG$_1$) were tested on target EL4-CSF-1R cells, using PBMC from different blood donors.

Effector cells from donor #1 were used at an E:T ratio of 25:1 (FIG. 30A). In this experiment, above 10% direct lysis was observed in the absence of mAb, which may reflect the activity of NK cells contained in the PBMC. Values obtained with negative control rituximab were in the same range. It had been verified by flow cytometry analysis that EL4-CSF-1R cells did not bind rituximab (data not shown). At 10 ng/ml mAb, no specific lysis (above the unspecific lysis observed in the presence of rituximab) was found with the anti-CSF-1R mAbs. At 0.3 µg/ml mAb, chCXIIG6 induced above 20% cytotoxicity. Lysis by the 3 hCXIIG6 variants was in the same order of magnitude. At high mAb concentrations (10 µg/ml), all 3 hCXIIG6 variants produced close to 35% cytotoxicity, while lysis by chCXIIG6 remained under 20%.

Another experiment was performed using effector cells from donor #2 at E:T ratios of 25:1, 50:1 or 100:1 (FIG. 30B). Direct lysis was not detected, in contrast with the first experiment. Background cytotoxicity was lower than 10% with rituximab at all E:T ratios tested. Results were in good correlation with those from the previous experiment: no specific lysis was observed at low mAb concentrations (10 ng/ml) but at 0.3 and 10 µg/ml, chCXIIG6 and the 3 hCXIIG6 variants induced significant specific lysis of EL4-CSF-1R cells. At both these mAb concentrations and all E:T ratios tested, lysis of target cells was again higher with H27K5, H27K15 and H19K12 than with chCXIIG6 (p=0.02).

These results demonstrate that chCXIIG6 and the hCXIIG6 variants have the potential of killing target cells expressing surface CSF-1R.

Therapeutic Effect of Chimeric and Humanized Anti-CSF-1R mAbs in the BeWo Tumor Model Since chCXIIG6 and hCXIIG6 variants are specific for human CSF-1R and do not recognize its murine homolog, their in vivo effects can only be investigated in mouse models using human CSF-1R-positive tumors. However, in the absence of human CSF-1, human CSF-1R remains inactive and blockade of its function cannot be studied. Moreover, blockade of CSF-1R-positive host cells (tumor-associated macrophages, osteoclasts), which is expected to provide therapeutic benefit, is not feasible in this model system. In the following experiments using human CSF-1R-positive BeWo tumors, only the cytotoxic effects of the mAbs on the tumor cells may result in therapeutic efficacy.

BeWo Human Choriocarcinoma Cells Express Surface CSF-1R

BeWo cells cultivated in vitro were immunostained with mAb H27K15 (lead humanized anti-CSF-1R) and fluorescence was analyzed by confocal microscopy. The specific staining observed with H27K15, compared with negative control rituximab, shows that BeWo cells express human CSF-1R on their surface. BeWo cells do not secrete CSF-1, as found by ELISA titration of the culture supernatants (result not shown).

A solid tumor derived from BeWo cells implanted subcutaneously in NMR1 nude mice was included in OCT for analysis by immunohistochemistry. Frozen tissue sections were stained with the murine version of CXIIG6 or an isotype control. A strong specific staining was observed throughout the tumor, reflecting both cell surface and cytoplasmic expression of hCSF-1R in BeWo tumor cells in vivo.

Experiment 1

Therapeutic Effect of Chimeric CXIIg6 in the BeWo Choriocarcinoma Tumor Model

Four million BeWo cells were implanted subcutaneously in the flanks of NMR1 nude mice. A group of 11 mice was treated with 3 injections of chimeric CXIIG6 (chCXIIG6, 50 mg/kg in PBS, IP, administered at days 1, 3 and 7) while another group of 11 mice was treated with rituximab isotype control based on the same scheme. Inhibition of tumor growth (FIG. 31A) and prolongation of mouse survival (FIG. 31B) were observed in chCXIIG6-treated mice, showing that targeting human CSF-1R-positive BeWo tumors with this mAb has therapeutic effect.

Experiment 2

Therapeutic Effect of Chimeric CXIIG6 and Humanized H27K15 in the BeWo Choriocarcinoma Tumor Model The above protocol was repeated, with 2 modifications:
chCXIIG6 or humanized H27K15 mAbs were tested (10 mice/group) and compared with isotype control rituximab
mAbs were injected 3 times a week for 3 weeks, instead of one week only
Prolongation of the treatment with chCXIIG6 or with H27K15 did not improve the results in terms of tumor growth inhibition or mouse survival, as compared with the first experiment. However, both mAbs inhibited tumor growth as compared with the rituximab isotype control group. In the case of H27K15, the reduction in tumor volumes was statistically significant at day 14 using Mann-Whitney test and close to significant at later time points (day 17 and 21). With chCXIIG6, reduction in tumor volumes was close to statistically significant.

REFERENCES

WO 01/30381
WO 03/059395
WO 2005/068503
EP 1488792 A
US 2005059113
EP 901463 B
EP 83286 A
EP 206920 A
U.S. Pat. No. 5,747,323
WO 94/28152
WO 97/04119
WO 94/18992
WO 96/17070
WO2009/026303
SHERR. Colony-stimulating factor-1 receptor. blood. 1990, vol. 75, no. 1, p. 1-12.
HUME, et al. Regulation of CSF-1 receptor expression. *Molecular reproduction and development*. 1997, vol. 46, no. 1, p. 46-52.
Roussel AND SHERR, 1989, PNAS, 86, 7924-7927
ASHMUN et al., 1989, Blood, 73, 827-837
KLUGER, et al. Macrophage colony-stimulating factor-1 receptor expression is associated with poor outcome in breast cancer by large cohort tissue microarray analysis. *Clinical cancer research*. 2004, vol. 10, no. 1, p. 173-7.
SCHOLL, et al. Anti-colony-stimulating factor-1 antibody staining in primary breast adenocarcinomas correlates with marked inflammatory cell infiltrates and prognosis. *Journal of the National Cancer Institute*. 1994, vol. 86, no. 2, p. 120-6.
CHAMBERS, et al. Overexpression of epithelial macrophage colony-stimulating factor (CSF-1) and CSF-1 receptor: a poor prognostic factor in epithelial ovarian cancer, contrasted with a protective effect of stromal CSF-1. *Clinical Cancer Research*. 1997, vol. 3, no. 6, p. 999-1007.
BAÏOCCHI, et al. Expression of the macrophage colony-stimulating factor and its receptor in gynecologic malignancies. *Cancer*. 1991, vol. 67, no. 4, p. 990-6.
KIRMA, et al. Elevated expression of the oncogene c-fms and its ligand, the macrophage colony-stimulating factor-1, in cervical cancer and the role of transforming growth factor-beta1 in inducing c-fms expression. *Cancer res*. 2007, vol. 67, no. 5, p. 1918-26.
HEMMERLEIN, et al. Expression of acute and late-stage inflammatory antigens, c-fms, CSF-1, and human monocytic serine esterase 1, in tumor-associated macrophages of renal cell carcinomas. *Cancer immunology, immunotherapy*. 2000, vol. 49, no. 9, p. 485-92.
IDE, et al. Expression of colony-stimulating factor 1 receptor during prostate development and prostate cancer progression. *Proc. Natl. Acad. Sci. U.S.A*. 2002, vol. 99, no. 22, p. 14404-9.
RAMBALDI, et al. Expression of the macrophage colony-stimulating factor and c-fms genes in human acute myeloblastic leukemia cells. *Journal of Clinical Investigation*. 1988, vol. 81, no. 4, p. 1030-5.
SCHOLL, et al. Anti-colony-stimulating factor-1 antibody staining in primary breast adenocarcinomas correlates with marked inflammatory cell infiltrates and prognosis. *Journal of the National Cancer Institute*. 1994, vol. 86, no. 2, p. 120-6.
TANG, et al. M-CSF (monocyte colony stimulating factor) and M-CSF receptor expression by breast tumor cells: M-CSF mediated recruitment of tumor infiltrating monocytes?. *Journal of cellular biochemistry*. 1992, vol. 50, no. 4, p. 350-6.
SCHOLL, et al. Circulating levels of colony-stimulating factor 1 as a prognostic indicator in 82 patients with epithelial ovarian cancer. *British journal of cancer*. 1994, vol. 69, no. 2, p. 342-6.
SCHOLL. Circulating levels of the macrophage colony stimulating factor CSF-1 in primary and metastatic breast cancer patients. A pilot study. *Breast cancer research and treatment*. 1996, vol. 39, no. 3, p. 275-83.
DORSCH, et al. Macrophage colony-stimulating factor gene transfer into tumor cells induces macrophage infiltration but not tumor suppression. *European journal of immunology*. 1993, vol. 23, no. 1, p. 186-90.
WANG, et al. Induction of monocyte migration by recombinant macrophage colony-stimulating factor. *Journal of immunology*. 1988, vol. 141, no. 2, p. 575-9.

FILDERMAN, et al. Macrophage colony-stimulating factor (CSF-1) enhances invasiveness in CSF-1 receptor-positive carcinoma cell lines. *Cancer res.* 1992, vol. 52, no. 13, p. 3661-6.

DORSCH, et al. Macrophage colony-stimulating factor gene transfer into tumor cells induces macrophage infiltration but not tumor suppression. *European journal of immunology.* 1993, vol. 23, no. 1, p. 186-90.

SCHOLL. Circulating levels of the macrophage colony stimulating factor CSF-1 in primary and metastatic breast cancer patients. A pilot study. *Breast cancer research and treatment.* 1996, vol. 39, no. 3, p. 275-83.

BARON, et al. Modulation of MHC class II transport and lysosome distribution by macrophage-colony stimulating factor in human dendritic cells derived from monocytes. *Journal of cell science.* 2001, vol. 114, no. pt5, p. 999-1010.

CECCHINI, et al. Role of CSF-1 in bone and bone marrow development. *Molecular reproduction and development.* 1997, vol. 46, no. 1, p. 75-83.

BRUZZANITI, et al. Molecular regulation of osteoclast activity. *Reviews in endocrine.* 2006, vol. 7, no. 1-2, p. 123-39.

CICEK, et al. Breast cancer bone metastasis and current small therapeutics. *Cancer metastasis reviews.* 2006, vol. 25, no. 4, p. 635-44.

KITAURA, et al. The journal of clinical investigation. M-CSF mediates TNF-induced inflammatory osteolysis. 2005, vol. 115, no. 12, p. 3418-27.

MARSHALL, et al. Blockade of colony stimulating factor-1 (CSF-I) leads to inhibition of DSS-induced colitis. *Inflammatory bowel diseases.* 2007, vol. 13, no. 2, p. 219-24.

JOSE, et al. Blockade of macrophage colony-stimulating factor reduces macrophage proliferation and accumulation in renal allograft rejection. *American journal of transplantation.* 2003, vol. 3, no. 3, p. 294-300.

KUTZA, et al. Macrophage colony-stimulating factor antagonists inhibit replication of HIV-1 in human macrophages. *Journal of immunology.* 2000, no. 164, p. 4955-4960.

SMITH, et al. Identification of common molecular subsequences. *Journal of Molecular Biology.* 1981, no. 147, p. 195-7.

HARLOW. Antibodies: A Laboratory manual. 2nd edition. Cold Spring Harbor: Laboratory press, 1988.

HAMMERLING, et al. Monoclonal Antibodies and T Cell Hybridomas. New York: Elsevier, 1981. p. 563-681.

SMITH, et al. Identification of common molecular subsequences. *Journal of Molecular Biology.* 1981, no. 147, p. 195-7.

LENNARD. Standard protocols for the construction of scFv libraries. *Methods in molecular biology.* 2002, no. 178, p. 59-71.

POLJAK. Production and structure of diabodies. *Structure.* 1994, vol. 2, no. 12, p. 1121-3.

HUDSON, et al. High avidity scFv multimers; diabodies and triabodies. *Journal of immunological methods.* 1999, vol. 231, no. 1-2, p. 177-89.

KIPRIYANOV. Generation of bispecific and tandem diabodies. *Methods in molecular biology.* 2002, no. 178, p. 317-31.

HOLLIGER, et al. Engineered antibody fragments and the rise of single domains. *Nature biotechnology.* 2005, vol. 23, no. 9, p. 1126-36.

HOOGENBOOM, et al. Natural and designer binding sites made by phage display technology. *Immunology today.* 2000, vol. 21, no. 8, p. 371-8.

MARKS, et al. By-passing immunization: building high affinity human antibodies by chain shuffling. *Biotechnology.* 1992, vol. 10, no. 7, p. 779-83.

BARBAS, et al. In vitro evolution of a neutralizing human antibody to human immunodeficiency virus type 1 to enhance affinity and broaden strain cross-reactivity. *Proceedings of the National Academy of Sciences of the United States of America.* 1994, vol. 91, no. 9, p. 3809-13.

SCHIER. Identification of functional and structural aminoacid residues by parsimonious mutagenesis. *Gene.* 1996, vol. 169, no. 2, p. 147-55.

YELTON. Affinity maturation of the BR96 anti-carcinoma antibody by codon-based mutagenesis. *J. immunol.* 1995, vol. 155, no. 4, p. 1994-2004.

JACKSON, et al. In vitro antibody maturation. Improvement of a high affinity, neutralizing antibody against IL-1 beta. *J. immunol.* 1995, vol. 154, no. 7, p. 3310-9.

HAWKINS, et al. Selection of phage antibodies by binding affinity. Mimicking affinity maturation. *Journal of molecular biology.* 1992, vol. 226, no. 3, p. 889-96.

SMITH, et al. Identification of common molecular subsequences. *Journal of Molecular Biology.* 1981, no. 147, p. 195-7.

BRENNAN, et al. Preparation of bispecific antibodies by chemical recombination of monoclonal immunoglobulin G1 fragments. *Science.* 1985, vol. 229, no. 4708, p. 81-3.

SHALABY, et al. Development of humanized bispecific antibodies reactive with cytotoxic lymphocytes and tumor cells overexpressing the HER2 protooncogene. *The Journal of experimental medicine.* 1992, vol. 175, no. 1, p. 217-25.

KOSTELNY, et al. Formation of a bispecific antibody by the use of leucine zippers. *J. immunol.* 1992, vol. 148, no. 5, p. 1547-33.

ZAPATA, et al. Engineering linear F(ab')2 fragments for efficient production in *Escherichia coli* and enhanced antiproliferative activity. *Protein engineering* 1995, vol. 8, no. 10, p. 1057-62.

HERMANSON. Bioconjugate techniques. Academic press, 1996.

HERMANSON. Bioconjugate techniques. Academic press, 1996. p. 118-228.

HERMANSON. Bioconjugate techniques. Academic press, 1996. p. 229-285.

FELGNER, et al. Cationic liposome mediated transfection. *Proceedings of the Western Pharmacology Society.* 1989, vol. 32, p. 115-21.

HODGSON, et al. Virosomes: cationic liposomes enhance retroviral transduction. *Nature biotechnology.* 1996, vol. 14, no. 3, p. 339-42.

REMY, et al. Gene transfer with a series of lipophilic DNA-binding molecules. *Bioconjugate chemistry.* 1994, vol. 5, no. 6, p. 647-54.

LATHE, et al. Plasmid and bacteriophage vectors for excision of intact inserts. *Gene.* 1987, vol. 57, no. 2-3, p. 193-201.

LUPTON, et al. Mapping genetic elements of Epstein-Barr virus that facilitate extrachromosomal persistence of Epstein-Barr virus-derived plasmids in human cells. *Molecular and cellular biology.* 1985, vol. 5, no. 10, p. 2533-42.

YATES, et al. Stable replication of plasmids derived from Epstein-Barr virus in various mammalian cells. *Nature.* 1985, vol. 313, no. 6005, p. 812-5.

SUMMERS, et al. Multimerization of high copy number plasmids causes instability: ColE1 encodes a determinant essential for plasmid monomerization and stability. *Cell.* 1984, vol. 36, no. 4, p. 1097-103.

SUTTER, et al. Nonreplicating vaccinia vector efficiently expresses recombinant genes. *Proc. Natl. Acad. Sci. U.S.A.* 1992, vol. 89, no. 22, p. 10847-51.

MEYER, et al. Mapping of deletions in the genome of the highly attenuated vaccinia virus MVA and their influence on virulence. *The Journal of general virology.* 1991, vol. 72, no. Pt5, p. 1031-8.

SUTTER, et al. A recombinant vector derived from the host range-restricted and highly attenuated MVA strain of vaccinia virus stimulates protective immunity in mice to influenza virus. *Vaccine.* 1994, vol. 12, no. 11, p. 1032-40.

GRAHAM, et al. Methods in molecular biology. Edited by MURREY. The human press inc, 1991. p. 109-128.

ZAKHARCHUK, et al. Physical mapping and homology studies of egg drop syndrome (EDS-76) adenovirus DNA. *Archives of virology.* 1993, vol. 128, no. 1-2, p. 171-6.

SPIBEY, et al. Molecular cloning and restriction endonuclease mapping of two strains of canine adenovirus type 2. *The Journal of general virology.* 1989, vol. 70, no. Pt 1, p. 165-72.

JOUVENNE, et al. Cloning, physical mapping and cross-hybridization of the canine adenovirus types 1 and 2 genomes. *Gene.* 1987, vol. 60, no. 1, p. 21-8.

MITTAL, et al. Development of a bovine adenovirus type 3-based expression vector. *The Journal of general virology.* 1995, vol. 76, no. Pt 1, p. 93-102.

BISCHOFF, et al. An adenovirus mutant that replicates selectively in p53-deficient human tumor cells. *Science.* 1996, vol. 274, no. 5286, p. 373-6.

HEISE, et al. An adenovirus E1A mutant that demonstrates potent and selective systemic anti-tumoral efficacy. *Nature Medicine.* 2000, vol. 6, no. 10, p. 1134-9.

FUEYO, et al. A mutant oncolytic adenovirus targeting the Rb pathway produces anti-glioma effect in vivo. *Oncogene.* 2000, vol. 19, no. 1, p. 2-12.

MCIVOR. Human purine nucleoside phosphorylase and adenosine deaminase: gene transfer into cultured cells and murine hematopoietic stem cells by using recombinant amphotropic retroviruses. *Molecular and cellular biology.* 1987, vol. 7, no. 2, p. 838-46.

TABIN, et al. Adaptation of a retrovirus as a eukaryotic vector transmitting the herpes simplex virus thymidine kinase gene. *Molecular and cellular biology.* 1982, vol. 2, no. 4, p. 426-36.

TAKEBE, et al. SR alpha promoter: an efficient and versatile mammalian cDNA expression system composed of the simian virus 40 early promoter and the R-U5 segment of human T-cell leukemia virus type 1 long terminal repeat. *Molecular and cellular biology.* 1988, vol. 8, no. 1, p. 466-72.

CHEN, et al. Breast cancer selective gene expression and therapy mediated by recombinant adenoviruses containing the DF3/MUC1 promoter. *The Journal of clinical investigation.* 1995, vol. 96, no. 6, p. 2775-82.

SCHREWE, et al. Cloning of the complete gene for carcinoembryonic antigen: analysis of its promoter indicates a region conveying cell type-specific expression. *Molecular and cellular biology.* 1990, vol. 10, no. 6, p. 2738-48.

VILE, et al. Use of tissue-specific expression of the herpes simplex virus thymidine kinase gene to inhibit growth of established murine melanomas following direct intratumoral injection of DNA. *Cancer res.* 1993, vol. 53, no. 17, p. 3860-4.

HARRIS, et al. Gene therapy for cancer using tumor-specific prodrug activation. *Gene therapy.* 1994, vol. 1, no. 3, p. 170-5.

KANAI, et al. In vivo gene therapy for alpha-fetoprotein-producing hepatocellular carcinoma by adenovirus-mediated transfer of cytosine deaminase gene. *Cancer res.* 1997, vol. 57, no. 3, p. 461-5.

PEREZ. Principles and practice of radiation oncology. 2nd edition. LIPPINCOTT, 1992.

KOZAK M. An analysis of 5'-noncoding sequences from 699 vertebrate messenger RNAs. *Nucleic Acids Res.* 1987, 15(20): 8125-8148.

CHOTHIA and LESK. Canonical structures for the hypervariable regions of immunoglobulins (1987) J Mol. Biol. 1987 Aug. 20; 196(4):901-17.

The invention claimed is:

1. An isolated, recombinant or purified antibody that specifically binds to human CSF-1R, wherein
   (i) it comprises:
   (a) a heavy-chain variable region being defined by the following formula
   FR1-CDR1-FR2-CDR2-FR3-CDR3-FR4
   wherein:
   FR1, FR2, FR3, and FR4 are each framework regions;
   CDR1, CDR2, and CDR3 are each complementarity determining regions;
   wherein:
   CDR1 has at least five consecutive amino acids of the sequence starting in position 45 and finishing in position 54 of SEQ ID NO:2, wherein said at least five consecutive amino acids include SEQ ID NO:11;
   CDR2 has at least five consecutive amino acids of the sequence starting in position 66 and finishing in position 87 of SEQ ID NO:2, wherein said at least five consecutive amino acids include SEQ ID NO:12; and
   CDR3 has at least five consecutive amino acids of the sequence starting in position 117 and finishing in position 126 of SEQ ID NO:2, wherein said at least five consecutive amino acids include SEQ ID NO:13;
   and
   (b) a light-chain variable region being defined by the following formula
   FR1-CDR1-FR2-CDR2-FR3-CDR3-FR4
   wherein:
   FR1, FR2, FR3, and FR4 are each framework regions;
   CDR1, CDR2, and CDR3 are each complementarity determining regions;
   wherein:
   CDR1 has at least five consecutive amino acids of the sequence starting in position 44 and finishing in position 56 of SEQ ID NO:4, wherein said at least five consecutive amino acids include SEQ ID NO:14;
   CDR2 has at least five consecutive amino acids of the sequence starting in position 66 and finishing in position 76 of SEQ ID NO:4, wherein said at least five consecutive amino acids include SEQ ID NO:15; and
   CDR3 has at least five consecutive amino acids of the sequence starting in position 109 and finishing in position 117 of SEQ ID NO:4, wherein said at least five consecutive amino acids include SEQ ID NO:16;
   and
   (ii) it has at least one of the following advantageous properties:
   it binds to one epitope located between position amino acids 20 to 41 of SEQ ID NO:29;
   it does not bind to an epitope located between position amino acids 42 to 90 of SEQ ID NO:29, and/or between position amino acids 91 to 104 of SEQ ID NO:29;
   it does not bind to an epitope located between position amino acids 105 to 199 of SEQ ID NO:29; and
   it does not bind to an epitope located between position amino acids 200 to 298 of SEQ ID NO:29.

2. The antibody of claim 1, having at least one of the following additional advantageous properties:
   it does not compete with IL-34 ligand for binding to human CSF-1R; and
   it competes partially with CSF-1 ligand for binding to human CSF-1R.

3. The antibody of claim 2, having both of the said additional advantageous properties.

4. The antibody of claim 1, wherein in the presence of normal human peripheral blood mononuclear cells, it exerts antibody-dependent cellular cytotoxicity (ADCC) against CSF-1R-expressing human cells.

5. The antibody of claim 1, wherein it exerts antitumor effects against non-human animals bearing CSF-1R-expressing human cancer cells.

6. The antibody of claim 1, wherein it exerts antitumor effects against animals, including human, bearing CSF-1R-expressing human cancer cells.

7. The antibody of claim 1, wherein it inhibits the CSF-1-dependent proliferation of AML5 cells.

8. The antibody of claim 1, wherein it partially inhibits CSF-1-dependent phosphorylation of human CSF-1R.

9. The antibody of claim 1, wherein it comprises:
   an heavy chain selected from the group consisting of SEQ ID NO:37 and SEQ ID NO:38, and
   a light chain selected from the group consisting of SEQ NO:39, SEQ ID NO:40 and SEQ ID NO:41.

10. The antibody of claim 1, wherein it comprises:
    a first variable region selected from the group consisting of SEQ ID NO:42 and SEQ ID NO:43; and
    a second variable region selected from the group consisting of SEQ ID NO:44, SEQ ID NO:45 and SEQ ID NO:46.

11. The antibody of claim 1, wherein it comprises (a) an heavy chain consisting of SEQ ID NO:37, and (b) a light chain consisting of SEQ ID NO:39.

12. The antibody of claim 1, wherein it comprises (a) an heavy chain consisting of SEQ ID NO:38, and (b) a light chain consisting of SEQ ID NO:40.

13. The antibody of claim 1, wherein it comprises (a) an heavy chain consisting of SEQ ID NO:37, and (b) a light chain consisting of SEQ ID NO:41.

14. The antibody of claim 1, wherein it comprises (a) first variable region consisting of SEQ ID NO:42, and (b) a second variable region consisting of SEQ ID NO:44.

15. The antibody of claim 1, wherein it comprises (a) first variable region consisting of SEQ ID NO:43, and (b) a second variable region consisting of SEQ ID NO:45.

16. The antibody of claim 1, wherein it comprises (a) first variable region consisting of SEQ ID NO:42, and (b) a second variable region consisting of SEQ ID NO:46.

17. The antibody of claim 1, wherein it has a dissociation or affinity constant of less than 1 nM.

18. The antibody of claim 4, wherein in the CSF-1R-expressing human cells are CSF-1R-expressing human cancer cells.

* * * * *